United States Patent
Kmiec et al.

(10) Patent No.: US 12,171,813 B2
(45) Date of Patent: Dec. 24, 2024

(54) METHODS OF AND COMPOSITIONS FOR REDUCING GENE EXPRESSION AND/OR ACTIVITY

(71) Applicant: Christiana Care Gene Editing Institute, Inc., Wilmington, DE (US)

(72) Inventors: Eric B. Kmiec, Middletown, DE (US); Byung-Chun Yoo, Newark, DE (US); Pawel Bialk, Wilmington, DE (US)

(73) Assignee: Christiana Care Gene Editing Institute, Inc.

( * ) Notice: Subject to any disclaimer, the term of this patent is extended or adjusted under 35 U.S.C. 154(b) by 80 days.

(21) Appl. No.: 17/592,911

(22) Filed: Feb. 4, 2022

(65) Prior Publication Data

US 2022/0249626 A1    Aug. 11, 2022

Related U.S. Application Data

(60) Provisional application No. 63/146,057, filed on Feb. 5, 2021.

(51) Int. Cl.
| | |
|---|---|
| *A61K 38/46* | (2006.01) |
| *A61K 31/282* | (2006.01) |
| *A61K 31/337* | (2006.01) |
| *A61K 31/395* | (2006.01) |
| *A61K 31/7105* | (2006.01) |
| *A61K 33/243* | (2019.01) |
| *A61P 35/00* | (2006.01) |
| *C12N 9/22* | (2006.01) |
| *C12N 15/11* | (2006.01) |
| *C12N 15/85* | (2006.01) |
| *C12N 15/90* | (2006.01) |

(52) U.S. Cl.
CPC .......... *A61K 38/465* (2013.01); *A61K 31/282* (2013.01); *A61K 31/337* (2013.01); *A61K 31/5545* (2017.08); *A61K 31/7105* (2013.01); *A61K 33/243* (2019.01); *A61P 35/00* (2018.01); *C12N 9/22* (2013.01); *C12N 15/11* (2013.01); *C12N 15/85* (2013.01); *C12N 15/907* (2013.01); *C12N 2310/20* (2017.05); *C12N 2800/107* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 8,795,965 B2 | 8/2014 | Zhang | |
| 8,993,233 B2 | 3/2015 | Zhang et al. | |
| 9,567,603 B2 | 2/2017 | Joung et al. | |
| 9,587,252 B2 | 3/2017 | Church et al. | |
| 9,970,030 B2 | 5/2018 | Cameron et al. | |
| 10,266,850 B2 | 4/2019 | Doudna et al. | |
| 10,323,073 B2 | 6/2019 | Tremblay et al. | |
| 10,662,425 B2 | 5/2020 | Kantardzhieva et al. | |
| 10,704,060 B2 | 6/2020 | Gersbach et al. | |
| 10,731,181 B2 | 8/2020 | Chen et al. | |
| 11,261,428 B2 | 3/2022 | Benson et al. | |
| 11,286,478 B2 | 3/2022 | Zhang et al. | |
| 11,903,973 B2 * | 2/2024 | Bolen | C12N 9/22 |
| 2016/0281111 A1 | 9/2016 | Cotta-Ramusino et al. | |
| 2016/0298096 A1 | 10/2016 | Charpentier et al. | |
| 2017/0175128 A1 | 6/2017 | Welstead et al. | |
| 2017/0175144 A1 | 6/2017 | Zhang et al. | |
| 2018/0112213 A1 | 4/2018 | Welstead et al. | |
| 2018/0273932 A1 | 9/2018 | Bothmer et al. | |
| 2018/0360921 A1 | 12/2018 | Rodino-Klapac et al. | |
| 2018/0362975 A1 | 12/2018 | Chen et al. | |

(Continued)

FOREIGN PATENT DOCUMENTS

| | | |
|---|---|---|
| KR | 101908593 | 10/2018 |
| WO | 2014165825 | 10/2014 |

(Continued)

OTHER PUBLICATIONS

Guo et al (Genome Biology, 2018, 19:170, internet pp. 1-20).*
Sachdeva et al (Cancer Gene Therapy, 2015; 22:509-517).*
Jiang et al (Trends in Molecular Medicine, 2019, 25:1039-1049).*
Li et al (PLOS ONE, 2016, 11(1):e0144970, internet pp. 1-10).*
Lee et al (Oncotarget, 2016, 7:23874-23884).*
Ricciuti et al (Lung Cancer, 2018, 120:70-74).*
Mou et al (Genome Biology, 2017, 18:108, internet pp. 1-8 and supplemental Figures and Tables).*
Gao et al (Theranostics, 2020, 10:5137-5153).*
Gao et al Supplemental Figures (Theranostics, 2020).*

(Continued)

*Primary Examiner* — Laura B Goddard
(74) *Attorney, Agent, or Firm* — McCarter & English, LLP

(57) ABSTRACT

This disclosure relates to methods of and compositions for reducing expression or activity of a variant gene comprising at least one mutation as compared its wild-type gene, comprising introducing into a cell comprising the variant gene one or more DNA sequences encoding two or more gRNAs that are complementary to two or more target sequences in the variant gene, wherein at least one of the gRNAs hybridizes to a target sequence comprising a PAM site in the variant gene that results from a mutation to the variant gene creating the PAM site that does not exist in the wild-type gene or is operably linked to a mutated portion of the wild-type gene, at least one of the gRNAs hybridizes to a target sequence comprising a PAM site in an intron of the variant gene downstream or upstream from the PAM site, and a nucleic acid sequence encoding a CRISPR-associated endonuclease; wherein a CRISPR-associated endonuclease cleaves the variant gene at the target sequences; and expression or activity of the variant gene is reduced in the cell relative to a cell in which the one or more DNA sequences encoding the two or more gRNAs and the nucleic acid sequence encoding the CRISPR-associated endonuclease are not introduced.

18 Claims, 9 Drawing Sheets

Specification includes a Sequence Listing.

(56) References Cited

U.S. PATENT DOCUMENTS

| | | |
|---|---|---|
| 2019/0022192 A1 | 1/2019 | Ruan et al. |
| 2019/0048340 A1 | 2/2019 | Charpentier et al. |
| 2019/0055552 A1 | 2/2019 | Davidson et al. |
| 2019/0075770 A1 | 3/2019 | Shindo et al. |
| 2019/0100762 A1 | 4/2019 | Cigan et al. |
| 2019/0112353 A1 | 4/2019 | Yang et al. |
| 2019/0136230 A1 | 5/2019 | Sather et al. |
| 2019/0136231 A1 | 5/2019 | Morrissey et al. |
| 2019/0142972 A1 | 5/2019 | Burns et al. |
| 2019/0161742 A1 | 5/2019 | Cigan et al. |
| 2019/0248854 A1* | 8/2019 | Tremblay ............... A61P 21/00 |
| 2019/0264232 A1 | 8/2019 | Hou et al. |
| 2019/0275168 A1 | 9/2019 | Wu et al. |
| 2019/0284572 A1 | 9/2019 | Hunt et al. |
| 2019/0330643 A1 | 10/2019 | Rao et al. |
| 2020/0102561 A1 | 4/2020 | Mickanin et al. |
| 2020/0347386 A1 | 11/2020 | Benson et al. |
| 2020/0392541 A1 | 12/2020 | Zhang et al. |
| 2021/0032622 A1 | 2/2021 | Police et al. |
| 2021/0040507 A1 | 2/2021 | Moriarity et al. |
| 2021/0269783 A1 | 9/2021 | Liu et al. |
| 2021/0395784 A1 | 12/2021 | Lai et al. |
| 2022/0010321 A1 | 1/2022 | Lhuissier |
| 2022/0047618 A1 | 2/2022 | Ligocki et al. |
| 2022/0049274 A1 | 2/2022 | Myung et al. |
| 2022/0110974 A1 | 4/2022 | Cho et al. |
| 2022/0249626 A1 | 8/2022 | Kmiec et al. |
| 2022/0290186 A1 | 9/2022 | Kotin et al. |

FOREIGN PATENT DOCUMENTS

| | | |
|---|---|---|
| WO | 2014204724 | 12/2014 |
| WO | 2015089473 | 6/2015 |
| WO | 2015089486 | 6/2015 |
| WO | 2016021973 | 2/2016 |
| WO | 2016028682 | 2/2016 |
| WO | 2016183236 | 11/2016 |
| WO | 2016205764 | 12/2016 |
| WO | 2017062983 | 4/2017 |
| WO | 2017070284 | 4/2017 |
| WO | 2017075475 | 5/2017 |
| WO | 2017155715 | 9/2017 |
| WO | 2018015444 | 1/2018 |
| WO | 2018039145 | 3/2018 |
| WO | 2018107028 | 6/2018 |
| WO | 2018119182 | 6/2018 |
| WO | 2018170184 | 9/2018 |
| WO | 2019089884 | 5/2019 |
| WO | 2019090202 | 5/2019 |
| WO | 2019116349 | 6/2019 |
| WO | 2019123429 | 6/2019 |
| WO | 2019178427 | 9/2019 |
| WO | 2019241452 | 12/2019 |
| WO | 2020046861 | 3/2020 |
| WO | 2020127487 | 6/2020 |
| WO | 2020168122 | 8/2020 |
| WO | 2020176463 | 9/2020 |
| WO | 2020225754 | 11/2020 |
| WO | 2020231863 | 11/2020 |
| WO | 2021050593 | 3/2021 |
| WO | 2021050601 | 3/2021 |
| WO | 2021087394 | 5/2021 |
| WO | 2021113763 | 6/2021 |
| WO | 2021113769 | 6/2021 |
| WO | 2021138247 | 7/2021 |
| WO | 2021188729 | 9/2021 |
| WO | 2021217002 | 10/2021 |
| WO | 2021231437 | 11/2021 |
| WO | 2022075816 | 4/2022 |
| WO | 2022120089 | 6/2022 |
| WO | 2022147321 | 7/2022 |

OTHER PUBLICATIONS

Fok (2014 dissertation, Master of Science to the Faculty of Health Sciences at the University of the Witwatersrand, Johannesburg, South Africa).*

Mou et al, supplemental Figures and Tables, (Genome Biology, 2017).*

International Search Report based on PCT International Application No. PCT/US2020/015261, dated Jul. 25, 2022, pp. 1-9.

Written Opinion based on PCT International Application No. PCT/US2020/015261, dated Jul. 25, 2022, pp. 1-13.

Bonafont, Jose, et al., "Clinically Relevant Correction of Recessive Dystrophic Epidermolysis Bullosa by Dual sgRNA CRISPR/Cas9-Mediated Gene Editing", Molecular Therapy, May 1, 2019, vol. 27, No. 5, pp. 986-998.

Wan Shin, Jun, et al. "Permanent Inactivation of Huntington's Disease Mutation by Personalized Allele-specific CRISPR/Cas9", Human Molecular Genetics, Sep. 15, 2016, vol. 25, No. 20, pp. 4566-4576.

Banas, Kelly, et al., "Exon Skipping Induced by CRISPR-directed Gene Editing Regulates the Response to Chemotherapy in Non-Small Cell Lung Carcinoma Cells", Gene Therapy, 2022, vol. 29, pp. 357-367.

Bloh, Kevin, et al., "Deconvolution of Complex DNA Repair (DECODR): Establishing a Novel Deconvolution Algorithm for Comprehensive Analysis of CRISPR-Edited Sanger Sequence Data", The CRISPR Journal, 2021, vol. 4, No. 1, pp. 120-131.

* cited by examiner

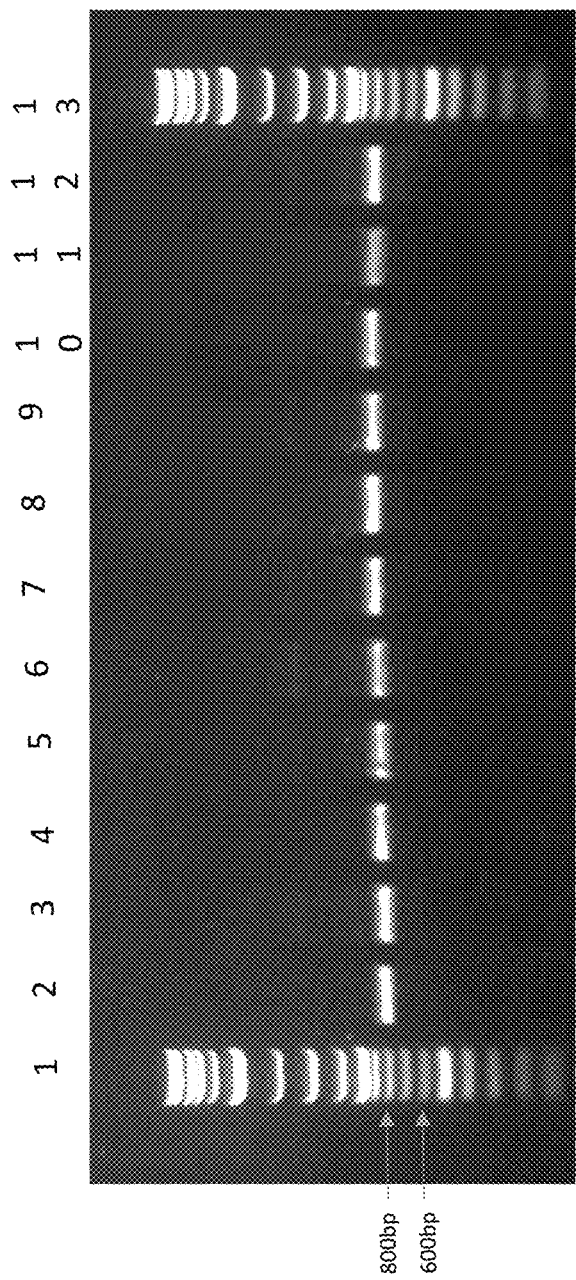

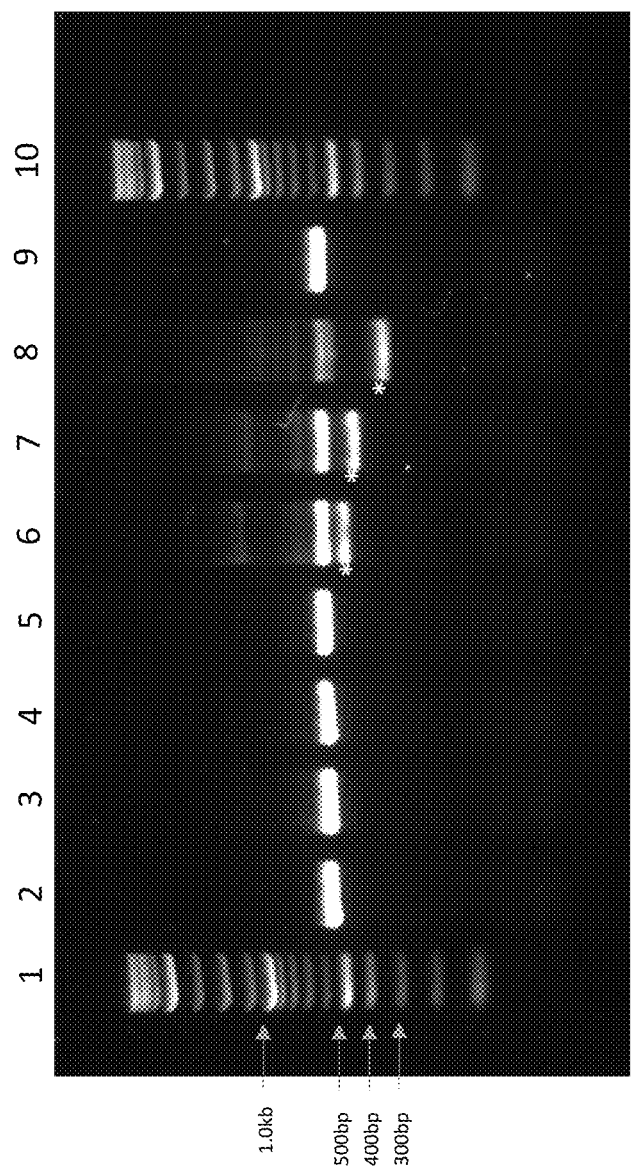

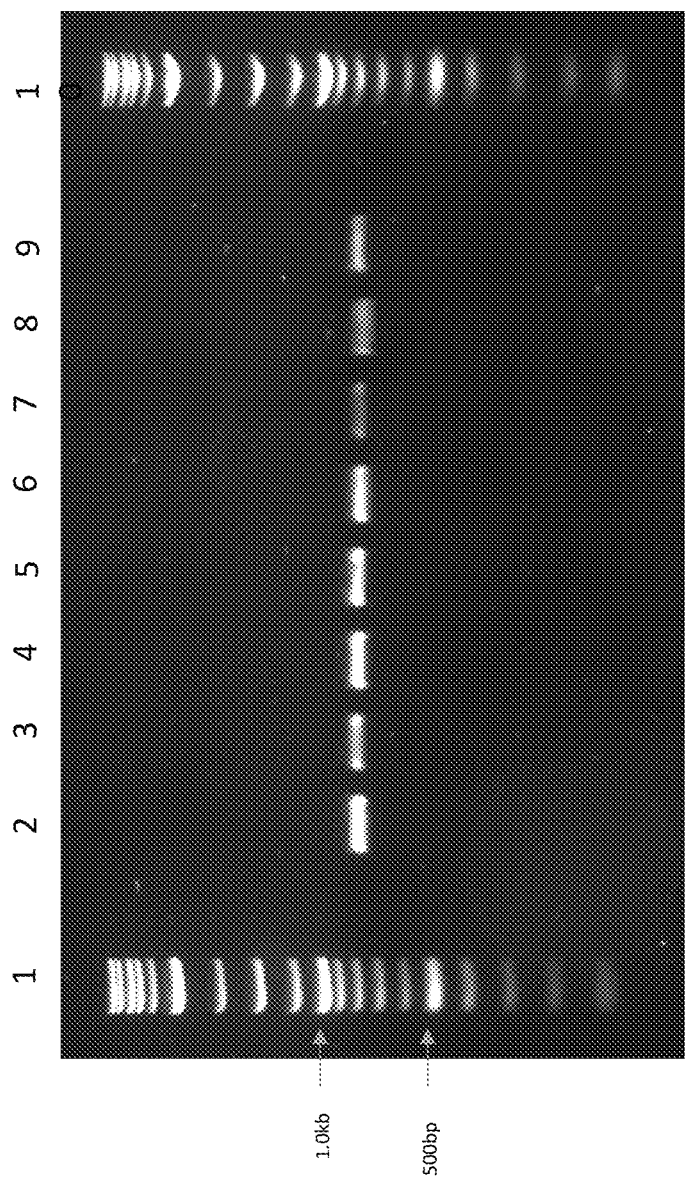

METHODS OF AND COMPOSITIONS FOR REDUCING GENE EXPRESSION AND/OR ACTIVITY

CROSS-REFERENCE TO RELATED APPLICATION

This application claims the benefit of Provisional U.S. Patent Application No. 63/146,057, filed Feb. 5, 2021, which is incorporated herein, in its entirety, by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 130949-00901sequencelisting.txt. The size of the text file is 10 KB, and the text file was created on Feb. 4, 2022.

FIELD

The field relates to gene editing using CRISPR/Cas systems to reduce gene expression and/or activity.

BACKGROUND

Clustered Regularly Interspaced Short Palindromic Repeats (CRISPR) and the CRISPR-associated (Cas) genes, collectively known as CRISPR/Cas systems, are currently understood to provide immunity to bacteria and archaea against phage infection. The CRISPR/Cas systems of prokaryotic adaptive immunity are an extremely diverse group of proteins effectors, non-coding elements, as well as loci architectures, some examples of which have been engineered and adapted to produce important biotechnologies.

The components of the system involved in host defense include one or more effector proteins capable of modifying DNA or RNA and an RNA guide element that is responsible to targeting these protein activities to a specific sequence on the phage DNA or RNA. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

The ability to precisely modify genetic material in eukaryotic cells enables a wide range of high value applications in medical, pharmaceutical, agricultural, basic research, and other fields. Fundamentally, genome engineering provides this capability by introducing predefined genetic variation at specific locations in eukaryotic genomes, such as deleting, inserting, mutating, or substituting specific nucleic acid sequences. These alterations can be gene- or location-specific. There remains a need, however, to improve the efficiency of producing functional knockouts.

SUMMARY

One aspect is for a method of reducing expression or activity of a variant gene comprising at least one mutation as compared its wild-type gene, comprising introducing into a cell comprising the variant gene (a) one or more nucleic acid sequences encoding two or more guide RNAs (gRNAs) that are complementary to two or more target sequences in the variant gene, wherein (i) one or more of the gRNAs hybridizes to a target sequence comprising a protospacer adjacent motif (PAM) site in the variant gene that (A) results from a mutation to the variant gene creating the PAM site that does not exist in the wild-type gene or (B) is operably linked to a mutated portion of the wild-type gene, and (ii) one or more of the gRNAs hybridizes to a target sequence comprising a PAM site in an intron of the variant gene downstream or upstream from the PAM site of (i), and (b) one or more nucleic acid sequences encoding one or more Clustered Regularly Interspaced Short Palindromic Repeat (CRISPR)-associated endonucleases; wherein (c) the one or more CRISPR-associated endonucleases cleave the variant gene at the target sequences of (i) and (ii); and (d) expression or activity of the variant gene is reduced in the cell relative to a cell in which the one or more nucleic acid sequences encoding the two or more gRNAs and the one or more nucleic acid sequences encoding one or more CRISPR-associated endonucleases are not introduced. In some embodiments, the two or more gRNAs comprise a trans-activated small RNA (tracrRNA) and a CRISPR RNA (crRNA). In some embodiments, the two or more gRNAs are each one or more single guide RNAs. In some embodiments, at least one of the one or more CRISPR-associated endonucleases is a class 2 CRISPR-associated endonuclease, and in some embodiments, the class 2 CRISPR-associated endonuclease is Cas9 or Cas12a. In some embodiments, expression of one or more allele(s) of the variant gene is reduced in the cell. In some embodiments, activity of a polypeptide encoded by the variant gene is reduced in the cell. In some embodiments, expression of the variant gene or activity of a polypeptide encoded by the variant gene is not completely eliminated in the cell. In some embodiments, expression of the variant gene or activity of a polypeptide encoded by the variant gene is completely eliminated in the cell. In some embodiments, expression of the wild-type gene or activity of a polypeptide encoded by the wild-type gene in a non-cancerous cell of a subject that contains the cell is unaffected by the introduction of the one or more DNA sequences of (a) and the nucleic acid sequence of (b).

Another aspect is for a cancer cell comprising a mutated variant gene produced by the aforementioned method.

A further aspect is for a method of reducing expression or activity of a variant gene in a cancer cell comprising introducing into the cancer cell (a) two or more guide RNAs (gRNAs) that are complementary to two or more target sequences in the variant gene, wherein (i) at least one of the gRNAs hybridizes to a target sequence comprising a protospacer adjacent motif (PAM) site in the variant gene that (A) results from a mutation to the variant gene creating the PAM site that does not exist in the wild-type gene or (B) is operably linked to a mutated portion of the wild-type gene, and (ii) at least one of the gRNAs hybridizes to a target sequence comprising a PAM site in an intron of the variant gene downstream or upstream from the PAM site of (i), and (b) one or more CRISPR-associated endonucleases; whereby one or more CRISPR-associated endonucleases cleave the variant gene at the target sequence of (i) and the target sequence of (ii); and wherein expression or activity of the variant gene is reduced in the cell relative to a cell in which the two or more gRNAs and the one or more CRISPR-associated endonucleases are not introduced. In some embodiments, the two or more gRNAs comprise a tracrRNA and a crRNA. In some embodiments, the two or more gRNAs are each one or more single guide RNAs. In some embodiments, at least one of the one or more CRISPR-associated endonuclease is a class 2 CRISPR-associated endonuclease, and in some embodiments, the class 2 CRISPR-associated endonuclease is Cas9 or Cas12a. In some embodiments, expression of one or more allele(s) of the variant gene is reduced in the cancer cell. In some embodiments, activity of a polypeptide encoded by the variant gene is reduced in the cancer cell. In some embodiments, expression of the variant gene or activity of a polypeptide encoded by the variant gene is not completely eliminated in the cancer cell.

In some embodiments, expression of the variant gene or activity of a polypeptide encoded by the variant gene is completely eliminated in the cancer cell. In some embodiments, expression or activity of the wild-type gene in a non-cancerous cell of a subject that contains the cancer cell is unaffected by the introduction of the two or more gRNAs of (a) and the CRISPR-associated endonuclease of (b).

An additional embodiment is for a cancer cell comprising a mutated variant gene produced by the aforementioned method.

Another embodiment is for a pharmaceutical composition comprising two or more gRNAs, each gRNA comprising a DNA-binding domain and a CRISPR-associated endonuclease protein-binding domain, wherein (a) the DNA-binding domain of at least one of the gRNAs is complementary to a target sequence comprising a protospacer adjacent motif (PAM) site in the variant gene that (i) results from a mutation to the variant gene creating the PAM site that does not exist in the wild-type gene or (ii) is operably linked to a mutated portion of the wild-type gene; and (b) at least one of the gRNAs is complementary to a target sequence comprising a PAM site in an intron of the variant gene downstream or upstream from the PAM site of (a). In some embodiments, the two or more gRNAs comprise a tracrRNA and a crRNA. In some embodiments, the two or more gRNAs are each one or more single guide RNAs. In some embodiments, the pharmaceutical composition further comprises one or more CRISPR-associated endonucleases; in some embodiments, at least one of the one or more CRISPR-associated endonucleases is a class 2 CRISPR-associated endonuclease; and in some embodiments, the class 2 CRISPR-associated endonuclease is Cas9 or Cas12a.

A further aspect is for a ribonucleoprotein (RNP) complex comprising (a) two or more gRNAs, each gRNA comprising a DNA-binding domain and a CRISPR-associated endonuclease protein-binding domain, wherein (i) the DNA-binding domain of at least one of the gRNAs is complementary to a target sequence comprising a protospacer adjacent motif (PAM) site in the variant gene that (A) results from a mutation to the variant gene creating the PAM site that does not exist in the wild-type gene or (B) is operably linked to a mutated portion of the wild-type gene; and (ii) at least one of the gRNAs is complementary to a target sequence comprising a PAM site in an intron of the variant gene downstream or upstream from the PAM site of (i); and (b) one or more CRISPR-associated endonucleases. In some embodiments, the two or more gRNAs comprise a tracrRNA and a crRNA. In some embodiments, the two or more gRNAs are each one or more single guide RNAs. In some embodiments, at least one of the one or more CRISPR-associated endonucleases is a class 2 CRISPR-associated endonuclease, and in some embodiments, the class 2 CRISPR-associated endonuclease is Cas9 or Cas12a.

An additional aspect is for a pharmaceutical composition comprising the aforementioned RNP complex.

Another aspect is for a method of treating cancer in a subject comprising administering to the subject a therapeutically effective amount of the aforementioned pharmaceutical composition. In some embodiments, expression of the wild-type gene or activity of a polypeptide encoded by the wild-type gene in a non-cancerous cell of the subject is unaffected by the administration of the pharmaceutical composition. In some embodiments, the cancer is resistant to one or more chemotherapeutic agents. In some embodiments, the method further comprises administering one or more chemotherapeutic agents to the subject, and in some embodiments, the one or more chemotherapeutic agents are selected from the group consisting of cisplatin, vinorelbine, carboplatin, paclitaxel, and a combination thereof. In some embodiments, the pharmaceutical composition is administered in an amount sufficient to reduce proliferation of cells of the cancer relative to cancer cells that are not treated with the pharmaceutical composition. In some embodiments, the pharmaceutical composition is administered in an amount sufficient to reduce tumor growth relative to a tumor that is not treated with the pharmaceutical composition. In some embodiments, the pharmaceutical composition is administered in an amount sufficient to reduce proliferation of cells of the cancer relative to cancer cells that are treated with the at least one chemotherapeutic agent but are not treated with the pharmaceutical composition. In some embodiments, the pharmaceutical composition is administered in an amount sufficient to reduce tumor growth relative to a tumor that is treated with the at least one chemotherapeutic agent but is not treated with the pharmaceutical composition. In some embodiments, the cancer is a lymphoid neoplasm diffuse large B-cell lymphoma, cholangiocarcinoma, uterine carcinosarcoma, kidney chromophobe, uveal melanoma, mesothelioma, adrenocortical carcinoma, thymoma, acute myeloid leukemia, testicular germ cell tumor, rectum adenocarcinoma, pancreatic adenocarcinoma, phenochromocytoma and paraganglioma, esophageal carcinoma, sarcoma, kidney renal papillary cell carcinoma, cervical squamous cell carcinoma and endocervical adenocarcinoma, kidney renal clear cell carcinoma, liver hepatocellular carcinoma, glioblastoma multiforme, bladder urothelial carcinoma, colon adenocarcinoma, stomach adenocarcinoma, ovarian serous cystadenocarcinoma, skin cutaneous melanoma, prostate adenocarcinoma, thyroid carcinoma, lung squamous cell carcinoma, head and neck squamous cell carcinoma, brain lower grade glioma, uterine corpus endometrial carcinoma, lung adenocarcinoma, multiple myeloma, breast invasive carcinoma, acute lymphoblastic leukemia, acute myeloid leukemia, adrenocortical carcinoma, Kaposi sarcoma, AIDS-related lymphoma, primary CNS lymphoma, anal cancer, astrocytoma, atypical teratoid/rhabdoid tumor, bile duct cancer, bladder cancer, bone cancer, brain tumor, breast cancer, bronchial tumors, carcinoid tumor, carcinoma of unknown primary, cardiac tumor, medulloblastoma, germ cell tumor, cervical cancer, chordoma, chronic lymphocytic leukemia, chronic myelogenous leukemia, chronic myeloproliferative neoplasm, colorectal cancer, craniopharyngioma, embryonal tumor, endometrial cancer, ependymoma, esophageal cancer, esthesioneuroblastoma, Ewing sarcoma, extracranial germ cell tumor, extragonadal germ cell tumor, intraocular melanoma, retinoblastoma, fallopian tube cancer, fibrous histiocytoma of bone, osteosarcoma, gallbladder cancer, gastric cancer, gastrointestinal carcinoid tumor, gastrointestinal stromal tumor, CNS germ cell tumor, ovarian germ cell tumor, testicular cancer, gestational trophoblastic disease, hairy cell leukemia, head and neck cancer, hepatocellular cancer, Langerhans cell histiocytosis, Hodgkin lymphoma, hypopharyngeal cancer, islet cell tumor, kidney cancer, laryngeal cancer, leukemia, lip and oral cavity cancer, lung cancer, lymphoma, male breast cancer, malignant fibrous histiocytoma of bone, melanoma, Merkel cell carcinoma, malignant mesothelioma, metastatic cancer, metastatic squamous cell neck cancer with occult primary, midline tract carcinoma, mouth cancer, multiple endocrine neoplasia, plasma cell neoplasm, mycosis fungoides, myelodysplastic syndrome, myelodysplastic neoplasm, nasal cavity and paranasal sinus cancer, nasopharyngeal cancer, neuroblastoma, non-Hodgkin lymphoma, oropharyngeal cancer, ovarian cancer, pancreatic cancer, papillomatosis, paraganglioma, parathyroid cancer, pharyngeal cancer, pheochromocytoma, pituitary tumor, pleuropulmonary blastoma, primary peritoneal cancer, prostate cancer, rectal cancer, rhabdomyosarcoma, salivary gland cancer, Sezary syndrome, skin cancer, small intestine cancer, soft tissue sarcoma, testicular cancer, thymoma, thymic carcinoma, thyroid cancer, transitional cell cancer of the renal pelvis and ureter, urethral cancer, endometrial uterine cancer, uterine sarcoma, vaginal cancer, vascular tumor, vulvar cancer, or Wilms tumor; and in some embodiments, the lung cancer is a non-small cell lung cancer, small cell lung cancer, pleuropulmonary blastoma, or tracheobronchial tumor. In some embodiments, the subject is a human.

A further aspect is for a CRISPR system for use as a medicament, the CRISPR system comprising (a) two or more gRNAs, each gRNA comprising a DNA-binding domain and a CRISPR-associated endonuclease protein-binding domain, wherein (i) the DNA-binding domain of at least one of the gRNAs is complementary to a target sequence comprising a protospacer adjacent motif (PAM) site in the variant gene that (A) results from a mutation to the variant gene creating the PAM site that does not exist in the wild-type gene or (B) is operably linked to a mutated portion of the wild-type gene; and (ii) at least one of the gRNAs is complementary to a target sequence comprising a PAM site in an intron of the variant gene downstream or upstream from the PAM site of (i); and (b) one or more CRISPR-associated endonucleases. In some embodiments, the two or more gRNAs comprise a tracrRNA and a crRNA. In some embodiments, the two or more gRNAs are each one or more single gRNA.

An additional aspect of the aforementioned CRISPR system is for use in treating cancer. In some embodiments, the cancer is resistant to one or more chemotherapeutic agents. In some embodiments, the CRISPR system for use further comprises one or more chemotherapeutic agents, and in some embodiments, the one or more chemotherapeutic agents are selected from the group consisting of cisplatin, vinorelbine, carboplatin, paclitaxel, and a combination thereof. In some embodiments, at least one of the one or more CRISPR-associated endonucleases is a class 2 CRISPR-associated endonuclease, and in some embodiments, the class 2 CRISPR-associated endonuclease is Cas9 or Cas12a. In some embodiments, the cancer is a lymphoid neoplasm diffuse large B-cell lymphoma, cholangiocarcinoma, uterine carcinosarcoma, kidney chromophobe, uveal melanoma, mesothelioma, adrenocortical carcinoma, thymoma, acute myeloid leukemia, testicular germ cell tumor, rectum adenocarcinoma, pancreatic adenocarcinoma, phenochromocytoma and paraganglioma, esophageal carcinoma, sarcoma, kidney renal papillary cell carcinoma, cervical squamous cell carcinoma and endocervical adenocarcinoma, kidney renal clear cell carcinoma, liver hepatocellular carcinoma, glioblastoma multiforme, bladder urothelial carcinoma, colon adenocarcinoma, stomach adenocarcinoma, ovarian serous cystadenocarcinoma, skin cutaneous melanoma, prostate adenocarcinoma, thyroid carcinoma, lung squamous cell carcinoma, head and neck squamous cell carcinoma, brain lower grade glioma, uterine corpus endometrial carcinoma, lung adenocarcinoma, multiple myeloma, breast invasive carcinoma, acute lymphoblastic leukemia, acute myeloid leukemia, adrenocortical carcinoma, Kaposi sarcoma, AIDS-related lymphoma, primary CNS lymphoma, anal cancer, astrocytoma, atypical teratoid/rhabdoid tumor, bile duct cancer, bladder cancer, bone cancer, brain tumor, breast cancer, bronchial tumors, carcinoid tumor, carcinoma of unknown primary, cardiac tumor, medulloblastoma, germ cell tumor, cervical cancer, chordoma, chronic lymphocytic leukemia, chronic myelogenous leukemia, chronic myeloproliferative neoplasm, colorectal cancer, craniopharyngioma, embryonal tumor, endometrial cancer, ependymoma, esophageal cancer, esthesioneuroblastoma, Ewing sarcoma, extracranial germ cell tumor, extragonadal germ cell tumor, intraocular melanoma, retinoblastoma, fallopian tube cancer, fibrous histiocytoma of bone, osteosarcoma, gallbladder cancer, gastric cancer, gastrointestinal carcinoid tumor, gastrointestinal stromal tumor, CNS germ cell tumor, ovarian germ cell tumor, testicular cancer, gestational trophoblastic disease, hairy cell leukemia, head and neck cancer, hepatocellular cancer, Langerhans cell histiocytosis, Hodgkin lymphoma, hypopharyngeal cancer, islet cell tumor, kidney cancer, laryngeal cancer, leukemia, lip and oral cavity cancer, lung cancer, lymphoma, male breast cancer, malignant fibrous histiocytoma of bone, melanoma, Merkel cell carcinoma, malignant mesothelioma, metastatic cancer, metastatic squamous cell neck cancer with occult primary, midline tract carcinoma, mouth cancer, multiple endocrine neoplasia, plasma cell neoplasm, mycosis fungoides, myelodysplastic syndrome, myelodysplastic neoplasm, nasal cavity and paranasal sinus cancer, nasopharyngeal cancer, neuroblastoma, non-Hodgkin lymphoma, oropharyngeal cancer, ovarian cancer, pancreatic cancer, papillomatosis, paraganglioma, parathyroid cancer, pharyngeal cancer, pheochromocytoma, pituitary tumor, pleuropulmonary blastoma, primary peritoneal cancer, prostate cancer, rectal cancer, rhabdomyosarcoma, salivary gland cancer, Sezary syndrome, skin cancer, small intestine cancer, soft tissue sarcoma, testicular cancer, thymoma, thymic carcinoma, thyroid cancer, transitional cell cancer of the renal pelvis and ureter, urethral cancer, endometrial uterine cancer, uterine sarcoma, vaginal cancer, vascular tumor, vulvar cancer, or Wilms tumor; and in some embodiments, the lung cancer is a non-small cell lung cancer, small cell lung cancer, pleuropulmonary blastoma, or tracheobronchial tumor.

Another aspect is for an RNP complex for use as a medicament, the RNP complex comprising (a) two or more gRNAs, each gRNA comprising a DNA-binding domain and a CRISPR-associated endonuclease protein-binding domain, wherein (i) the DNA-binding domain of at least one of the gRNAs is complementary to a target sequence comprising a protospacer adjacent motif (PAM) site in the variant gene that (A) results from a mutation to the variant gene creating the PAM site that does not exist in the wild-type gene or (B) is operably linked to a mutated portion of the wild-type gene; and (ii) at least one of the gRNAs is complementary to a target sequence comprising a PAM site in an intron of the variant gene downstream or upstream from the PAM site of (i); and (b) one or more CRISPR-associated endonucleases. In some embodiments, the two or more gRNAs comprise a tracrRNA and a crRNA. In some embodiments, the two or more gRNAs are each one or more single gRNAs.

A further aspect is for use of the aforementioned RNP complex in treating cancer. In some embodiments, the cancer is resistant to one or more chemotherapeutic agents. In some embodiments, the RNP complex for use further comprises one or more chemotherapeutic agents, and in some embodiments, the one or more chemotherapeutic agents are selected from the group consisting of cisplatin, vinorelbine, carboplatin, paclitaxel, and a combination thereof. In some embodiments, at least one of the one or more CRISPR-associated endonucleases is a class 2 CRISPR-associated endonuclease, and in some embodiments, the class 2 CRISPR-associated endonuclease is Cas9 or Cas12a. In some embodiments, the cancer is a lymphoid neoplasm diffuse large B-cell lymphoma, cholangiocarcinoma, uterine carcinosarcoma, kidney chromophobe, uveal melanoma, mesothelioma, adrenocortical carcinoma, thymoma, acute myeloid leukemia, testicular germ cell tumor, rectum adenocarcinoma, pancreatic adenocarcinoma, phenochromocytoma and paraganglioma, esophageal carcinoma, sarcoma, kidney renal papillary cell carcinoma, cervical squamous cell carcinoma and endocervical adenocarcinoma, kidney renal clear cell carcinoma, liver hepatocellular carcinoma, glioblastoma multiforme, bladder urothelial carcinoma, colon adenocarcinoma, stomach adenocarcinoma, ovarian serous cystadenocarcinoma, skin cutaneous melanoma, prostate adenocarcinoma, thyroid carcinoma, lung squamous cell carcinoma, head and neck squamous cell carcinoma, brain lower grade glioma, uterine corpus endometrial carcinoma, lung adenocarcinoma, multiple myeloma, breast invasive carcinoma, acute lymphoblastic leukemia, acute myeloid leukemia, adrenocortical carcinoma, Kaposi sarcoma, AIDS-related lymphoma, primary CNS lymphoma, anal cancer, astrocytoma, atypical teratoid/rhabdoid tumor, bile duct cancer, bladder cancer, bone cancer, brain tumor, breast cancer, bronchial tumors, carcinoid tumor, carcinoma of unknown primary, cardiac tumor, medulloblastoma, germ cell tumor, cervical cancer, chordoma, chronic lymphocytic leukemia, chronic myelogenous leukemia, chronic myeloproliferative neoplasm, colorectal cancer, craniopharyngioma, embryonal tumor, endometrial cancer, ependymoma, esophageal cancer, esthesioneuroblastoma, Ewing sarcoma, extracranial germ cell tumor, extragonadal germ cell tumor, intraocular melanoma, retinoblastoma, fallopian tube cancer, fibrous histiocytoma of bone, osteosarcoma, gallbladder cancer, gastric cancer, gastrointestinal carcinoid tumor, gastrointestinal stromal tumor, CNS germ cell tumor, ovarian germ cell tumor, testicular cancer, gestational trophoblastic disease, hairy cell leukemia, head and neck cancer, hepatocellular cancer, Langerhans cell histiocytosis, Hodgkin lymphoma, hypopharyngeal cancer, islet cell tumor, kidney cancer, laryngeal cancer, leukemia, lip and oral cavity cancer, lung cancer, lymphoma, male breast cancer, malignant fibrous histiocytoma of bone, melanoma, Merkel cell carcinoma, malignant mesothelioma, metastatic cancer, metastatic squamous cell neck cancer with occult primary, midline tract carcinoma, mouth cancer, multiple endocrine neoplasia, plasma cell neoplasm, mycosis fungoides, myelodysplastic syndrome, myelodysplastic neoplasm, nasal cavity and paranasal sinus cancer, nasopharyngeal cancer, neuroblastoma, non-Hodgkin lymphoma, oropharyngeal cancer, ovarian cancer, pancreatic cancer, papillomatosis, paraganglioma, parathyroid cancer, pharyngeal cancer, pheochromocytoma, pituitary tumor, pleuropulmonary blastoma, primary peritoneal cancer, prostate cancer, rectal cancer, rhabdomyosarcoma, salivary gland cancer, Sezary syndrome, skin cancer, small intestine cancer, soft tissue sarcoma, testicular cancer, thymoma, thymic carcinoma, thyroid cancer, transitional cell cancer of the renal pelvis and ureter, urethral cancer, endometrial uterine cancer, uterine sarcoma, vaginal cancer, vascular tumor, vulvar cancer, or Wilms tumor; and in some embodiments, the lung cancer is a non-small cell lung cancer, small cell lung cancer, pleuropulmonary blastoma, or tracheobronchial tumor.

An additional aspect is a vector comprising two or more gRNAs, each gRNA comprising a DNA-binding domain and a CRISPR-associated endonuclease protein-binding domain, wherein (i) the DNA-binding domain of at least one of the gRNAs is complementary to a target sequence comprising a protospacer adjacent motif (PAM) site in a variant gene of a wild-type gene that (A) results from a mutation to the variant gene creating the PAM site that does not exist in the wild-type gene or (B) is operably linked to a mutated portion of the wild-type gene; and (ii) at least one of the gRNAs is complementary to a target sequence comprising a PAM site in an intron of the variant gene downstream or upstream from the PAM site of (i). In some embodiments, the two or more gRNAs comprise a tracrRNA and a crRNA. In some embodiments, the two or more gRNAs are each one or more single gRNAs. In some embodiments, the vector is for use as a medicament; in some embodiments, the vector for use in treating cancer; in some embodiments, the cancer is resistant to one or more chemotherapeutic agents; in some embodiments, the cancer is a lymphoid neoplasm diffuse large B-cell lymphoma, cholangiocarcinoma, uterine carcinosarcoma, kidney chromophobe, uveal melanoma, mesothelioma, adrenocortical carcinoma, thymoma, acute myeloid leukemia, testicular germ cell tumor, rectum adenocarcinoma, pancreatic adenocarcinoma, phenochromocytoma and paraganglioma, esophageal carcinoma, sarcoma, kidney renal papillary cell carcinoma, cervical squamous cell carcinoma and endocervical adenocarcinoma, kidney renal clear cell carcinoma, liver hepatocellular carcinoma, glioblastoma multiforme, bladder urothelial carcinoma, colon adenocarcinoma, stomach adenocarcinoma, ovarian serous cystadenocarcinoma, skin cutaneous melanoma, prostate adenocarcinoma, thyroid carcinoma, lung squamous cell carcinoma, head and neck squamous cell carcinoma, brain lower grade glioma, uterine corpus endometrial carcinoma, lung adenocarcinoma, multiple myeloma, breast invasive carcinoma, acute lymphoblastic leukemia, acute myeloid leukemia, adrenocortical carcinoma, Kaposi sarcoma, AIDS-related lymphoma, primary CNS lymphoma, anal cancer, astrocytoma, atypical teratoid/rhabdoid tumor, bile duct cancer, bladder cancer, bone cancer, brain tumor, breast cancer, bronchial tumors, carcinoid tumor, carcinoma of unknown primary, cardiac tumor, medulloblastoma, germ cell tumor, cervical cancer, chordoma, chronic lymphocytic leukemia, chronic myelogenous leukemia, chronic myeloproliferative neoplasm, colorectal cancer, craniopharyngioma, embryonal tumor, endometrial cancer, ependymoma, esophageal cancer, esthesioneuroblastoma, Ewing sarcoma, extracranial germ cell tumor, extragonadal germ cell tumor, intraocular melanoma, retinoblastoma, fallopian tube cancer, fibrous histiocytoma of bone, osteosarcoma, gallbladder cancer, gastric cancer, gastrointestinal carcinoid tumor, gastrointestinal stromal tumor, CNS germ cell tumor, ovarian germ cell tumor, testicular cancer, gestational trophoblastic disease, hairy cell leukemia, head and neck cancer, hepatocellular cancer, Langerhans cell histiocytosis, Hodgkin lymphoma, hypopharyngeal cancer, islet cell tumor, kidney cancer, laryngeal cancer, leukemia, lip and oral cavity cancer, lung cancer, lymphoma, male breast cancer, malignant fibrous histiocytoma of bone, melanoma, Merkel cell carcinoma, malignant mesothelioma, metastatic cancer, metastatic squamous cell neck cancer with occult primary, midline tract carcinoma, mouth cancer, multiple endocrine neoplasia, plasma cell neoplasm, mycosis fungoides, myelodysplastic syndrome, myelodysplastic neoplasm, nasal cavity and paranasal sinus cancer, nasopharyngeal cancer, neuroblastoma, non-Hodgkin lymphoma, oropharyngeal cancer, ovarian cancer, pancreatic cancer, papillomatosis, paraganglioma, parathyroid cancer, pharyngeal cancer, pheochromocytoma, pituitary tumor, pleuropulmonary blastoma, primary peritoneal cancer, prostate cancer, rectal cancer, rhabdomyosarcoma, salivary gland cancer, Sezary syndrome, skin cancer, small intestine cancer, soft tissue sarcoma, testicular cancer, thymoma, thymic carcinoma, thyroid cancer, transitional cell cancer of the renal pelvis and ureter, urethral cancer, endometrial uterine cancer, uterine sarcoma, vaginal cancer, vascular tumor, vulvar cancer, or Wilms tumor; and in some embodiments, the lung cancer is a non-small cell lung cancer, small cell lung cancer, pleuropulmonary blastoma, or tracheobronchial tumor. In some embodiments, the vector for use further comprises one or more chemotherapeutic agents; and in some embodiments, the one or more chemotherapeutic agents are selected from the group consisting of cisplatin, vinorelbine, carboplatin, paclitaxel, and a combination thereof.

Another aspect is for a method of reducing expression or activity of a gene comprising introducing into a cell (a) two or more guide RNAs (gRNAs) that are complementary to two or more target sequences in the gene, wherein (i) at least one of the gRNAs hybridizes to a target sequence comprising a protospacer adjacent motif (PAM) site in an exon of the gene and (ii) at least one of the gRNAs hybridizes to a target sequence comprising a PAM site in an intron of the variant gene downstream or upstream from the PAM site of (i), and (b) one or more CRISPR-associated endonucleases; whereby one or more CRISPR-associated endonucleases cleave the gene at the target sequence of (i) and the target sequence of (ii); and wherein expression or activity of the gene is reduced in the cell relative to a cell in which the two or more gRNAs or the one or more CRISPR-associated endonucleases are not introduced. In some embodiments, the two or more gRNAs comprise a tracrRNA and a crRNA. In some embodiments, the two or more gRNAs are each one or more single guide RNAs. In some embodiments, at least one of the one or more CRISPR-associated endonucleases is a class 2 CRISPR-associated endonuclease; and in some embodiments, the class 2 CRISPR-associated endonuclease is Cas9 or Cas12a. In some embodiments, expression of one or more allele(s) of the gene is reduced in the cell. In some embodiments, activity of a polypeptide encoded by the gene is reduced in the cell. In some embodiments, expression of the gene or activity of a polypeptide encoded by the gene is not completely eliminated in the cell. In some embodiments, expression of the variant gene or activity of a polypeptide encoded by the variant gene is completely eliminated in the cancer cell. In some embodiments, expression or activity of the variant gene is reduced in the cell relative to a cell in which the two or more gRNAs and the one or more CRISPR-associated endonucleases are not introduced.

Other objects and advantages will become apparent to those skilled in the art upon reference to the detailed description that hereinafter follows.

The insert illustrates cis-elements involved in splicing process (Pagani et al., Nat. Rev. Genet. 5:389-96 (2004)).

Figure 2:
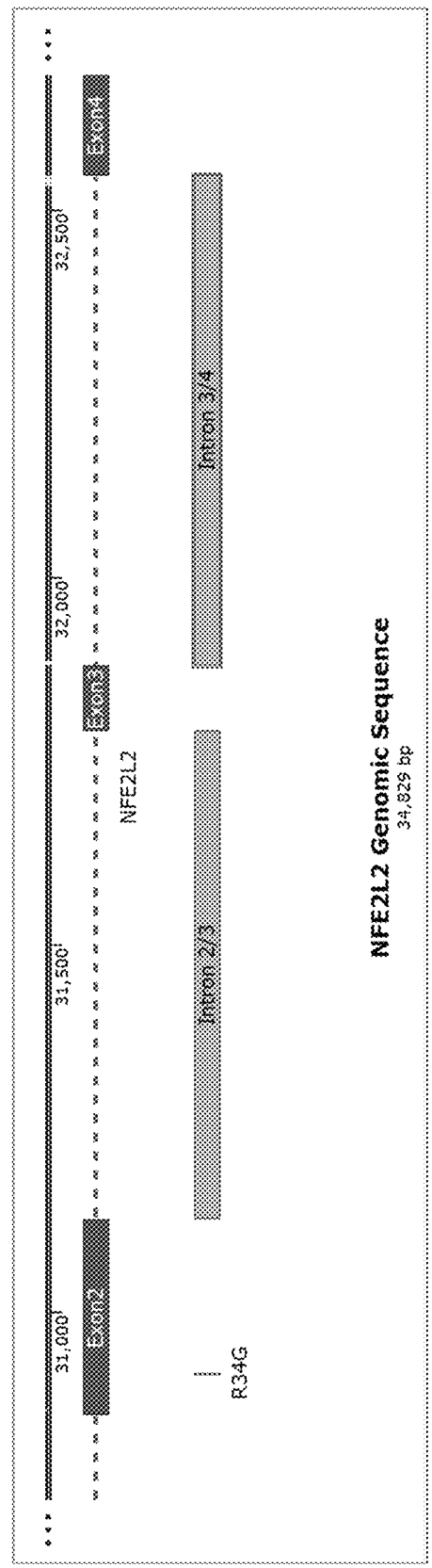

FIG. 2 shows part of the genomic structure of NFE2L2 gene. The NFE2L2 gene is composed of five exons with the R34G mutation occurring in exon 2. The Surekill guide RNAs were designed in the intron between exons 3 and 4 as indicated by the green box.

Figure 3:
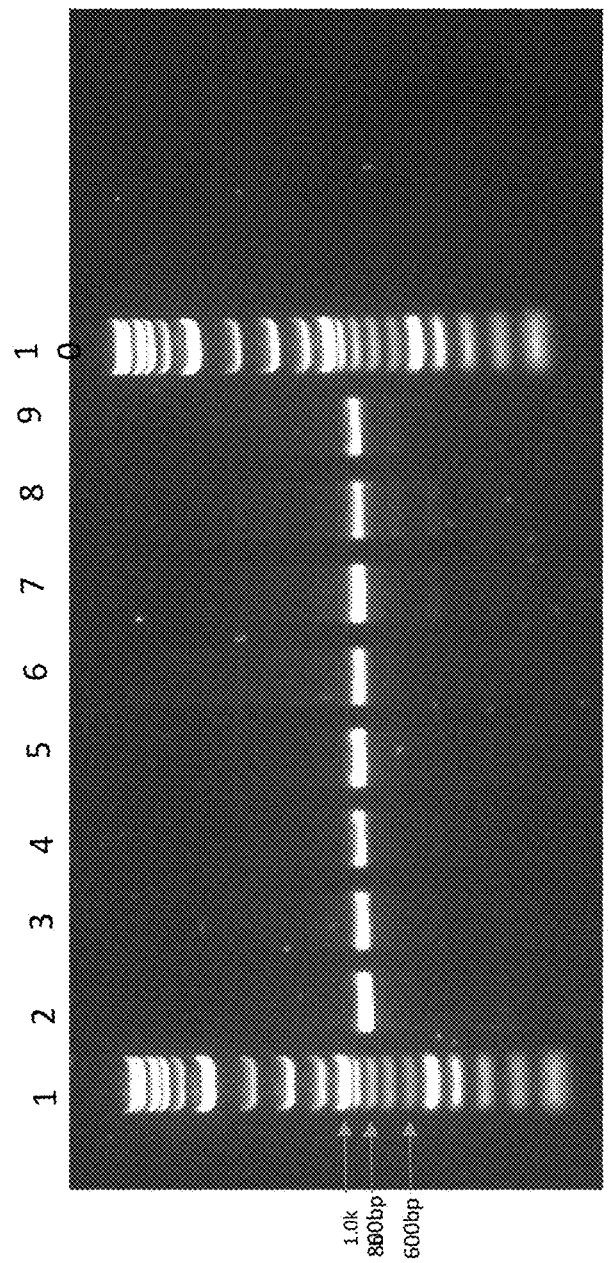

FIG. 3 shows no effect on NRF2 cDNAs by SureKill guide RNA alone. After CRISPR reactions, total RNA was prepared, and cDNA synthesized for PCR amplification of the target region from NRF2. PCR-amplified DNA was then analyzed by electrophoresis through a 1% agarose gel for 75 minutes at 80v. DNA was stained with SYBR Safe. Lanes 1 and 10: NEB 2 Log Ladder; Lane 2: Scrambled gRNA; Lane 3: NRF2 3-4 SureKill gRNA 3 alone; Lane 4: NRF2 3-4 SureKill gRNA 12 alone; Lane 5: NRF2 3-4 SureKill gRNA 14 alone; Lane 6: NRF2 3-4 SureKill gRNA 15 alone; Lane 7: NRF2 3-4 SureKill gRNA 21 alone; Lane 8: NRF2 3-4 SureKill gRNA 25 alone; Lane 9: NRF2 3-4 SureKill gRNA 26 alone. On the left side of the image are markers indicating DNA size in bp.

Figure 4:
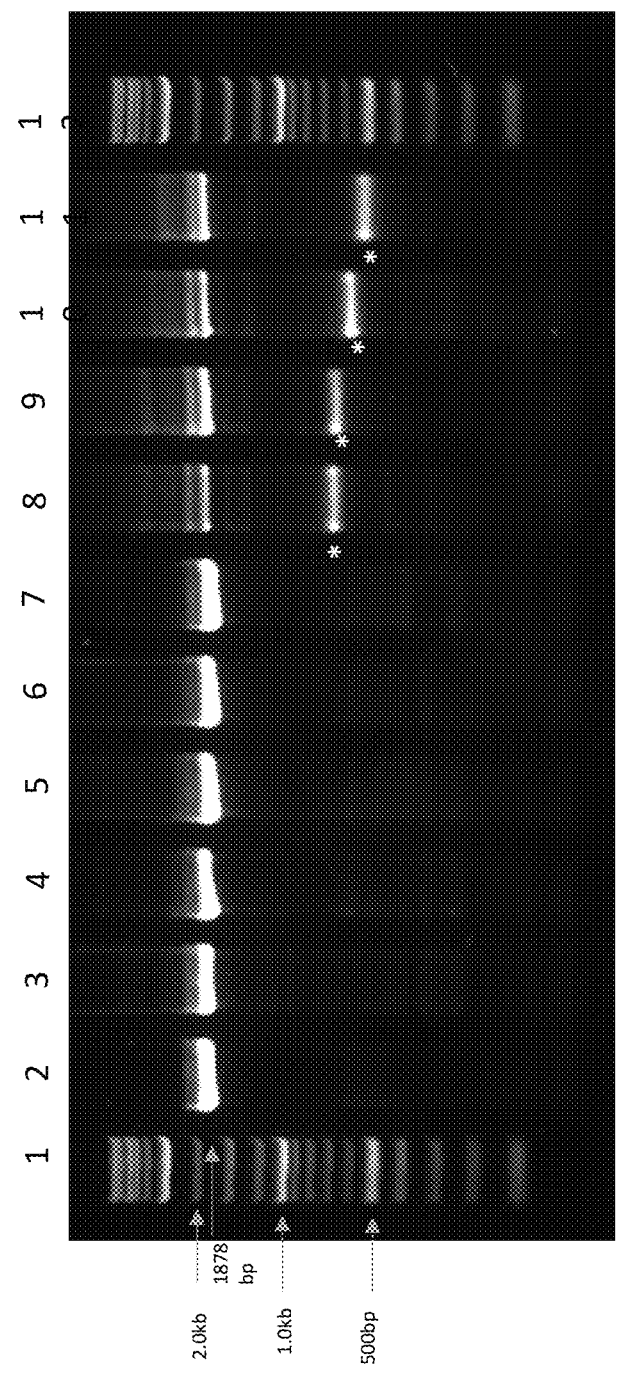

FIG. 4 shows the effect of SureKill approach on NRF2 gene at the genomic level. After CRISPR reactions, genomic DNA was prepared for PCR amplification of the target region from NRF2 gene. PCR-amplified DNA was then analyzed by electrophoresis through a 1% agarose gel for 75 minutes at 80v. DNA was stained with SYBR Safe. Lanes 1 and 12: NEB 2 Log Ladder; Lane 2: Scrambled gRNA; Lane 3: R34G gRNA alone; Lane 4: NRF2 3-4 SureKill gRNA 3 alone; Lane 5: NRF2 3-4 SureKill gRNA 12 alone; Lane 6: NRF2 3-4 SureKill gRNA 14 alone; Lane 7: NRF2 3-4 SureKill gRNA 15 alone; Lane 8: NRF2 3-4 SureKill gRNA 3+R34G gRNA; Lane 9: NRF2 3-4 SureKill gRNA 12+R34G gRNA; Lane 10: NRF2 3-4 SureKill gRNA 14+R34G gRNA; Lane 11: NRF2 3-4 SureKill gRNA 15+R34G gRNA. On the left side of the image are markers indicating DNA size in bp. Expected dropout size for NRF2 3-4 SureKill gRNA 3+R34G gRNA: 676 bp. Expected dropout size for NRF2 3-4 SureKill gRNA 12+R34G gRNA: 658 bp. Expected dropout size for NRF2 3-4 SureKill gRNA 14+R34G gRNA: 582 bp. Expected dropout size for NRF2 3-4 SureKill gRNA 15+R34G gRNA: 515 bp. Dropout bands are indicated by asterisks.

Figure 5:
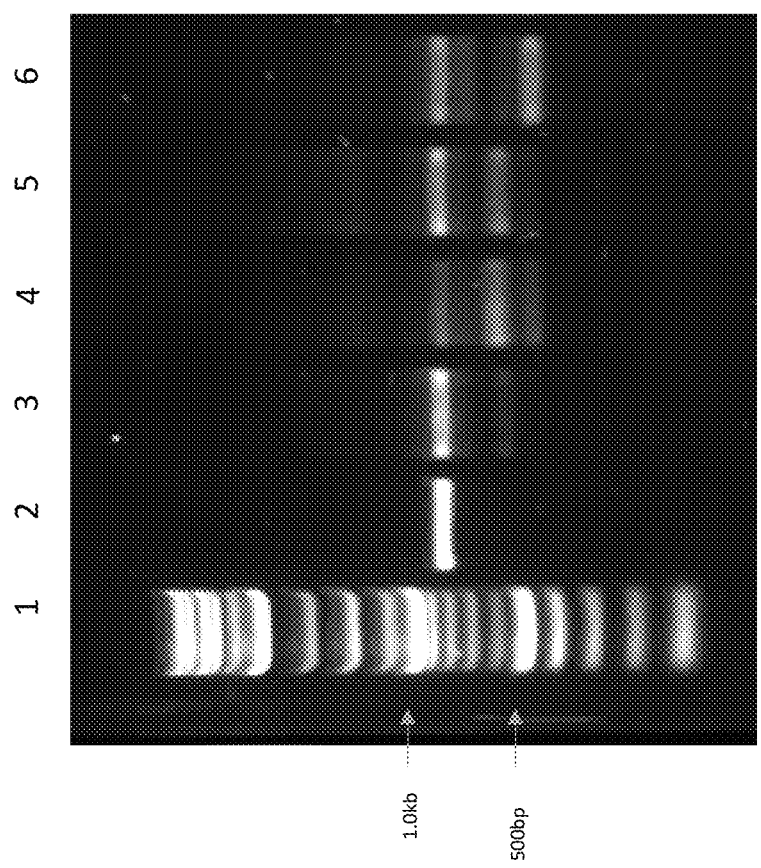

FIG. 5 shows decrease in wild type NRF2 cDNAs expression by SureKill approach. After CRISPR reactions, total RNA was prepared, and cDNA synthesized for PCR amplification of the target region from NRF2. PCR-amplified DNA was then analyzed by electrophoresis through a 1% agarose gel for 75 minutes at 80v. DNA was stained with SYBR Safe. Lane 1: NEB 2 Log Ladder; Lane 2: Scrambled gRNA; Lane 3: R34G gRNA alone; Lane 4: NRF2 3-4 SureKill gRNA 3+R34G gRNA; Lane 5: NRF2 3-4 SureKill gRNA+R34G gRNA; Lane 6: NRF2 3-4 SureKill gRNA 14+R34G gRNA.

Figure 6:
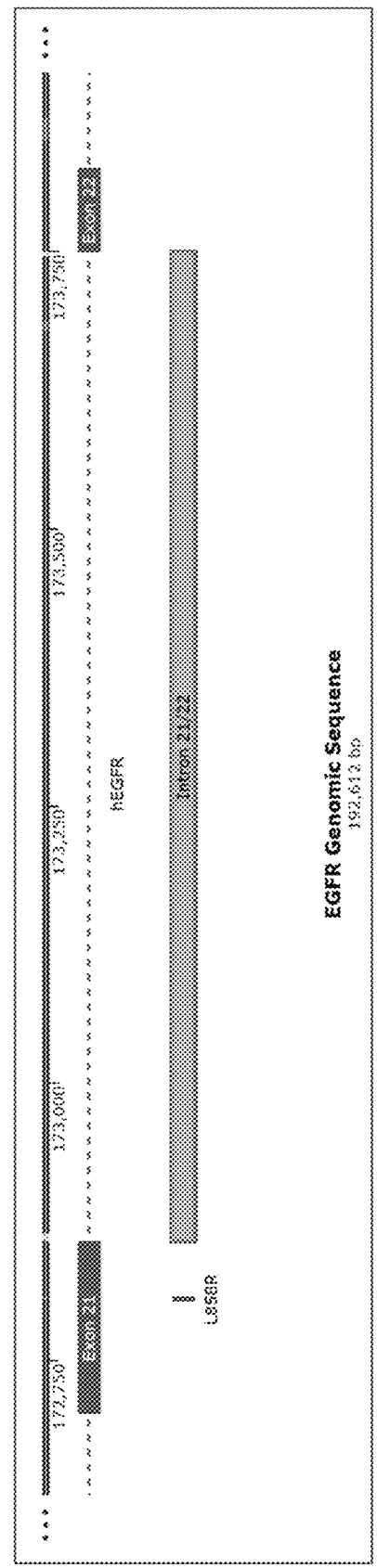

FIG. 6 shows part of the genomic structure of EGFR gene. The EGFR gene is composed of 28 exons with the L858R mutation occurring in exon 21. The Surekill guide RNAs were designed in the intron between exons 21 and 22 as indicated by the green box.

FIG. 7 shows no effect on EGFR cDNAs by SureKill guide RNA alone. After CRISPR reactions, total RNA was prepared, and cDNA synthesized for PCR amplification of the target region from EGFR. PCR-amplified DNA was then analyzed by electrophoresis through a 1% agarose gel for 75 minutes at 80v. DNA was stained with SYBR Safe. Lanes 1 and 13: NEB 2 Log Ladder; Lane 2: Scrambled gRNA; Lane 3: EGFR 21-22 SureKill gRNA 11 alone; Lane 4: EGFR 21-22 SureKill gRNA 13 alone; Lane 5: EGFR 21-22 SureKill gRNA 16 alone; Lane 6: EGFR 21-22 SureKill gRNA 17 alone; Lane 7: EGFR 21-22 SureKill gRNA 19 alone; Lane 8: EGFR 21-22 SureKill gRNA 22 alone; Lane 9: EGFR 21-22 SureKill gRNA 23 alone; Lane 10: EGFR 21-22 SureKill gRNA 27 alone; Lane 11: EGFR 21-22 SureKill gRNA 28 alone; Lane 12: EGFR 21-22 SureKill gRNA 29 alone. On the left side of the image are markers indicating DNA size in bp.

FIG. 8 shows the effect of SureKill approach on EGFR gene at the genomic level. After CRISPR reactions, genomic DNA was prepared for PCR amplification of the target region from EGFR gene. PCR-amplified DNA was then analyzed by electrophoresis through a 1% agarose gel for 75 minutes at 80v. DNA was stained with SYBR Safe. Lanes 1 and 10: NEB 2 Log Ladder; Lane 2: Scrambled gRNA; Lane 3: L858R gRNA alone; Lane 4: EGFR 21-22 SureKill gRNA 19 alone; Lane 5: EGFR 21-22 SureKill gRNA 27 alone; Lane 6: EGFR 21-22 SureKill gRNA 28+L858R gRNA; Lane 7: EGFR 21-22 SureKill gRNA 27+L858R gRNA; Lane 8: EGFR 21-22 SureKill gRNA 19+L858R gRNA; Lane 9: EGFR 21-22 SureKill gRNA 28 alone. On the left side of the image are markers indicating DNA size in bp. Expected dropout size of EGFR 21-22 SureKill gRNA 19+L858R gRNA: 316 bp. Expected dropout size of EGFR 21-22 SureKill gRNA 27+L858R gRNA: 417 bp. Expected dropout size of EGFR 21-22 SureKill gRNA 28+L858R gRNA: 463 bp. Dropout bands are indicated by asterisks.

FIG. 9 shows decrease in wild type EGFR cDNAs expression by SureKill approach. After CRISPR reactions, total RNA was prepared, and cDNA synthesized for semi-quantitative PCR amplification of the target region from EGFR. PCR amplification was performed for 25 cycles. PCR-amplified DNA was then analyzed by electrophoresis through a 1% agarose gel for 75 minutes at 80v. DNA was stained with SYBR Safe. Lanes 1 and 10: NEB 2 Log Ladder; Lane 2: Scrambled gRNA; Lane 3: L858R gRNA alone; Lane 4: EGFR 21-22 SureKill gRNA 19 alone; Lane 5: EGFR 21-22 SureKill gRNA 27 alone; Lane 6: EGFR 21-22 SureKill gRNA 28 alone; Lane 7: EGFR 21-22 SureKill gRNA 19+L858R gRNA; Lane 8: EGFR 21-22 SureKill gRNA 27+L858R gRNA; Lane 9: EGFR 21-22 SureKill gRNA 28+L858R gRNA. On the left side of the image are markers indicating DNA size in bp. Each lanes was loaded equally.

DETAILED DESCRIPTION

Figure 1:
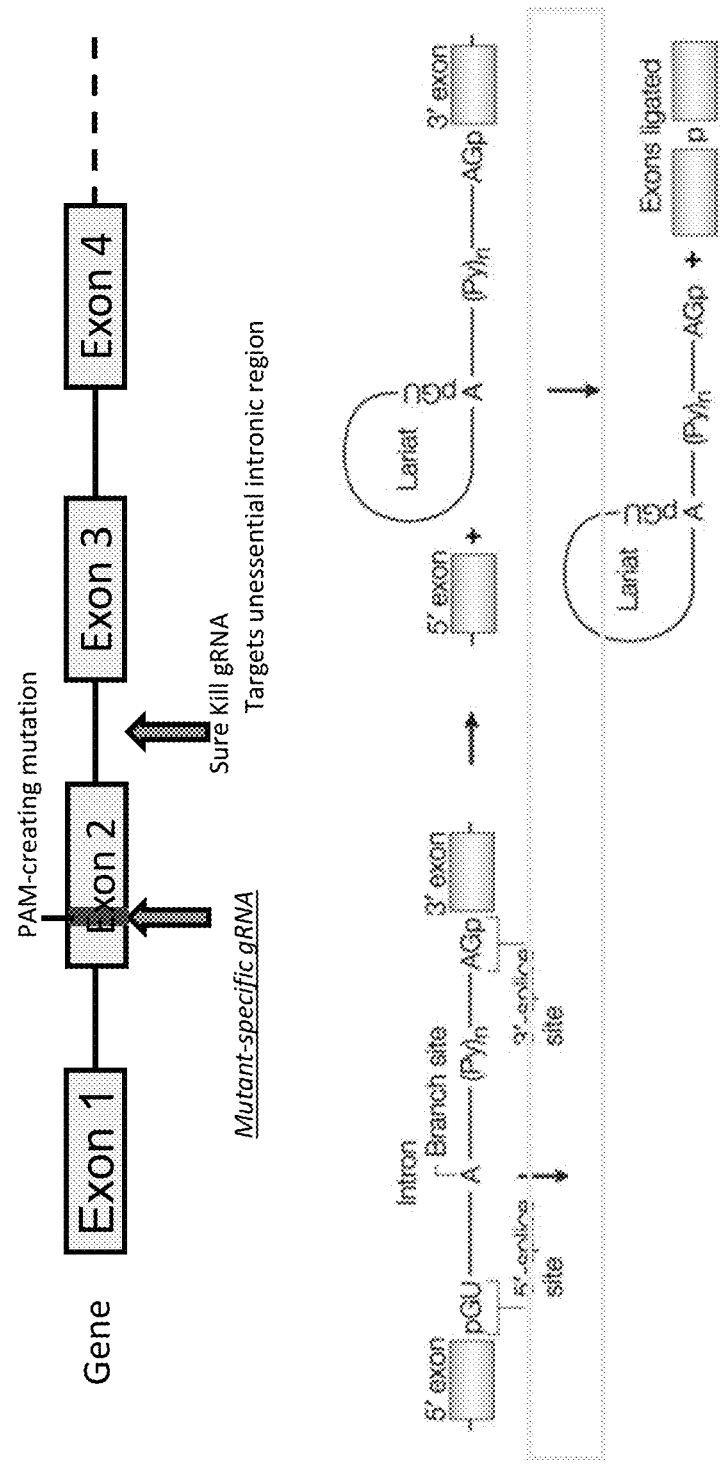
FIG. 1 shows a schematic representation of presently disclosed method. Top panel shows a hypothetical gene with exons (boxed) and introns (black lines). Vertical bar in Exon 2 indicates a PAM creating mutation. gRNAs are indicated by thick arrows.

Applicants have solved the stated problem. CRISPR/Cas9 has great potential as a tool for use in gene therapy. One of the key advantages of the technology is its ability to specifically bind to a given genomic sequence with high precision and induce double-stranded breaks, resulting in frame-shifting indels that can lead to a knockout. This advantage can be leveraged in a clinical setting with the intent of disabling a mutated gene that results in a pathological condition, such as a cancer-driving somatic mutation, by designing the guide RNA (gRNA) to target the mutant sequence. However, not every CRISPR/Cas9 will act on its intended target sequence with high efficiency. To overcome this limitation, Applicants have developed a novel approach using two gRNAs, with one gRNA specifically targeting the mutated sequence and the second gRNA targeting an intronic sequence in a region of low consequence (an example of which is shown in FIG. 1 (schematic) and FIGS. 4 and 8 (showing actual SureKill approach)). The action of both gRNAs acting in concert will induce exon skipping as a result of deleting the genomic DNA between the two Cas9 cut sites, effectively disabling the production of functional pathogenic protein. In a clinical setting, a systemic delivery of these two gRNAs would allow for the tumor cells harboring the driver mutation to be effectively disabled via exon skipping while healthy cells will be left unaffected as they lack the driver mutation.

Applicants specifically incorporate the entire contents of all cited references in this disclosure. Further, when an amount, concentration, or other value or parameter is given as either a range or a list of upper values and lower values, this is to be understood as specifically disclosing all ranges formed from any pair of any upper range limit or value and any lower range limit or value, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

Definitions

In this disclosure, a number of terms and abbreviations are used. The following definitions are provided.

As used herein, the term "about" or "approximately" means within 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or less of a given value or range.

The term "comprising" is intended to include embodiments encompassed by the terms "consisting essentially of" and "consisting of". Similarly, the term "consisting essentially of" is intended to include embodiments encompassed by the term "consisting of".

The indefinite articles "a" and "an", as used herein in the specification and in the claims, unless clearly indicated to the contrary, should be understood to mean "at least one".

The phrase "and/or", as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those lements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of", or, when used in the claims, "consisting of", will refer to the inclusion of exactly one element of a number or list of elements. In general, the term "or" as used herein shall only be interpreted as indicating exclusive alternatives (i.e., "one or the other but not both") when preceded by terms of exclusivity, "either", "one of", "only one of", "exactly one of". "Consisting essentially of", when used in the claims, shall have its ordinary meaning as used in the field of patent law.

An "endonuclease" an enzyme that cleaves the phosphodiester bond within a polynucleotide chain. In some embodiments, an endonuclease generates a double-stranded break at a desired position in the genome, and in some embodiments, an endonuclease generates a single-stranded break or a "nick" or break on one strand of the DNA phosphate sugar backbone at a desired position in the genome, and in some embodiments, without producing undesired off-target DNA stranded breaks. Endonuclease can be naturally occurring endonuclease or it can be artificially generated.

A "Clustered Regularly Interspaced Short Palindromic Repeat (CRISPR)-associated endonuclease protein-binding domain" or "Cas binding domain" refers to a nucleic acid element or domain within a nucleic acid sequence or polynucleotide sequence that, in an effective amount, will bind or have an affinity for one or a plurality of CRISPR-associated endonuclease (or functional fragments thereof). In some embodiments, in the presence of the one or a plurality of proteins (or functional fragments thereof) and a target sequence, the one or plurality of proteins and the nucleic acid element forms a biologically active CRISPR complex and/or can be enzymatically active on a target sequence. In some embodiments, the CRISPR-associated endonuclease is a class 1 or class 2 CRISPR-associated endonuclease, and in some embodiments, a Cas9 or Cas12a endonuclease. The Cas9 endonuclease can have a nucleotide sequence identical to the wild type *Streptococcus pyogenes* sequence. In some embodiments, the CRISPR-associated endonuclease can be a sequence from other species, for example other *Streptococcus* species, such as *thermophilus; Pseudomonas aeruginosa, Escherichia coli*, or other sequenced bacteria genomes and archaea, or other prokaryotic microorganisms. Such species include: *Acidovorax avenae, Actinobacillus pleuropneumoniae, Actinobacillus succinogenes, Actinobacillus suis, Actinomyces* sp., *Alicycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gammaproteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus sp., Subdoligranulum* sp., *Tistrella mobilis, Treponema* sp., and *Verminephrobacter eiseniae* (or functional fragments or variants of any of the aforementioned sequences that have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to any of the aforementioned Cas9 endonucleases). In some embodiments, the CRISPR-associated endonuclease can be a Cas12a nuclease. The Cas12a nuclease can have a nucleotide sequence identical to a wild type *Prevotella, Francisella, Acidaminococcus, Proteocatella, Sulfurimonas, Elizabethkingia, Methylococcales, Moraxella, Helcococcus, Lachnospira, Limihaloglobus, Butyrivibrio, Methanomethylophilus, Coprococcus, Synergistes, Eubacterium, Roseburia, Bacteroidales, Ruminococcus, Eubacteriaceae, Leptospira, Parabacteriodes, Gracilibacteria, Lachnospiraceae, Clostridium, Brumimicrobium, Fibrobacter, Catenovulum, Acinetobacter, Flavobacterium, Succiniclasticum, Pseudobutyrivibrio, Barnesiella, Sneathia, Succinivibrionaceae, Treponema, Sedimentisphaera, Thiomicrospira, Eucomonympha, Arcobacter, Oribacterium, Methanoplasma, Porphyromonas, Succinovibrio*, or *Anaerovibrio* sequence (or functional fragments or variants of any of the aforementioned sequences that have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to any of the aforementioned Cas12a endonucleases). In some embodiments, the terms "(CRISPR)-associated endonuclease protein-binding domain" or "Cas binding domain" refer to a nucleic acid element or domain (e.g. and RNA element or domain) within a nucleic acid sequence that, in an effective amount, will bind to or have an affinity for one or a plurality of CRISPR-associated endonucleases (or functional fragments or variants thereof that are at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to a CRISPR-associated endonuclease). In some embodiments, the Cas binding domain consists of at least or no more than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or 250 nucleotides and comprises at least one sequence that is capable of forming a hairpin or duplex that partially associates or binds to a biologically active CRISPR-associated endonuclease at a concentration and within a microenvironment suitable for CRISPR system formation.

The "Clustered Regularly Interspaced Short Palindromic Repeats (CRISPR)-CRISPR associated (Cas) (CRISPR-Cas) system guide RNA" or "CRISPR-Cas system guide RNA" may comprise a transcription terminator domain. The term "transcription terminator domain" refers to a nucleic acid element or domain within a nucleic acid sequence (or polynucleotide sequence) that, in an effective amount, prevents bacterial transcription when the CRISPR complex is in a bacterial species and/or creates a secondary structure that stabilizes the association of the nucleic acid sequence to one or a plurality of Cas proteins (or functional fragments thereof) such that, in the presence of the one or a plurality of proteins (or functional fragments thereof), the one or plurality of Cas proteins and the nucleic acid element forms a biologically active CRISPR complex and/or can be enzymatically active on a target sequence in the presence of such a target sequence and a DNA-binding domain. In some embodiments, the transcription terminator domain consists of at least or no more than about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or 250 nucleotides and comprises at least one sequence that is capable of forming a hairpin or duplex that partially drives association of the nucleic acid sequence (sgRNA, crRNA with tracrRNA, or other nucleic acid sequence) to a biologically active CRISPR complex at a concentration and microenvironment suitable for CRISPR complex formation.

The term "DNA-binding domain" refers to a nucleic acid element or domain within a nucleic acid sequence (e.g. a guide RNA) that is complementary to a target sequence. In some embodiments, the DNA-binding domain will bind or have an affinity for a target sequence such that, in the presence of a biologically active CRISPR complex, one or plurality of Cas proteins can be enzymatically active on the target sequence. In some embodiments, the DNA binding domain comprises at least one sequence that is capable of forming Watson Crick basepairs with a target sequence as part of a biologically active CRISPR system at a concentration and microenvironment suitable for CRISPR system formation.

"CRISPR system" refers collectively to transcripts or synthetically produced transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a nucleic acid sequence to which a guide sequence is designed to have complementarity, where hybridization between a target sequence and a guide sequence promotes the formation of a CRISPR complex.

A target sequence may comprise any polynucleotide, such as DNA or RNA polynucleotides. In some embodiments, the target sequence is a DNA polynucleotide and is referred to a DNA target sequence. In some embodiments, a target sequence comprises at least three nucleic acid sequences that are recognized by a Cas-protein when the Cas protein is associated with a CRISPR complex or system which comprises at least one sgRNA or one tracrRNA/crRNA duplex at a concentration and within an microenvironment suitable for association of such a system. In some embodiments, the target DNA comprises at least one or more proto-spacer adjacent motifs which sequences are known in the art and are dependent upon the Cas protein system being used in conjunction with the sgRNA or crRNA/tracrRNAs employed by this work. In some embodiments, the target DNA comprises NNG, where G is an guanine and N is any naturally occurring nucleic acid. In some embodiments the target DNA comprises any one or combination of NNG, NNA, GAA, NGGNG, NGRRT, NGRRN, NNNNGATT, NNNNRYAC, NNAGAAW, TTTV, YG, TTTN, YTN, NGCG, NGAG, NGAN, NGNG, NG, NNGRRT, TYCV, TATV, or NAAAAC. In some embodiments, a target sequence is located in the nucleus or cytoplasm of a cell.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more base pairs from) the target sequence. Without wishing to be bound by theory, the tracr sequence, which may comprise or consist of all or a portion of a wild-type tracr sequence (e.g., about or more than about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional (bind the Cas protein or functional fragment thereof). In some embodiments, the tracr sequence has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of sequence complementarity along the length of the tracr mate sequence when optimally aligned. In some embodiments, one or more vectors driving expression of one or more elements of a CRISPR system are introduced into a host cell such that the presence and/or expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. With at least some of the modification contemplated by this disclosure, in some embodiments, the guide sequence or RNA or DNA sequences that form a CRISPR complex are at least partially synthetic. The CRISPR system elements that are combined in a single vector may be arranged in any suitable orientation, such as one element located 5' with respect to ("upstream" of) or 3' with respect to ("downstream" of) a second element. In some embodiments, the disclosure relates to a composition comprising a chemically synthesized guide sequence. In some embodiments, the chemically synthesized guide sequence is used in conjunction with a vector comprising a coding sequence that encodes a CRISPR enzyme, such as a class 2 Cas9 or Cas12a protein. In some embodiments, the chemically synthesized guide sequence is used in conjunction with one or more vectors, wherein each vector comprises a coding sequence that encodes a CRISPR enzyme, such as a class 2 Cas9 or Cas12a protein. The coding sequence of one element may be located on the same or opposite strand of the coding sequence of a second element, and oriented in the same or opposite direction. In some embodiments, a single promoter drives expression of a transcript encoding a CRISPR enzyme and one or more additional (second, third, fourth, etc.) guide sequences, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, one or more additional guide sequence, tracr mate sequence, and tracr sequence are each a component of different nucleic acid sequences. For instance, in the case of a tracr and tracr mate sequences and in some embodiments, the disclosure relates to a composition comprising at least a first and second nucleic acid sequence, wherein the first nucleic acid sequence comprises a tracr sequence and the second nucleic acid sequence comprises a tracr mate sequence, wherein the first nucleic acid sequence is at least partially complementary to the second nucleic acid sequence such that the first and second nucleic acid for a duplex and wherein the first nucleic acid and the second nucleic acid either individually or collectively comprise a DNA-targeting domain, a Cas protein binding domain, and a transcription terminator domain. In some embodiments, the CRISPR enzyme, one or more additional guide sequence, tracr mate sequence, and tracr sequence are operably linked to and expressed from the same promoter. In some embodiments, the disclosure relates to compositions comprising any one or combination of the disclosed domains on one guide sequence or two separate tracrRNA/crRNA sequences with or without any of the disclosed modifications. Any methods disclosed herein also relate to the use of tracrRNA/crRNA sequence interchangeably with the use of a guide sequence, such that a composition may comprise a single synthetic guide sequence and/or a synthetic tracrRNA/crRNA with any one or combination of modified domains disclosed herein.

In some embodiments, a guide RNA can be a short, synthetic, chimeric tracrRNA/crRNA (a "single-guide RNA" or "sgRNA"). A guide RNA may also comprise two short, synthetic tracrRNA/crRNAs (a "dual-guide RNA" or "dgRNA").

As used herein, the term "homologous" or "homologue" or "ortholog" refers to related sequences that share a common ancestor or family member and are determined based on the degree of sequence identity. The terms "homology", "homologous", "substantially similar", and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. In some embodiments, these terms describe the relationship between a gene found in one species, subspecies, variety, cultivar, or strain and the corresponding or equivalent gene in another species, subspecies, variety, cultivar or strain. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania), AlignX (Vector NTI, Invitrogen, Carlsbad, Calif.), and Sequencher (Gene Codes, Ann Arbor, Mich.).

"Recombination" refers to a process of exchange of genetic information between two polynucleotides, including but not limited to, donor capture by NHEJ and HDR.

The term "double-strand break", "DSB", or "double-strand cut" refers to the severing or cleavage of both strands of the DNA double helix. The DSB may result in cleavage of both stands at the same position leading to "blunt ends" or staggered cleavage resulting in a region of single-stranded DNA at the end of each DNA fragment, or "sticky ends". A DSB may arise from the action of one or more DNA nucleases.

By "hybridizable", "complementary", or "substantially complementary" it is meant that a nucleic acid (e.g., RNA, DNA) comprises a sequence of nucleotides that enables it to non-covalently bind, i.e., form Watson-Crick base pairs and/or G/U base pairs, "anneal", or "hybridize", to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C). In addition, for hybridization between two RNA molecules (e.g., dsRNA), and for hybridization of a DNA molecule with an RNA molecule (e.g., when a ssRNA target nucleic acid base pairs with a DNA PAMmer, when a DNA target nucleic acid base pairs with an RNA guide nucleic acid, etc.): guanine (G) can also base pair with uracil (U). For example, G/U base-pairing is partially responsible for the degeneracy (i.e., redundancy) of the genetic code in the context of tRNA anti-codon base-pairing with codons in mRNA. Thus, a guanine (G) (e.g., of a protein-binding segment (dsRNA duplex) of a subject guide nucleic acid molecule, of a target nucleic acid base pairing with a guide nucleic acid, and/or a PAMmer, etc.) is considered complementary to both a uracil (U) and to an adenine (A). For example, when a G/U base-pair can be made at a given nucleotide position of a protein-binding segment (e.g., dsRNA duplex) of a subject guide nucleic acid molecule, the position is not considered to be non-complementary, but is instead considered to be complementary.

Hybridization and washing conditions are well known and exemplified in Sambrook J., Fritsch. E. F. and Maniatis, T. Molecular Cloning: A Laboratory Manual, Second Edition. Cold Spring Harbor Laboratory Press. Cold Spring Harbor (1989), particularly Chapter 11 and Table 11.1 therein; and Sambrook. J. and Russell, W., Molecular Cloning: A Laboratory Manual, Third Edition. Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g., complementarity over 35, 34, 33, 32, 31, 30, 29, 28, 27, 26, 25, 24, 23, 22, 21, 20, 19, 18 or less nucleotides), the position of mismatches can become important (see Sambrook et al., supra, 11.7-11.8). Typically, the length for a hybridizable nucleic acid is 8 nucleotides or more (e.g., 10, 11, 12, 13, 14, 15, 16, 17, 18, 19, 20, 21, 22, 23, 24, 25, 26, 27, 28, 29, 30 nucleotides or more). The temperature and wash solution salt concentration may be adjusted as necessary according to factors such as length of the region of complementation and the degree of complementation.

Examples of stringent hybridization conditions include: incubation temperatures of about 25° C., 26° C., 27° C., 28° C., 29° C., 30° C., 31° C., 32° C., 33° C., 34° C., 35° C., 36° C., or 37° C.; hybridization buffer concentrations of about 6× SSC, 7× SSC, 8× SSC, 9× SSC, or 10× SSC; formamide concentrations of about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%; and wash solutions from about 4× SSC, 5× SSC, 6× SSC, 7× SSC, to 8× SSC. Examples of moderate hybridization conditions include: incubation temperatures of about 40° C., 41° C., 42° C., 43° C., 44° C., 45° C., 46° C., 47° C., 48° C., 49° C., or 50° C.; buffer concentrations of about 9× SSC, 8× SSC, 7× SSC, 6× SSC, 5× SSC, 4× SSC, 3× SSC, or 2× SSC; formamide concentrations of about 30%, 31%, 32%, 33%, 34%, 35%, 36%, 37%, 38%, 39%, 40%, 41%, 42%, 43%, 44%, 45%, 46%, 47%, 48%, 49%, or 50%; and wash solutions of about 5× SSC, 4× SSC, 3× SSC, or 2× SSC. Examples of high stringency conditions include: incubation temperatures of about 55%, 56%, 57%, 58%, 59%, 60%, 61%, 62%, 63%, 64%, 65%, 66%, 67%, or 68%; buffer concentrations of about 1× SSC, 0.95× SSC, 0.9× SSC, 0.85× SSC, 0.8× SSC, 0.75× SSC, 0.7× SSC, 0.65× SSC, 0.6× SSC, 0.55× SSC, 0.5× SSC, 0.45× SSC, 0.4× SSC, 0.35× SSC, 0.3× SSC, 0.25× SSC, 0.2× SSC, 0.15× SSC, or 0.1× SSC; formamide concentrations of about 55%, 56%, 57%, 58%, 59%, 60%, 61%, 62%, 63%, 64%, 65%, 66%, 67%, 68%, 69%, 70%, 71%, 72%, 73%, 74%, or 75%; and wash solutions of about 1× SSC, 0.95× SSC, 0.9× SSC, 0.85× SSC, 0.8× SSC, 0.75× SSC, 0.7× SSC, 0.65× SSC, 0.6× SSC, 0.55× SSC, 0.5× SSC, 0.45× SSC, 0.4× SSC, 0.35× SSC, 0.3× SSC, 0.25× SSC, 0.2× SSC, 0.15× SSC, or 0.1× SSC, or deionized water. In general, hybridization incubation times are from 5 minutes to 24 hours, with 1, 2, or more washing steps, and wash incubation times are about 1, 2, 3, 4, 5, 6, 7, 8, 9, 10, 11, 12, 13, 14, 15 minutes or more. It is understood that equivalents of SSC using other buffer systems can be employed.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% (i.e., full complementarity) sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90% complementarity. In this example, the remaining non-complementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Exemplary methods include BLAST programs (basic local alignment search tools) and PowerBLAST programs (Altschul et al., J. Mol. Biol. 215: 403-10 (1990); Zhang et al., Genome Res., 7:649-56 (1997)) or by using the Gap program (Wisconsin Sequence Analysis Package, Version 8 for Unix, Genetics Computer Group, University Research Park, Madison Wis.), using default settings, which uses the algorithm of Smith et al. (Adv. Appl. Math. 2:482-89 (1981)).

As used herein, a "variant", "mutant", or "mutated" polynucleotide contains at least one polynucleotide sequence alteration as compared to the polynucleotide sequence of the corresponding wild-type or parent polynucleotide.

As used herein, the terms "treat," "treating" or "treatment" refer to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) of the state of disease, amelioration or palliation of the disease state, diminishing rate of or time to progression, and remission (whether partial or total). "Treatment" of a cancer can also mean prolonging survival as compared to expected survival in the absence of treatment. Treatment need not be curative. In certain embodiments, treatment includes one or more of a decrease in pain or an increase in the quality of life (QOL) as judged by a qualified individual, e.g., a treating physician, e.g., using accepted assessment tools of pain and QOL. In certain embodiments, a decrease in pain or an increase in the QOL as judged by a qualified individual, e.g., a treating physician, e.g., using accepted assessment tools of pain and QOL is not considered to be a "treatment" of the cancer.

"Chemotherapeutic agent" refers to a drug used for the treatment of cancer. Chemotherapeutic agents include, but are not limited to, small molecules, hormones and hormone analogs, and biologics (e.g., antibodies, peptide drugs, nucleic acid drugs). In certain embodiments, chemotherapy does not include hormones and hormone analogs.

A "cancer that is resistant to one or more chemotherapeutic agents" is a cancer that does not respond, or ceases to respond to treatment with a chemotherapeutic regimen, i.e., does not achieve at least stable disease (i.e., stable disease, partial response, or complete response) in the target lesion either during or after completion of the chemotherapeutic regimen. Resistance to one or more chemotherapeutic agents results in, e.g., tumor growth, increased tumor burden, and/or tumor metastasis.

CRISPR/Endonucleases

CRISPR/endonuclease (e.g., CRISPR/Cas9) systems are known in the art and are described, for example, in U.S. Pat. No. 9,925,248, which is incorporated by reference herein in its entirety. CRISPR-directed gene editing can identify and execute DNA cleavage at specific sites within the chromosome at a surprisingly high efficiency and precision. The natural activity of CRISPR/Cas9 is to disable a viral genome infecting a bacterial cell. Subsequent genetic reengineering of CRISPR/Cas function in human cells presents the possibility of disabling human genes at a significant frequency.

In bacteria, the CRISPR/Cas loci encode RNA-guided adaptive immune systems against mobile genetic elements (viruses, transposable elements and conjugative plasmids). Three types (I-III) of CRISPR systems have been identified. CRISPR clusters contain spacers, the sequences complementary to antecedent mobile elements. CRISPR clusters are transcribed and processed into mature CRISPR (Clustered Regularly Interspaced Short Palindromic Repeats) RNA (crRNA) containing a DNA binding region (spacer) which is complementary to the target gene.

The compositions described herein can include a nucleic acid encoding a CRISPR-associated endonuclease. The CRISPR-associated endonuclease can be, e.g., a class 1 CRISPR-associated endonuclease or a class 2 CRISPR-associated endonuclease. Class 1 CRISPR-associated endonucleases include type I, type III, and type IV CRISPR-Cas systems, which have effector molecules that comprise multiple subunits. For class 1 CRISPR-associated endonucleases, effector molecules can include, in some embodiments, Cas7 (csm3, cmr1, cmr6) and Cas5 (csm4, csx10, cmr3), along with, in some embodiments, SS (Cas11) and Cas8a1; Cas8b1; Cas8c; Cas8u2 and Cas6; Cas3" and Cas10d; SS (Cas11), Cas8e, and Cas6; Cas8f and Cas6f; Cas6f; Cas8-like (Csf1); SS (Cas11) and Cas8-like (Csf1); or SS (Cas11) and Cas10. Class 1 CRISPR-associated endonucleases also be associated with, in some embodiments, target cleavage molecules, which can be Cas3 (type I) or Cas10 (type III) and spacer acquisition molecules such as, e.g., Cas1, Cas2, and/or Cas4. See, e.g., Koonin et al., Curr. Opin. Microbiol. 37:67-78 (2017); Strich et al., J. Clin. Microbiol. 57:1307-18 (2019); Liu et al., J. Biol. Chem. 295:14473-87 (2020).

Class 2 CRISPR-associated endonucleases include type I, type V, and type VI CRISPR-Cas systems, which have a single effector molecule. For class 2 CRISPR-associated endonucleases, effector molecules can include, in some embodiments, Cas9, Cas12a (cpf1), Cas12b1 (c2c1), Cas12b2, Cas12c (c2c3), Cas12d (CasY), Cas12e (CasX), Cas12f1 (Cas14a), Cas12f2 (Cas14b), Cas12f3 (Cas14c), Cas12g, Cas12h, Cas12i, Cas12k (c2c5), Cas13a (c2c2), Cas13b1 (c2c6), Cas13b2 (c2c6), Cas13c (c2c7), Cas13d, c2c4, c2c8, c2c9, and/or c2c10. See, e.g., Koonin et al., Curr. Opin. Microbiol. 37:67-78 (2017); Strich et al., J. Clin. Microbiol. 57:1307-18 (2019); Makarova et al., Nat. Rev. Microbiol. 18:67-83 (2020); Wang et al., J. Cell. Mol. Med. 24:3256-70 (2020).

In some embodiments, the CRISPR-associated endonuclease can be from *Acetobacter pasteurianus, Acetobacter persici, Acetobacter sp., Acetobacterium woodii, Acetohalobium arabaticum, Acholeplasma palmae, Acidaminococcus fermentans, Acidaminococcus intesini, Acidihalobacter ferrooxidans, Acidimicrobium ferrooxidans, Acidiphilium cryptum, Acidipropionibacterium acidipropionici, Acidithiobacillus caldus, Acidobacterium capsulatum, Acidothermus celluloyticus, Acidovorax avenae, Acidovorax sp., Acinetobacter baumannii, Acinetobacter haemolyticus, Acinetobacter junii, Acinetobacter soli, Acinetobacter sp., Actinoalloteichus hymeniacidonis, Actinoalloteichus sp., Actinobacillus equuli, Actinobacillus pleuropneumoniae, Actinobacillus succinogenes, Actinobacillus suis, Actinomyces meyeri, Actinomyces oris, Actinomyces sp., Actinoplanes missouriensis, Actinoplanes sp., Actinotignum schaalii, Aerococcus christensenii, Aerococcus sanguinicola, Aerococcus urinae, Aerococcus urinaeequi, Aerococcus urinaehominis, Aeromonas aquatica, Aeromonas media, Aeromonas veronii, Aeropyrum camini, Aggregatibacter actinomycetemcomitans, Aggregatibacter aphrophilus, Agrobacterium rhizogenes, Akkermansia glycaniphila, Akkermansia muciniphila, Alcanivorax dieselolei, Alicycliphilus dentrificans, Alicyclobacillus acidocaldarius, Aliivibrio wodanis, Alistipes shahii, Alkalilimnicola ehrlichei, Alkaliphilus metalliregidens, Alkaliphilus oremlandii, Allochromatium vinosum, Altermonas australica, Altermonas macleodii, Altermonas mediterranea, Altermonas sp., Aminobacterium colombiense, Ammonifex degensii, Amycolatopsis japonica, Amycolatopsis mediterranei, Amycolatopsis methanolica, Amycolatopsis orientalis, Anabaena cylindrica, Anabaena sp., Anabaena variabilis, Anaerobaculum mobile, Anaerocellum thermophilum, Anaerococcus mediteraneensis, Anaerolinea thermophila, Anaerolineaeacea bacterium, Anaeromyxobacter dehalogenans, Anaeromyxobacter sp., Anaerostipes hadrus, Aneurinibacillus sp., Anoxybacillus amylolyticus, Anoxybacillus flavithermus, Anoxybacillus gonesis, Anoxybacillus sp., Aquaspirillum sp., Aquifex aeolicus, Arcanobacterium hamolyticum, Archangium gephyra, Arcobacter nitrofigilis, Arcobacter sp., Arthospira platensis, Azoarcus sp., Azospirillum brasilense, Azospirillum humicireducens, Azospirillum lipoferum, Azospirillum sp., Azotobacter chroococcum, Azotobacter vinelandii, Bacillus cereus, Bacillus clausii, Bacillus coagulans, Bacillus halodurans, Bacillus lehensis, Bacillus pumilus, Bacillus smithii, Bacillus thuringiensis, Bacillus tusciae, Bacteroidales bacterium, Bacteroides fragilis, Bacteroides helcogenes, Bacteroides sp., Barnesiella viscericola, Bartonella apis, Basilea psittacipulmonis, Bdellovibrio exovorus, Beggiatoa leptomitiformis, Belliella baltica, Bibersteinia trehalose, Bifidobacterium actinocoloniiforme, Bifidobacterium adolescentis, Bifidobacterium angulatum, Bifidobacterium animalis, Bifidobacterium bifidium, Bifidobacterium breve, Bifidobacterium catenulatum, Bifidobacterium dentum, Bifidobacterium kashiwanohense, Bifidobacterium longum, Bifidobacterium pseudocatenulatum, Bifidobacterium pseudolongum, Bifidobacterium thermophilum, Blastochloris viridis, Blastococcus saxobsidens, Bordetella pseudohinzii, Bosea sp., Brachyspira hyodsenteriae, Brachyspira murdochii, Burkholderia glumae, Burkholderia plantarii, Burkholderia sp., Burkholderiales bacterium, Butyrivibrio fibrisolvens, Caldicellulosiruptor hydrothermalis, Caldicellulosiruptor kristjanssonii, Caldicellulosiruptor lactoaceticus, Caldicellulosiruptor obsidiansis, Caldicellulosiruptor ownesensis, Caldicellulosiruptor saccharolyticus, Caldilinea aerophile, Caldimicrobium thiodismutans, Caldisericum exile, Calditerrivibrio nitroreducens, Caldithrix abyssi, Caldithrix sp., Campylobacter coli, Campylobacter curvus, Campylobacter fetus, Campylobacter gracilis, Campylobacter hominis, Campylobacter hyointestinalis, Campylobacter iguaniorum, Campylobacter jejuni, Campylobacter lari, Campylobacter peloridis, Campylobacter sp., Campylobacter subantarcticus, Capnocytophaga canimorsus, Capnocytophaga haemolytica, Capnocytophaga ochracea, Capnocytophaga sp., Castellaniella defragrans, Catenulispora acidiphila, Cedecea neteri, Cellulomonas fimi, Cellvibrio japonicus, Cellvibrio sp., Chamaesiphon minutus, Chania multitudinisentens, Chelatococcus daeguensis, Chelatococcus sp., Chlorobaculum limnaeum, Chlorobaculum parvum, Chlorobium chlorochromatii, Chlorobium limicola, Chlorobium phaeobacteriodes, Chlorobium tepidum, Chloroflexus*

*aggregans, Chloroflexus aurantiacus, Chloroflexus sp., Chloroherpton thalassium, Chondromyces crocatus, Chromobacterium vaccinii, Chromobacterium violaceum, Chromohalobacter salexigens, Chroococcidiopsis thermalis, Chryseobacterium gallinarum, Chryseobacterium indologenes, Chryseobacterium sp., Citrobacter koseri, Citrobacter rodentium, Clostridiodes difficile, Clostridium aceticum, Clostridium acidurici, Clostridium autoethanogenum, Clostridium baratii, Clostridium beijerinckii, Clostridium botulinum, Clostridium butyricum, Clostridium cellulyticum, Clostridium cellulovoransm, Clostridium* cf. *sacchrolyticum, Clostridium chauvoei, Clostridium clariflavum, Clostridium difficile, Clostridium formicaceticum, Clostridium kluyveri, Clostridium novyi, Clostridium pasteurianum, Clostridium perfringens, Clostridium saccharobutylicum, Clostridiumscatologenes, Clostridium* sp., *Clostridium sporogenes, Clostridium stercorarium, Clostridium tetani, Clostridium thermocellum, Clostridium tyrobutyricum, Comamonadaceae bacterium, Comamonas kersterii, Confluentimicrobium* sp., *Coprococcus catus, Coprococcus* sp., *Coprothermobacter proteolyticus, Corallococcus coralloides, Coriobacteriaceae bacterium, Coriobacterium glomerans, Corynebacterium aurimucosum, Corynebacterium camporealensis, Corynebacterium casei, Corynebacterium crudilactis, Corynebacterium deserti, Corynebacterium diptheriae, Corynebacterium efficiens, Corynebacterium falsenii, Corynebacterium flavescens, Corynebacterium frankenforstense, Corynebacterium glutamicum, Corynebacterium imitans, Corynebacterium jeikeium, Corynebacterium kutscheri, Corynebacterium lactis, Corynebacterium mustelae, Corynebacterium phocae, Corynebacterium pseudotuberculosis, Corynebacterium resistens, Corynebacterium simulans, Corynebacterium singulare, Corynebacterium* sp., *Corynebacterium sphenisci, Corynebacterium terpanotabidum, Corynebacterium testudinoris, Corynebacterium ulcerans, Corynebacterium urealyticum, Corynebacterium ureicelerivorans, Corynebacterium uterequi, Corynebacterium vitaeruminis, Crinalium epipsammum, Cronobacter dublinensis, Cronobacter malonaticus, Cronobacter muytjensii, Cronobacter sakazakii, Cronobacter turicensis, Cronobacter universalis, Cutibacterium avidum, Cyanobacterium stanieri, Cyanothece* sp., *Cycloclasticus zancles, Cylindrospermum stagnale, Deferribacter desulfuricans, Defluviimonas alba, Defluvitoga tunisiensis, Dehalococcoides mccartyi, Dehalococcoides* sp., *Deinococcus geothermalis, Deinococcus gobiensis, Deinococcus proteolyticus, Delftia acidovorans, Delftia* sp., *Delftia tsuruhatensis, Desulfarculus baarsii, Desulfatibacillum alkeniovrans, Desulfitobacterium autotrophicum, Desulfitobacterium dehalogenans, Desulfitobacterium haniense, Desulfobacca acetoxidans, Desulfobacula toluolica, Desulfobulbus propionicus, Desulfocapsa sulfexigens, Desulfococcus multivorans, Desulfohalobium retbaense, Desulfohalobium orale, Desulfomonile tiedjei, Delsulfosporoinus acidiphilus, Delsulfosporoinus orientis, Desulfotalea psychrophila, Desulfotomaculum acetoxidans, Desulfotomaculum carboxydivorans, Desulfotomaculum ferrireducens, Desulfotomaculum gibsoniae, Desulfotomaculum kuznetsovii, Desulfotomaculum reducens, Desulfotomaculum ruminis, Desulfovibro desulfuricans, Desulfovibro gigas, Desulfovibro hydrothermalis, Desulfovibro magneticus, Desulfovibro piger, Desulfovibro* sp., *Desulfovibro vulgaris, Desulfurispirillum indicum, Desulfurivibrio alkaliphilus, Desulfurobacterium thermolithotrophum, Desulfuromonas sp., Dialister pneumosintes, Diaphorobacter* sp., *Dichelobacter nodosus, Dickeya dadantii, Dickeya solani, Dickeya zeae, Dictyoglomus thermophilum, Dictyoglomus turgidum, Dinoroseobacter shibae, Dokdonella koreensis, Edwardsiella hoshinae, Edwardsiella piscicida, Edwardsiella* sp., *Eggerthella lenta, Eggerthella* sp., *Elizabethkingia anopheles, Elizabethkingia meningoseptica, Elizabethkingia miricola, Elusimicrobium minutum, Endomicrobium proavitum, Enterobacter cloacae, Enterobacter hormaechei, Enterobacter kobei, Enterobacter sakazakii, Enterobacter* sp., *Enterobacteriaceae bacterium, Enterococcus durans, Enterococcus faecalis, Enterococcus faecium, Enterococcus gallinarum, Enterococcus hirae, Enterococcus* sp., *Erwinia amylovora, Erwinia carotovora, Erwinia pyrifoliae, Erwinia* sp., *Erwinia tasmaniensis, Escherichia blattae, Escherichia coli, Escherichia fergusonii, Ethanoligenens harbinense, Eubacterium eligens, Eubacterium limosum, Eubacterium rectale, Eubacterium siraeum, Exiguobactierum sibiricum, Ezakiella massiliensis, Faecalibacterium prausnitzii, Faecalibaculum rodentium, Fermentimonas caenicola, Ferroplasma acidarmanus, Fervidobacterium islandicum, Fervidobacterium nodosum, Fervidobacterium pennivorans, Fibrobacter succinogenes, Filifactor alocis, Finegoldia magna, Fischerella* sp., *Flavobacterium branchiophilum, Flavobacterium columnare, Flavobacterium johnsoniae, Flavobacterium psychrophilum, Flavobacterium* sp., *Flexibacter litoralis, Flexistipes sinusarabici, Fluviicola taffensis, Francisella* cf. *novicida, Francisella hispaniensis, Francisella philomiragia, Francisella tularensis, Frankia alni, Frankia* sp., *Frankia* symbiont of *Datisca glomerata, Fuerstia marisgermanicae, Fusobacterium hwasookii, Fusobacterium nucleaturn, Gallibacterium anatis, γ proteobacterium* HdN1, *Gammaproteobacteria bacterium, Gardnerella vaginalis, Geitlerinema* sp., *Gemella* sp., *Geminocystis* sp., *Geoalkaibacter subterraneus, Geobacillus kaustophilus, Geobacillus* sp., *Geobacillus sterothermophilus, Geobacillus thermodenitrificans, Geobacter anodireducens, Geobacter lovleyi, Geobacter metallireducens, Geobacter pickeringii, Geobacter* sp., *Geobacter sulfurreducens, Geobacter uraniumreducens, Geosporobacter ferrireducens, Glaciecola* sp., *Gloeobacter kilaueensis, Gloeocapsa* sp., *Gluconacetobacter diazotrophicus, Gluconacetobacter xylinus, Gluconobacgter oxydans, Gordonia polyiosprenivorans, Gordonibacter pamelaeae, Granulibacter bethesdensis, Gynuella sunshinyii, Haematospirillum jordaniae, Haemophilus parainfluenzae, Hafnia alvei, Hahella chejuensis, Halanaerobium praevalens, Halanaerobium* sp., *Haliangium ochraceum, Haliscomenobacter hydrossis, Haloarcula hispancia, Halobacteroides halobios, Halocynthiibacter articus, Halomonas campaniensis, Halomonas elongate, Halomonas* sp., *Halorbadus tiamatea, Halorhdospira halophila, Halotalea alkalilenta, Halothece* sp., *Halothermothrix orenii, Halothiobacillus neapolitanus, Halothiobacillus* sp., *Helicobacter cetorum, Helicobacter cinaedi, Helicobacter mustelae, Helicobacter typhlonius, Heliobacterium modesticaldum, Herpetosiphon aurantiacus, Hydrogenobacter thermophilus, Hydrogenobaculum* sp., *Hymenobacter* sp., *Hyphomicrobium nitraivorans, lgnavibacteirum album, Ilyobacter polytropus, lsosphaera pallida, Janthinobactierum* sp., *Jeotgalibaca* sp., *Ketogulonicigenium vulgare, Ketogulonigenium vulgarum, Kibdelosporangium phytohabitans, Kirimatiella glycovorans, Kitasatospora setae, Klebsiella michiganensis, Klebsiella oxytoca, Klebsiella pneumoniae, Klebsiella variicola, Kluyvera intermedia, Kosakonia cowanii, Kosakonia oryzae, Kosmotoga olearia, Kuthia* sp., *Lachnoclostridium* sp., *Lactobacillus acidophilus, Lactobacillus amylophilus, Lactobacillus backii, Lactobacillus brevis, Lactobacillus buchneri, Lactobacillus casei, Lactobacillus crispatus, Lactobacillus cur-* vatus, Lactobacillus delbrueckii, Lactobacillus fermentum, Lactobacillus gallinarum, Lactobacillus heilongjiangensis, Lactobacillus helveticus, Lactobacillus jensenii, Lactobacillus johnsonii, Lactobacillus kefiranofaciens, Lactobacillus koreensis, Lactobacillus lindneri, Lactobacillus mucosae, Lactobacillus parabuchneri, Lactobacillus paracasei, Lactobacillus paracollinoides, Lactobacillus plantarum, Lactobacillus reuteri, Lactobacillus rhamnosus, Lactobacillus ruminis, Lactobacillus salivarius, Lactobacillus sanfranciscensis, Lactobacillus sp., Lawsonella clevelandensis, Leadbetterella byssophila, Leclercia adecarboxylata, Legionella pneumonphila, Lentzea guizhouensis, Leptolyngbya sp., Leptospira borgpetersenii, Leptospira interrogans, Leptospira santarosai, Leptospirillum sp., Leptothrix cholodnii, Leptotrichia buccalis, Leptotrichia sp., Leuconostoc gelidum, Limnochorda pilosa, Listeria innocua, Listeria ivanovii, Listeria monocytogenes, Listeria seeligeri, Luteipulveratus mongoliensis, Lutibacter sp., Lysinibacillus sphaericus, Lysobacter antibioticus, Lysobacter gummonsus, Magnetococcus sp., Magnetospira sp., Magnetospirillum sp., Mahella australiensis, Mannheimia haemolytica, Mannheimia sp., Mannheimia succiniciproducens, Mannheimia varigena, Maribacter sp., Marichromatium purpuratum, Marinilactibacillus sp., Marinithermus hydrothermalis, Marinitoga piezophila, Marinitoga sp., Marinobacter sp., Marinobacterium sp., Marinomonas mediterrenea, Marinomonas sp., Marinovum algicola, Martelella sp., Megamonas hypermegale, Megasphaera elsdenii, Meiothermus ruber, Meiothermus silvanus, Melioribacter roseus, Melissococcus plutonius, Mesotoga prima, Methanobacterium sp., Methylacidiphilum fumariolicum, Methylacidiphilum infernorum, Methylobacillus flagellatus, Methylobacterium aquaticum, Methylobacterium nodulans, Methylobacterium sp., Methylococcus capsulatus, Methylomicrobium alcaliphilum, Methylomonas denitrificans, Methylomonas methanica, Methylomonas sp., Methylophaga sp., Microbacterium sp., Microbulbifer thermotolerans, Microcoleus sp., Microcystis aeruginosa, Microcystis panniformis, Microlunatus phosphovorus, Mobiluncus curtisii, Moorella thermoacetica, Moraxella catarrhalis, Moraxella osloensis, Moraxella ovis, Mortella viscosa, Mucinivorans hirudinis, Muricauda lutaonensis, Mycobacterium africanum, Mycobacterium avium, Mycobacterium bovis, Mycobacterium canettii, Mycobacterium fortuitum, Mycobacterium kansasii, Mycobacterium marinum, Mycobacterium smegmatis, Mycobacterium sp., Mycobacterium tuberculosis, Mycobacterium yongonense, Mycoplasma arginini, Mycoplasma arthritidis, Mycoplasma canis, Mycoplasma cynos, Mycoplasma dispar, Mycoplasma gallisepticum, Mycoplasma mobile, Mycoplasma pneumoniae, Mycoplasma pullorum, Mycoplasma synoviae, Mycoplasma yeatsii, Myroides sp., Myxococcus fulvus, Myxococcus hansupus, Myxococcus stipitatus, Myxococcus xanthus, Nakamurella multipartite, Negativicoccus massiliensis, Neisseria elongata, Neisseria gonorrhoeae, Neisseria lactamica, Neisseria meningitidis, Neisseria weaveri, Niabella soli, Niastella koreensis, Nitratifractor salsuginis, Nitorbacter winogradskyi, Nitrosococcus halophilus, Nitrosococcus oceani, Nitrosococcus watsoni, Nitrosomonas communis, Nitrosomonas europaea, Nitrosomonas eutropha, Nitrosomonas sp., Nitrosomonas ureae, Nitrospira briensis, Nitrospira moscoviensis, Nocardia cyriacigeorgica, Nocardia farcinica, Nocardia nova, Nocardia soli, Nocardiopsis alba, Nocardiopsis dassonvillei, Nonlabens sp., Nostoc punctiforme, Nostoc sp., Novibacillus thermophilus, Obesumbacteirum proteus, Oblitomonas alkaliphila, Oceanithermus profundus, Odoribacter splanchnicus, Olsenella sp. Olsenella uli, Opitutaceae bacterium, Ornithobacterium rhinotracheale, Oscillatoria acuminata, Oscillatoria nigroviridis, Ottowia sp., Paenalcaligenes hominis, Paenibacillus beigingensis, Paenibacillus borealis, Paenibacillus durus, Paenibacillus larvae, Paenibacillus mucilaginosus, Paenibacillus napththalenovorans, Paenibacillus odorifer, Paenibacillus peoriae, Paenibacillus polymyxa, Paenibacillus sp., Paenibacillus stellifer, Paenibacillus terrae, Paenibacillus xylanexedens, Paludibacter propionicigenes, Paludisphaera borealis, Pannonibacter phragmitetus, Pantoea agglomerans, Pantoea sp., Parabacteroides distasonis, Paraburkholderia caribensis, Paraburkholderia xenovorans, Paracoccus aminophilus, Paracoccus denitrificans, Parageobacillus thermoglucosidans, Parascardovia denticolens, Parvibaculum lavamentivorans, Parimonas micra, Parvularcula bermudensis, Pasteurella multocida, Pectobacterium atrosepticum, Pectobacterium carotovorum, Pectobacterium parmentieri, Pectobacterium wasabiae, Pediococcus acidilactici, Pediococcus damnosus, Pediococcus pentosaceus, Pedobacter cryoconitis, Pedobacter sp., Pelagibaca abyssi, Pelobacter acetylenicus, Pelobacter carbinolicus, Pelobacter propionicus, Pelodictyon luteolum, Pelodictyon phaeoclathratiforme, Pelotomaculum thermopropionicum, Pelomaculum thermoporpionicum, Peptoclostridium acidaminophilum, Peptoniphilus sp., Perseponella marina, Persicobacter sp., Petrimonas mucoas, Petrotoga mobilis, Photobacterium profundum, Photorhabdus asymbiotica, Photorhabdus luminescens, Photorhabdus temperata, Phycisphaera mikurensis, Phycisphaerae bacterium, Planctomyces brasiliensis, Planctomyces limnophilus, Planococcus antarcticus, Pleurocapsa sp., Pluralibacter gergoviae, Polymorphum gilvum, Porphyromonas asaccharolytica, Porphyromonas gingivalis, Pragia fontium, Prevotella dentalis, Prevotella enoeca, Prevotella fusca, Prevotella intermedia, Prevotella ruminicola, Propionibacterium acidipropionici, Propionibacterium freudenreichii, Propionibacterium propionicum, Propionibacterium sp., Prostheocochloris aestuarii, Prostheocochloris sp., Prostheocochloris vibrioformis, Proteiniphilum saccharofermentans, Proteus mirabilis, Proteus vulgaris, Protochlamydia naegleriophila, Providencia rettgeri, Providencia stuartii, Pseudanabaena sp., Pseudoalteromonas luteoviolacea, Pseudoalteromonas rubra, Pseudoalteromonas translucida, Pseudomonas aeruginosa, Pseudomonas alcaliphila, Pseudomonas balearica, Pseudomonas chlororaphis, Pseudomonas cichorii, Pseudomonas citronellolis, Pseudomonas fulva, Pseudomonas mendocina, Pseudomonas parafulva, Pseudomonas pseudoalcaligenes, Pseudomonas sp., Pseudomonas stutzeri, Pseudonocardia sp., Pseudothermotoga hypogea, Pseudoxanthomonas spadix, Psychrobacter sp., Psychrobacter urativorans, Psychroflexus torquis, Psychromonas ingrahamii, Rahnella aquatilis, Rahnella sp., Ralstonia insidiosa, Ralstonia solanacearum, Ramlibacter tataouinensis, Raoultella omithinolytica, Rathayibacter toxicus, Rhodobacter capsulatus, Rhodobacter sphaeroides, Rhodoferax antarcticus, Rhodoferax ferrireducens, Rhodomicrobium vannielii, Rhodopseudomonas palustris, Rhodospirillum centenum, Rhodospirillum photometricum, Rhodospirillum rubrum, Rhodothermus marinus, Rhodovulum sulfidophilum, Riemerella anatipestifer, Rivularia sp., Roseburia hominis, Roseiflexus castenholzii, Roseiflexus sp., Rothia dentocariosa, Rothia mucilaginosa, Rubrivivax gelatinosus, Rubrobacter xylanophilus, Ruminiclostridium thermocellum, Ruminococcus albus, Runella slithyformis, Saccharopolyspora erythraea, Saccharothrix espanaensis, Salimicrobium jeotgali, Salinispora Arenicola, Salinispora tropica, Salmonella bongori,

*Salmonella enterica, Salmonella typhimurium, Sandaracinus amylolyticus, Saprospira grandis, Scardovia inopinata, Sebaldella termitidis, Sedimenticola thiotaurini, Sediminicola sp., Selenomonas ruminantium, Selenomonas sp., Selenomonas sputigena, Seonamhaeicola sp., Serinicoccus sp., Serratia fonticola, Serratia marcescens, Serratia plymuthica, Serratia sp., Shewanella baltica, Shewanella piezotolerans, Shewanella putrefaciens, Shewanella sp., Shewanella voilacea, Shigella boydii, Shigella dysenteriae, Shigella flexneri, Shigella sonnei, Shigella sp., Singulisphaera acidiphila, Sneathia amnii, Sorangium cellulosum, Sphaerobacter thermophilus, Sphaerochaeta pleomorpha, Sphingobium baderi, Sphingobium sp., Spirochaeta africana, Spirochaeta caldaria, Spirochaeta coccoides, Spirochaeta smaragdinae, Spirochaeta sp., Spirochaeta thermophila, Spiroplasma helicoides, Spirosoma aerolatum, Spirosoma linguale, Spirosoma montaniterrae, Spirosoma radiotolerans, Sporosarcina psychrophile, Stackebrandtia nassauensis, Stanieria cyanosphaera, Staphylococcus agnetis, Staphylococcus aureus, Staphylococcus epidermidis, Staphylococcus equorum, Staphylococcus hyicus, Staphylococcus lugdunensis, Staphylococcus pasteuri, Staphylococcus pseudintermedius, Staphylococcus schleiferi, Staphylococcus simulans, Stenotrophomonas acidaminiphila, Steroidobacter denitrificans, Streptobacillus moniliformis, Streptococcus agalactiae, Streptococcus angionsus, Streptococcus dysgalactiae, Streptococcus equi, Streptococcus gallolyticus, Streptococcus gordonii, Streptococcus halotolerans, Streptococcus infantarius, Streptococcus iniae, Streptococcus intermedius, Streptococcus lutetiensis, Streptococcus macedonicus, Streptococcus mutans, Streptococcus oralis, Streptococcus pantholopis, Streptococcus parasanguinis, Streptococcus pasteurianus, Streptococcus pyogenes, Streptococcus salivarius, Streptococcus sanguinis, Streptococcus sp., Streptococcus suis, Streptococcus thermophilus, Streptomyces albulus, Streptomyces albus, Streptomyces ambofaciens, Streptomyces autolyticus, Streptomyces avermitilis, Streptomyces bingchenggensis, Streptomyces cattleya, Streptomyces clavuligerus, Streptomyces cyaneogriseus, Streptomyces flavogriseus, Streptomyces glaucenscens, Streptomyces globisporus, Streptomyces griseochromogenes, Streptomyces griseus, Streptomyces hygroscopicus, Streptomyces leeuwenhoekii, Streptomyces lydicus, Streptomyces niveus, Streptomyces noursei, Streptomyces pactum, Streptomyces parvulus, Streptomyces rapamycinicus, Streptomyces reticuli, Streptomyces rubrolavendulae, Streptomyces sampsonii, Streptomyces silaceus, Streptomyces sp., Streptomyces venezuelae, Streptomyces vietnamensis, Streptomyces violaceusniger, Streptomyces xiamenensis, Sulfobacillus acidophilus, Sulfolobus acidocaldarius, Sulfurihydrogenibium azorense, Sulfurihydrogenibium sp., Sulfuritalea hydrogenivorans, Sulfurospirillum barnesii, Sulfurospirillum cavolei, Sulfurospirillum deleyianum, Sulfurospirillum multivorans, Sulfurovum lithotrophicum, Symbiobacterium thermophilum, Synechococcus sp., Synechocystis sp., Syntrophobacter fumaroxidans, Syntrophobotulus glycolicus, Syntrophomonas wolfei, Syntrophothermus lipocalidus, Syntrophus aciditrophicus, Tannerella forsythia, Tannerella sp., Taylorella asinigenitalis, Taylorella equigenitalis, Tenacibaculum dicentrarchi, Tepidanaerobacter acetatoxydans, Tepidanaerobacter sp., Teredinibacter turnerae, Tessaracoccus flavenscens, Tessaracoccus sp., Tetragenococcus halophilus, Thalassospira xiamenensis, Thauera chlorobenzoica, Thauera sp., Thermacetogenium phaeum, Thermaerobacter marianensis, Thermicola sp., Thermoanaerobacter brockii, Thermoanaerobacter italicus, Thermoanaerobacter kivui, Thermoanaerobacter mathranii, Thermoanaerobacter pseudethanolicus, Thermoanaerobacter sp., Thermoanaerobacter tengcongensis, Thermoanaerobacter wiegelii, Thermoanaerobacterium saccharolyticum, Thermoanaerobacterium thermosaccharolyticum, Thermoanaerobacterium xylanolyticum, Thermobacillus composti, Thermobaculum terrenum, Thermobifida fusca, Thermobispora bispora, Thermococcus litoralis, Thermocrinis albus, Thermocrinis ruber, Thermodesulfatator indicus, Thermodesulfobacterium commune, Thermodesulfobacterium sp., Thermodesulfobium narugense, Thermodesulfovibrio yellowstonii, Thermofilum sp., Thermomicrobium roseum, Thermomonospora curvata, Thermosediminibacter oceani, Thermosipho africanus, Thermosipho melanesiensis, Thermosipho sp., Thermosulfidibacter takaii, Thermosynechococcus sp., Thermotoga caldifontis, Thermotoga elfii, Thermotoga hypogea, Thermotoga lettingae, Thermotoga maritima, Thermotoga naphthophila, Thermotoga neapolitana, Thermotoga petrophila, Thermotoga profunda, Thermotoga sp., Thermotoga thermarum, Thermovibrio ammonificans, Thermovirga lienii, Thermus aquaticus, Thermus brockianus, Thermus oshimai, Thermus oshimai, Thermus parvatiensis, Thermus scotoductus, Thermus sp., Thermus thermophilus, Thioalkalimicrobium aerophilum, Thioalkalivibrio nitratireducens, Thioalkalivibrio paradoxus, Thioalkalivibrio sp., Thiocystis violascens, Thioflaviococcus mobilis, Thiolapillus brandeum, Thioploca ingrica, Tistrella mobilis, Tolumonas auensis, Treponema azotonutricium, Treponema brennaborense, Treponema pedis, Treponema primitia, Treponema putridum, Treponema succinifaciens, Trichodesmium erythraeum, Truepera radiovictrix, Trueperella pyogenes, Turicibacter sp.*, uncultured Termite group 1 bacterium, *Vagococcus penaei, Vagococcus teuberi, Veillonella parvula, Verminephrobacter eiseniae, Verrucomicrobia bacterium, Verrucomicrobium spinosum, Verrucosispora marls, Vibrio alginoyticus, Vibrio cholerae, Vibrio fluvialis, Vibrio harveyi, Vibrio natriegens, Vibrio parahaemolyticus, Vibrio vulnificus, Virgibacillus sp., Weeksella virosa, Winogradskyella sp., Woeseia oceani, Wolinella succinogenes, Xanthomonas albilineans, Xanthomonas axonopodis, Xanthomonas campestris, Xanthomonas citri, Xanthomonas fragariae, Xanthomonas oryzae, Xanthomonas translucens, Xanthomonas vescatoria, Xenorhabdus bovienii, Xenorhabdus doucetiae, Xenorhabdus nematophila, Xenorhabdus poinarii, Xylanimonas cellulosilytica, Yersinia frederiksenii, Yersinia kristensenii, Yersinia pestis, Yersinia pseudotuberculosis, Yersinia rohdei, Yersinia similis, Zhongshania aliphaticivorans, Zunongwangia profunda, Zymonas mobilis, Acidianus hospitalis, Acidilobus saccharovorans, Aciduliprofundum boonei, Aciduliprofundum sp., Aeropyrum pernix, Archaeoglobus fulgidus, Archaeoglobus sulfaticallidus, Archaeoglobus veneficus, Cuniculiplasma divulgatum, Desulfurococcus fermentans, Desulfurococcus kamchatkensis, Desulfurococcus mucosus, Ferroglobus placidus, Fervidicoccus fontis, Geoglobus acetivorans, Geoglobus ahangari, Halanaeroarchaeum sulfurireducens,* haloarchaeon HSR6, *Haloarcula hispanica, Haloarcula marismortui, Haloarcula sp., Halobacterium hubeiense, Halobacterium sp., Halobiforma lacisalsi, Haloferax gibbonsii, Haloferax mediterranei, Haloferax volcanii, Halogeometricum borinquense, Halolamina sediminis, Halomicrobium mukohataei,* halophilic archaeon DL31, *Haloquadratum walsbyi, Halorhabdus utahensis, Halorubrum lacusprofundi, Halostagnicola larsenii, Haloterrigena daqingensis, Hyperthermus butylicus, Ignicoccus hospitalis, Ignisphaera aggregans, Metallosphaera cuprina, Metallosphaera sedula, Methanobacterium formicicum, Methanobacterium sp.,*

Methanobrevibacter millerae, Methanobrevibacter olleyae, Methanobrevibacter ruminantium, Methanobrevibacter smithii, Methanobrevibacter sp., Methanocaldococcus bathoardescens, Methanocaldococcus fervens, Methanocaldococcus infernus, Methanocaldococcus jannaschii, Methanocaldococcus sp., Methanocaldococcus vulcanius, Methanocella paludicola, Methanocella sp., Methanococcoides burtonii, Methanococcoides methylutens, Methanococcus aeolicus, Methanococcus maripaludis, Methanococcus vannielii, Methanococcus voltae, Methanocorpusculum labreanum, Methanoculleus bourgensis, Methanoculleus marisnigri, Methanoculleus sp., methanogenic archaeon ISO4-H5, Methanolinea tarda, Methanomassiliicoccus sp., Methanomethylovorans hollandica, Methanopyrus kandleri, methanoregula formicicum, Methanosaeta concilii, Methanosaeta harundinacea, Methanosaeta thermophila, Methanosalsum zhilinae, Methanosarcina acetivorans, Methanosarcina barkeri, Methanosarcina horonobensis, Methanosarcina lacustris, Methanosarcina mazei, Methanosarcina siciliae, Methanosarcina sp., Methanosarcina thermophila, Methanosarcina vacuolate, Methanosphaera stadtmanae, Methanospirillum hungatei, Methanothermobacter marburgensis, Methanothermobacter sp., Methanothermobacter thermautotrophicus, Methanothermobacter wolfeii, Methanothermococcus okinawensis, Methanotorris igneus, Nanoarchaeum equitans, Natriabla magadii, Natrinema pellirubrum, Natrinema sp., Natronobacterium gregoryi, Natronococcus occultus, Natronomonas pharaonic, Nitrosopumilus maritimus, Paleococcus pacificus, Picrophilus torridus, Pyrobaculum aerophilum, Pyrobaculum arsenaticum, Pyrobaculum calidifontis, Pyrobaculum islandicum, Pyrobaculum oguniense, Pyrobaculum sp., Pyrococcus abyssi, Pyrococcus furiosus, Pyrococcus horikoshii, Pyrococcus sp., Pyrococcus yayanosii, Pyrodictium delaneyi, Pyrolobus fumarii, Staphylothermus hellenicus, Staphylothermus marinus, Sulfolobus acidocaldarius, Sulfolobus islandicus, Sulfolobus solfataricus, Sulfolobus sp., Sulfolobus tokodaii, Thermococcus barophilus, Thermococcus chitonophagus, Thermococcus eurythermalis, Thermococcus gammatolerans, Thermococcus kodakarensis, Thermococcus nautili, Thermococcus onnurineus, Thermococcus paralvinellae, Thermococcus peptonophilus, Thermococcus piezophilus, Thermococcus sibiricus, Thermococcus sp., Thermofilum carboxyditrophus, Thermofilum pendens, Thermofilum sp., Thermogladius sp., Thermoplasma acidophilum, Thermoplasma volcanium, Thermoproteus neutrophilus, Thermoproteus tenax, Thermosphaera aggregans, Vulcanisaeta distributa, or Vulcanisaeta moutnovskia.

In some embodiments, the CRISPR-associated endonuclease can be a Cas9 nuclease. The Cas9 nuclease can have a nucleotide sequence identical to the wild type *Streptococcus pyogenes* sequence. In some embodiments, the CRISPR-associated endonuclease can be a sequence from other species, for example other *Streptococcus* species, such as *thermophilus*; *Pseudomonas aeruginosa*, *Escherichia coli*, or other sequenced bacteria genomes and archaea, or other prokaryotic microorganisms. Such species include: *Acidovorax avenae, Actinobacillus pleuropneumoniae, Actinobacillus succinogenes, Actinobacillus suis, Actinomyces* sp., *Alicycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gammaproteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., and *Verminephrobacter eiseniae*.

Alternatively, the wild type *Streptococcus pyogenes* Cas9 sequence can be modified. The nucleic acid sequence can be codon optimized for efficient expression in mammalian cells, e.g., human cells. A Cas9 nuclease sequence codon optimized for expression in human cells sequence can be for example, the Cas9 nuclease sequence encoded by any of the expression vectors listed in Genbank accession numbers KM099231.1 GI:669193757; KM099232.1 GI:669193761; or KM099233.1 GI:669193765. Alternatively, the Cas9 nuclease sequence can be, for example, the sequence contained within a commercially available vector such as pX458, pX330 or pX260 from Addgene (Cambridge, Mass.). In some embodiments, the Cas9 endonuclease can have an amino acid sequence that is a variant or a fragment of any of the Cas9 endonuclease sequences of Genbank accession numbers KM099231.1 GI:669193757; KM099232.1 GI:669193761; or KM099233.1 GI:669193765 or Cas9 amino acid sequence of pX458, pX330 or pX260 (Addgene, Cambridge, Mass.). The Cas9 nucleotide sequence can be modified to encode biologically active variants of Cas9, and these variants can have or can include, for example, an amino acid sequence that differs from a wild type Cas9 by virtue of containing one or more, e.g., insertions, deletions, or mutations or a combination thereof. One or more of the mutations can be a substitution (e.g., a conservative amino acid substitution). For example, a biologically active variant of a Cas9 polypeptide can have an amino acid sequence with at least or about 50% sequence identity (e.g., at least or about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity) to a wild type Cas9 polypeptide.

In some embodiments, the CRISPR-associated endonuclease can be a Cas12a nuclease. The Cas12a nuclease can have a nucleotide sequence identical to a wild type *Prevotella* or *Francisella* sequence. Alternatively, a wild type *Prevotella* or *Francisella* Cas12a sequence can be modified. In some embodiments, an *Acidaminococcus, Proteocatella, Sulfurimonas, Elizabethkingia, Methylococcales, Moraxella, Helcococcus, Lachnospira, Limihaloglobus, Butyrivibrio, Methanomethylophilus, Coprococcus, Synergistes, Eubacterium, Roseburia, Bacteroidales, Ruminococcus, Eubacteriaceae, Leptospira, Parabacteriodes, Gracilibacteria, Lachnospiraceae, Clostridium, Bruminicrobium, Fibrobacter, Catenovulum, Acinetobacter, Flavobacterium, Succiniclasticum, Pseudobutyrivibro, Bamesiella,*

*Sneathia, Succinivibrionaceae, Treponema, Sedimentisphaera, Thiomicrospira, Eucomonympha, Arcobacter, Oribacterium, Methanoplasma, Porphyromonas, Succinovibrio,* or *Anaerovibrio* Cas12a sequence can be modified. The nucleic acid sequence can be codon optimized for efficient expression in mammalian cells, e.g., human cells. A Cas12a nuclease sequence codon optimized for expression in human cells sequence can be for example, the Cas9 nuclease sequence encoded by any of the expression vectors listed in Genbank accession numbers MF193599.1 GI: 1214941796, KY985374.1 GI: 1242863785, KY985375.1 GI: 1242863787, or KY985376.1 GI: 1242863789. Alternatively, the Cas12a nuclease sequence can be, for example, the sequence contained within a commercially available vector such as pAs-Cpf1 or pLb-Cpf1 from Addgene (Cambridge, Mass.). In some embodiments, the Cas12a endonuclease can have an amino acid sequence that is a variant or a fragment of any of the Cas12a endonuclease sequences of Genbank accession numbers MF193599.1 GI: 1214941796, KY985374.1 GI: 1242863785, KY985375.1 GI: 1242863787, or KY985376.1 GI: 1242863789 or Cas12a amino acid sequence of pAs-Cpf1 or pLb-Cpf1 (Addgene, Cambridge, Mass.). The Cas12a nucleotide sequence can be modified to encode biologically active variants of Cas12a, and these variants can have or can include, for example, an amino acid sequence that differs from a wild type Cas12a by virtue of containing one or more, e.g., insertions, deletions, or mutations or a combination thereof. One or more of the mutations can be a substitution (e.g., a conservative amino acid substitution). For example, a biologically active variant of a Cas12a polypeptide can have an amino acid sequence with at least or about 50% sequence identity (e.g., at least or about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity) to a wild type Cas12a polypeptide.

The compositions described herein may also include sequence encoding a guide RNA (gRNA) comprising a DNA-binding domain that is complementary to a target domain in a target sequence, and a CRISPR-associated endonuclease protein-binding domain. The guide RNA sequence can be a sense or anti-sense sequence. The guide RNA sequence may include a PAM. The sequence of the PAM can vary depending upon the specificity requirements of the CRISPR endonuclease used. In, e.g., the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be NGG. Other Cas endonucleases may have different PAM specificities (e.g., NNG, NNA, GAA, NGGNG, NGRRT, NGRRN, NNNNGATT, NNNNRYAC, NNAGAAW, TTTV, YG, TTTN, YTN, NGCG, NGAG, NGAN, NGNG, NG, NNGRRT, TYCV, TATV, or NAAAAC). The specific sequence of the guide RNA may vary, but, regardless of the sequence, useful guide RNA sequences will be those that minimize off-target effects while achieving high efficiency.

In some embodiments, the DNA-binding domain varies in length from about 20 to about 55 nucleotides, for example, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, or about 55 nucleotides. In some embodiments, the Cas protein-binding domain is from about 30 to about 55 nucleotides in length, for example, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, or about 55 nucleotides.

In some embodiments, the compositions comprise one or more nucleic acid (i.e. DNA) sequences encoding the guide RNA and the CRISPR endonuclease. When the compositions are administered as a nucleic acid or are contained within an expression vector, the CRISPR endonuclease can be encoded by the same nucleic acid or vector as the guide RNA sequence. In some embodiments, the CRISPR endonuclease can be encoded in a physically separate nucleic acid from the guide RNA sequence or in a separate vector. The nucleic acid sequence encoding the guide RNA may comprise a DNA binding domain, a Cas protein binding domain, and a transcription terminator domain.

The nucleic acid encoding the guide RNA and/or the CRISPR endonuclease may be an isolated nucleic acid. An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Various PCR methods are described in, for example, PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids also can be obtained by mutagenesis of, e.g., a naturally occurring portion of a Cas9-encoding DNA (in accordance with, for example, the formula above).

Target cells may be prokaryotic or eukaryotic cells. In some embodiments, cells can be fungal cells, plant cells, protist cells, or animal cells. In some embodiments, the cell is selected from the group consisting of an archaeal cell, a bacterial cell, a eukaryotic cell, a eukaryotic single-cell organism, a somatic cell, a germ cell, a stem cell, a plant cell, an algal cell, an animal cell, an invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, and a human cell.

Some embodiments are directed to a method of reducing expression or activity of a variant gene comprising at least one mutation as compared its wild-type gene, comprising introducing into a cell comprising the variant gene (a) one or more DNA sequences encoding two or more guide RNAs (gRNAs) that are complementary to two or more target sequences in the variant gene, wherein (i) at least one of the gRNAs hybridizes to a target sequence comprising a protospacer adjacent motif (PAM) site in the variant gene that (A) results from a mutation to the variant gene creating the PAM site that does not exist in the wild-type gene or (B) is operably linked to a mutated portion of the wild-type gene, (ii) at least one of the gRNAs hybridizes to a target sequence comprising a PAM site in an intron of the variant gene downstream or upstream from the PAM site of (i), and (b) a nucleic acid sequence encoding a Clustered Regularly Interspaced Short Palindromic Repeat (CRISPR)-associated endonuclease; wherein (c) a CRISPR-associated endonuclease cleaves the variant gene at the target sequences of (i) and (ii); and (d) expression or activity of the variant gene is reduced in the cell relative to a cell in which the one or more DNA sequences encoding the two or more gRNAs and the nucleic acid sequence encoding the CRISPR-associated endonuclease are not introduced. In some embodiments, the variant gene comprises 1, 2, 3, 4, 5, 6, 7, 8, 9, 10, 11, 12, 13, 14, 15, 16, 17, 18, 19, 20, or more mutations as compared to its wild-type gene. Each "mutation" can comprise one or more insertions, deletions, or substitutions. Each insertion can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, or more additional nucleotides. Each deletion can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, or more deleted nucleotides. Each substituion can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, or more substituted nucleotides.

In some embodiments, a method of reducing expression or activity of a variant gene comprises introducing into a cell comprising the variant gene one or more DNA sequences encoding two or more guide RNAs (gRNAs) that are complementary to two or more target sequences in the variant gene. In some embodiments, 1, 2, 3, 4, 5, 6, 7, 8, 9, 10, 11, 12, 13, 14, 15, 16, 17, 18, 19, 20, or more DNA sequences encoding 2, 3, 4, 5, 6, 7, 8, 9, 10, 11, 12, 13, 14, 15, 16, 17, 18, 19, 20, or more gRNAs complementary to 2, 3, 4, 5, 6, 7, 8, 9, 10, 11, 12, 13, 14, 15, 16, 17, 18, 19, 20, or more target sequences in the variant gene.

Recombinant constructs are also provided herein and can be used to transform cells in order to express the CRISPR endonuclease and/or a guide RNA complementary to a target sequence. A recombinant nucleic acid construct may comprise a nucleic acid encoding a CRISPR endonuclease and/or a guide RNA complementary to a target sequence, operably linked to a promoter suitable for expressing the CRISPR endonuclease and/or a guide RNA complementary to the target sequence in the cell. In some embodiments, the nucleic acid encoding a CRISPR endonuclease is operably linked to the same promoter as the nucleic acid encoding the guide RNA. In other embodiments, the nucleic acid encoding a CRISPR endonuclease and the nucleic acid encoding the guide RNA are operably linked to different promoters. In some embodiments, the promoter can be one or more pol III promoters, one or more pol II promoters, one or more pol I promoters, or combinations thereof. Examples of pol III promoters include, but are not limited to, U6 and H1 promoters. Examples of pol II promoters include, but are not limited to, the retroviral Rous sarcoma virus (RSV), LTR promoter (optionally with the RSV enhancer), the cytomegalovirus (CMV) promoter (optionally with the CMV enhancer; see, e.g., Boshart et al., Cell 41:521-30 (1985)), the SV40 promoter, the dihydrofolate reductase promoter, the β-actin promoter, the phosphoglycerol kinase (PGK) promoter, and the EFIa promoter. An example of a pol I promoter includes, but is not limited to, the 47S pre-rRNA promoter.

In some embodiments, one or more CRISPR endonucleases and one or more guide RNAs may be provided in combination in the form of ribonucleoprotein particles (RNPs). An RNP complex can be introduced into a subject by means of, e.g., injection, electroporation, nanoparticles (including, e.g., lipid nanoparticles), vesicles, and/or with the assistance of cell-penetrating peptides. See, e.g., Lin et al., ELife 3:e04766 (2014); Sansbury et al., CRISPR J. 2(2):121-32 (2019); US2019/0359973)

In some embodiments, one or more CRISPR endonucleases and one or more guide RNAs may be delivered by a lipid nanoparticle (LNP). An LNP refers to any particle having a diameter of less than 1000 nm, 500 nm, 250 nm, 200 nm, 150 nm, 100 nm, 75 nm, 50 nm, or 25 nm. Alternatively, a nanoparticle may range in size from 1-1000 nm, 1-500 nm, 1-250 nm, 25-200 nm, 25-100 nm, 35-75 nm, or 25-60 nm. LNPs may be made from cationic, anionic, or neutral lipids. Neutral lipids, such as the fusogenic phospholipid DOPE or the membrane component cholesterol, may be included in LNPs as "helper lipids" to enhance transfection activity and nanoparticle stability. LNPs may also be comprised of hydrophobic lipids, hydrophilic lipids, or both hydrophobic and hydrophilic lipids.

In certain embodiments, the cationic lipid N-[1-(2,3-dioleyloxy)propyl]-N,N,N-trimethylammonium chloride (DOTMA) can be used. DOTMA can be formulated alone or combined with the neutral lipid, dioleoylphosphatidyl-ethanolamine (DOPE) or other cationic or non-cationic lipids into a liposomal transfer vehicle or a lipid nanoparticle, and such liposomes can be used to enhance the delivery of nucleic acids into target cells. Other suitable cationic lipids include, but are not limited to, 5-carboxyspermylglycinedioctadecylamide, 2,3-dioleyloxy-N-[2(spermine-carboxamido)ethyl]-N,N-dimethyl-1-propanaminium, 1,2-Dioleoyl-3-Dimethylammonium-Propane, 1,2-Dioleoyl-3-Trimethylammonium-Propane. Contemplated cationic lipids also include 1,2-distearyloxy-N,N-dimethyl-3-aminopropane, 1,2-dioleyloxy-N,N-dimethyl-3-aminopropane, 1,2-dilinoleyloxy-N,N-dimethyl-3-aminopropane, 1,2-dilinolenyloxy-N,N-dimethyl-3-aminopropane, N-dioleyl-N,N-dimethylammonium chloride, N,N-distearyl-N,N-dimethylammonium bromide, N-(1,2-dimyristyloxyprop-3-yl)-N,N-dimethyl-N-hydroxyethyl ammonium bromide, 3-dimethylamino-2-(cholest-5-en-3-beta-oxybutan-4-oxy)-1-(cis,ci- s-9,12-octadecadienoxy)propane, 2-[5'-(cholest-5-en-3-beta-oxy)-3'-oxapentoxy)-3-dimethyl-1-(cis,cis-9',12'-octadecadienoxy)propane, N,N-dimethyl-3,4-dioleyloxybenzylamine, 1,2-N,N'-dioleylcarbamyl-3-dimethylaminopropane, 2,3-Dilinoleoyloxy-N,N-dimethylpropylamine, 1,2-N,N'-Dilinoleylcarbamyl-3-dimethylaminopropane, 1,2-Dilinoleoylcarbamyl-3-dimethylaminopropane, 2,2-dilinoleyl-4-dimethylaminomethyl-[1,3]-dioxolane, 2,2-dilinoleyl-4-dimethylaminoethyl-[1,3]-dioxolane, and 2-(2,2-di((9Z,12Z)-octadeca-9,12-dien-1-yl)-1,3-dioxolan-4-yl)-N,N-dimethylethanamine (DLin-KC2-DMA)), or mixtures thereof.

In some embodiments, non-cationic lipids can be used. As used herein, the phrase "non-cationic lipid" refers to any neutral, zwitterionic, or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), DOPE, palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone or can be used in combination with other excipients, for example, cationic lipids.

DNA vectors containing nucleic acids such as those described herein also are also provided. A "DNA vector" is a replicon, such as a plasmid, phage, or cosmid, into which another DNA segment may be inserted so as to bring about the replication of the inserted segment. Generally, a DNA vector is capable of replication when associated with the proper control elements. Suitable vector backbones include, for example, those routinely used in the art such as plasmids, viruses, artificial chromosomes, BACs, YACs, or PACs. The term "DNA vector" includes cloning and expression vectors, as well as viral vectors and integrating vectors. An "expression vector" is a vector that includes a regulatory region. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The DNA vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The DNA vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Direct injection of adenoviral vectors into lung tumors has been a routine procedure in clinical trials evaluating gene therapy of lung cancer. Dong et al., J. Int. Med. Res. 36:1273-87 (2008); Li et al., Cancer Gene Ther. 20:251-59 (2013); Zhou et al., Cancer Gene Ther. 23:1-6 (2016). Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al., BioTechniques 34:167-71 (2003). A large variety of such vectors are known in the art and are generally available.

Suitable nucleic acid delivery systems include recombinant viral vector, typically sequence from at least one of an adenovirus, adenovirus-associated virus (AAV), helper-dependent adenovirus, retrovirus, or hemagglutinating virus of Japan-liposome (HVJ) complex. In such cases, the viral vector comprises a strong eukaryotic promoter operably linked to the polynucleotide e.g., a cytomegalovirus (CMV) promoter. The recombinant viral vector can include one or more of the polynucleotides therein, in some embodiments about one polynucleotide. In embodiments in which the polynucleotide is to be administered with a non-viral vector, use of between from about 0.1 ng to about 4000 µg will often be useful e.g., about 0.1 ng to about 3900 µg, about 0.1 ng to about 3800 µg, about 0.1 ng to about 3700 µg, about 0.1 ng to about 3600 µg, about 0.1 ng to about 3500 µg, about 0.1 ng to about 3400 µg, about 0.1 ng to about 3300 µg, about 0.1 ng to about 3200 µg, about 0.1 ng to about 3100 µg, about 0.1 ng to about 3000 µg, about 0.1 ng to about 2900 µg, about 0.1 ng to about 2800 µg, about 0.1 ng to about 2700 µg, about 0.1 ng to about 2600 µg, about 0.1 ng to about 2500 µg, about 0.1 ng to about 2400 µg, about 0.1 ng to about 2300 µg, about 0.1 ng to about 2200 µg, about 0.1 ng to about 2100 µg, about 0.1 ng to about 2000 µg, about 0.1 ng to about 1900 µg, about 0.1 ng to about 1800 µg, about 0.1 ng to about 1700 µg, about 0.1 ng to about 1600 µg, about 0.1 ng to about 1500 µg, about 0.1 ng to about 1400 µg, about 0.1 ng to about 1300 µg, about 0.1 ng to about 1200 µg, about 0.1 ng to about 1100 µg, about 0.1 ng to about 1000 µg, about 0.1 ng to about 900 µg, about 0.1 ng to about 800 µg, about 0.1 ng to about 700 µg, about 0.1 ng to about 600 µg, about 0.1 ng to about 500 µg, about 0.1 ng to about 400 µg, about 0.1 ng to about 300 µg, about 0.1 ng to about 200 µg, about 0.1 ng to about 100 µg, about 0.1 ng to about 90 µg, about 0.1 ng to about 80 µg, about 0.1 ng to about 70 µg, about 0.1 ng to about 60 µg, about 0.1 ng to about 50 µg, about 0.1 ng to about 40 µg, about 0.1 ng to about 30 µg, about 0.1 ng to about 20 µg, about 0.1 ng to about 10 µg, about 0.1 ng to about 1 µg, about 0.1 ng to about 900 ng, about 0.1 ng to about 800 ng, about 0.1 ng to about 700 ng, about 0.1 ng to about 600 ng, about 0.1 ng to about 500 ng, about 0.1 ng to about 400 ng, about 0.1 ng to about 300 ng, about 0.1 ng to about 200 ng, about 0.1 ng to about 100 ng, about 0.1 ng to about 90 ng, about 0.1 ng to about 80 ng, about 0.1 ng to about 70 ng, about 0.1 ng to about 60 ng, about 0.1 ng to about 50 ng, about 0.1 ng to about 40 ng, about 0.1 ng to about 30 ng, about 0.1 ng to about 20 ng, about 0.1 ng to about 10 ng, about 0.1 ng to about 1 ng, about 1 ng to about 4000 µg, about 1 ng to about 3900 µg, about 1 ng to about 3800 µg, about 1 ng to about 3700 µg, about 1 ng to about 3600 µg, about 1 ng to about 3500 µg, about 1 ng to about 3400 µg, about 1 ng to about 3300 µg, about 1 ng to about 3200 µg, about 1 ng to about 3100 µg, about 1 ng to about 3000 µg, about 1 ng to about 2900 µg, about 1 ng to about 2800 µg, about 1 ng to about 2700 µg, about 1 ng to about 2600 µg, about 1 ng to about 2500 µg, about 1 ng to about 2400 µg, about 1 ng to about 2300 µg, about 1 ng to about 2200 µg, about 1 ng to about 2100 µg, about 1 ng to about 2000 µg, about 1 ng to about 1900 µg, about 1 ng to about 1800 µg, about 1 ng to about 1700 µg, about 1 ng to about 1600 µg, about 1 ng to about 1500 µg, about 1 ng to about 1400 µg, about 1 ng to about 1300 µg, about 1 ng to about 1200 µg, about 1 ng to about 1100 µg, about 1 ng to about 1000 µg, about 1 ng to about 900 µg, about 1 ng to about 800 µg, about 1 ng to about 700 µg, about 1 ng to about 600 µg, about 1 ng to about 500 µg, about 1 ng to about 400 µg, about 1 ng to about 300 µg, about 1 ng to about 200 µg, about 1 ng to about 100 µg, about 1 ng to about 90 µg, about 1 ng to about 80 µg, about 1 ng to about 70 µg, about 1 ng to about 60 µg, about 1 ng to about 50 µg, about 1 ng to about 40 µg, about 1 ng to about 30 µg, about 1 ng to about 20 µg, about 1 ng to about 10 µg, about 1 ng to about 1 µg, about 1 ng to about 900 ng, about 1 ng to about 800 ng, about 1 ng to about 700 ng, about 1 ng to about 600 ng, about 1 ng to about 500 ng, about 1 ng to about 400 ng, about 1 ng to about 300 ng, about 1 ng to about 200 ng, about 1 ng to about 100 ng, about 1 ng to about 90 ng, about 1 ng to about 80 ng, about 1 ng to about 70 ng, about 1 ng to about 60 ng, about 1 ng to about 50 ng, about 1 ng to about 40 ng, about 1 ng to about 30 ng, about 1 ng to about 20 ng, about 1 ng to about 10 ng, about 10 ng to about 4000 µg, about 20 ng to about 4000 µg, about 30 ng to about 4000 µg, about 40 ng to about 4000 µg, about 50 ng to about 4000 µg, about 60 ng to about 4000 µg, about 70 ng to about 4000 µg, about 80 ng to about 4000 µg, about 90 ng to about 4000 µg, about 100 ng to about 4000 µg, about 200 ng to about 4000 µg, about 300 ng to about 4000 µg, about 400 ng to about 4000 µg, about 500 ng to about 4000 µg, about 600 ng to about 4000 µg, about 700 ng to about 4000 µg, about 800 ng to about 4000 µg, about 900 ng to about 4000 µg, about 1 µg to about 4000 µg, 10 µg to about 4000 µg, 20 µg to about 4000 µg, 30 µg to about 4000 µg, 40 µg to about 4000 µg, 50 µg to about 4000 µg, 60 µg to about 4000 µg, 70 µg to about 4000 µg, 80 µg to about 4000 µg, 90 µg to about 4000 µg, 100 µg to about 4000 µg, 200 µg to about 4000 µg, 300 µg to about 4000 µg, 400 µg to about 4000 µg, 500 µg to about 4000 µg, 600 µg to about 4000 µg, 700 µg to about 4000 µg, 800 µg to about 4000 µg, 900 µg to about 4000 µg, 1000 µg to about 4000 µg, 1100 µg to about 4000 µg, 1200 µg to about 4000 µg, 1300 µg to about 4000 µg, 1400 µg to about 4000 µg, 1500 µg to about 4000 µg, 1600 µg to about 4000 µg, 1700 µg to about 4000 µg, 1800 µg to about 4000 µg, 1900 µg to about 4000 µg, 2000 µg to about 4000 µg, 2100 µg to about 4000 µg, 2200 µg to about 4000 µg, 2300 µg to about 4000 µg, 2400 µg to about 4000 µg, 2500 µg to about 4000 µg, 2600 µg to about 4000 µg, 2700 µg to about 4000 µg, 2800 µg to about 4000 µg, 2900 µg to about 4000 µg, 3000 µg to about 4000 µg, 3100 µg to about 4000 µg, 3200 µg to about 4000 µg, 3300 µg to about 4000 µg, 3400 µg to about 4000 µg, 3500 µg to about 4000 µg, 3600 µg to about 4000 µg, 3700 µg to about 4000 µg, 3800 µg to about 4000 µg, or 3900 µg to about 4000 µg.

Additional vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector (see, e.g., Geller et al., J. Neurochem. 64:487-96 (1995); Lim et al., in DNA Cloning: Mammalian Systems, D. Glover, Ed. (Oxford Univ. Press, Oxford England) (1995); Geller et al., Proc. Natl. Acad. Sci. USA 90:7603-07

(1993); Geller et al., Proc. Natl. Acad. Sci. USA 87:1149-53 (1990)), Adenovirus Vectors (see, e.g., Le Gal LaSalle et al., Science 259:988-90 (1993); Davidson et al., Nat. Genet. 3:219-23 (1993); Yang et al., J. Virol. 69:2004-15 (1995)), and Adeno-associated Virus Vectors (see, e.g., Kaplitt et al., Nat. Genet. 8:148-54 (1994)).

If desired, the polynucleotides described here may also be used with a microdelivery vehicle such as cationic liposomes, adenoviral vectors, and exosomes. For a review of the procedures for liposome preparation, targeting and delivery of contents, see Mannino et al., BioTechniques 6:682-90 (1988). See also Feigner et al., Bethesda Res. Lab. Focus 11(2):21 (1989) and Maurer, Bethesda Res. Lab. Focus 11(2):25 (1989). In some embodiments, exosomes may be used for delivery of a nucleic acid encoding a CRISPR endonuclease and/or guide RNA to a target cell, e.g. a cancer cell. Exosomes are nanosized vesicles secreted by a variety of cells and are comprised of cellular membranes. Exosomes can attach to target cells by a range of surface adhesion proteins and vector ligands (tetraspanins, integrins, CD11b and CD18 receptors), and deliver their payload to target cells. Several studies indicate that exosomes have a specific cell tropism, according to their characteristics and origin, which can be used to target them to disease tissues and/or organs. See Batrakova et al., J. Control. Release 219:396-405 (2015). For example, cancer-derived exosomes function as natural carriers that can efficiently deliver CRISPR/Cas9 plasmids to cancer cells. See Kim et al., J. Control. Release 266:8-16 (2017).

Replication-defective recombinant adenoviral vectors, can be produced in accordance with known techniques. See Quantin et al., Proc. Natl. Acad. Sci. USA 89:2581-84 (1992); Stratford-Perricadet et al., J. Clin. Invest. 90:626-30 (1992); Rosenfeld et al., Cell 68:143-55 (1992).

Another delivery method is to use single stranded DNA producing vectors which can produce the expressed products intracellularly. See, e.g., Chen et al., BioTechniques, 34:167-71 (2003).

In some embodiments, a nucleic acid sequence encoding a CRISPR-associated endonuclease is introduced into a cell comprising the variant gene. Introducing such nucleic acid sequences can comprise any of the aforementioned methods, and can use the same delivery method as described above for the two or more gRNAs or can use a different delivery method.

In some embodiments, the variant gene is found in a cancer cell. In some embodiments, the cancer cell is a lymphoid neoplasm diffuse large B-cell lymphoma, cholangiocarcinoma, uterine carcinosarcoma, kidney chromophobe, uveal melanoma, mesothelioma, adrenocortical carcinoma, thymoma, acute myeloid leukemia, testicular germ cell tumor, rectum adenocarcinoma, pancreatic adenocarcinoma, phenochromocytoma and paraganglioma, esophageal carcinoma, sarcoma, kidney renal papillary cell carcinoma, cervical squamous cell carcinoma and endocervical adenocarcinoma, kidney renal clear cell carcinoma, liver hepatocellular carcinoma, glioblastoma multiforme, bladder urothelial carcinoma, colon adenocarcinoma, stomach adenocarcinoma, ovarian serous cystadenocarcinoma, skin cutaneous melanoma, prostate adenocarcinoma, thyroid carcinoma, lung squamous cell carcinoma, head and neck squamous cell carcinoma, brain lower grade glioma, uterine corpus endometrial carcinoma, lung adenocarcinoma, multiple myeloma, breast invasive carcinoma, acute lymphoblastic leukemia, acute myeloid leukemia, adrenocortical carcinoma, Kaposi sarcoma, AIDS-related lymphoma, primary CNS lymphoma, anal cancer, astrocytoma, atypical teratoid/rhabdoid tumor, bile duct cancer, bladder cancer, bone cancer, brain tumor, breast cancer, bronchial tumors, carcinoid tumor, carcinoma of unknown primary, cardiac tumor, medulloblastoma, germ cell tumor, cervical cancer, chordoma, chronic lymphocytic leukemia, chronic myelogenous leukemia, chronic myeloproliferative neoplasm, colorectal cancer, craniopharyngioma, embryonal tumor, endometrial cancer, ependymoma, esophageal cancer, esthesioneuroblastoma, Ewing sarcoma, extracranial germ cell tumor, extragonadal germ cell tumor, intraocular melanoma, retinoblastoma, fallopian tube cancer, fibrous histiocytoma of bone, osteosarcoma, gallbladder cancer, gastric cancer, gastrointestinal carcinoid tumor, gastrointestinal stromal tumor, CNS germ cell tumor, ovarian germ cell tumor, testicular cancer, gestational trophoblastic disease, hairy cell leukemia, head and neck cancer, hepatocellular cancer, Langerhans cell histiocytosis, Hodgkin lymphoma, hypopharyngeal cancer, islet cell tumor, kidney cancer, laryngeal cancer, leukemia, lip and oral cavity cancer, lung cancer (non-small cell, small cell, pleuropulmonary blastoma, tracheobronchial tumor), lymphoma, male breast cancer, malignant fibrous histiocytoma of bone, melanoma, Merkel cell carcinoma, malignant mesothelioma, metastatic cancer, metastatic squamous cell neck cancer with occult primary, midline tract carcinoma, mouth cancer, multiple endocrine neoplasia, plasma cell neoplasm, mycosis fungoides, myelodysplastic syndrome, myelodysplastic neoplasm, nasal cavity and paranasal sinus cancer, nasopharyngeal cancer, neuroblastoma, non-Hodgkin lymphoma, oropharyngeal cancer, ovarian cancer, pancreatic cancer, papillomatosis, paraganglioma, parathyroid cancer, pharyngeal cancer, pheochromocytoma, pituitary tumor, pleuropulmonary blastoma, primary peritoneal cancer, prostate cancer, rectal cancer, rhabdomyosarcoma, salivary gland cancer, Sezary syndrome, skin cancer, small intestine cancer, soft tissue sarcoma, testicular cancer, thymoma, thymic carcinoma, thyroid cancer, transitional cell cancer of the renal pelvis and ureter, urethral cancer, endometrial uterine cancer, uterine sarcoma, vaginal cancer, vascular tumor, vulvar cancer, or Wilms tumor.

In some embodiments, the variant gene is NRF2, EGFR, EIF1AX, GNA11, SF3B1, BAP1, PBRM1, ATM, SETD2, KDM6A, CUL3, MET, SMARCA4, U2AF1, RBM10, STK11, NF1, NF2, IDH1, IDH2, PTPN11, MAX, TCF12, HIST1H1E, LZTR1, KIT, RAC1, ARID2, BRD4, BRD7, BARF1, NRAS, RNF43, SMAD4, ARID1A, ARID1 B, KRAS, APC, SMAD2, SMAD3, ACVR2A, GNAS, HRAS, STAG2, FGFR3, FGFR4, RHOA, CDKN1A, ERBB3, KANSL1, RB1, TP53, CDKN2A, CDKN2B, CDKN2C, KEAP1, CASP8, TGFBR2, HLA-B, MAPK1, NOTCH1, NOTCH2, NOTCH3, HLA-A, RASA1, EPHA2, EPHA3, EPHA5, EPHA7, NSD1, ZNF217, ZNF750, KLFS, EP300, FAT1, PTEN, FBXW7, PIK3CA, PIK3CB, PIK3C2B, PIK3CG, RUNX1, RUNX1T1, DNMT3A, SMC1A, ERBB2, AKT1, AKT2, AKT3, MAP3K1, FOXA1, BRCA1, BRCA2, CDH1, PIK3R1, PPP2R1A, BCOR, BCORL1, ARHGAP35, FGFR2, CHD4, CTCF, CTNNA1, CTNNB1, SPOP, TMSB4X, PIM1, CD70, CD79A, CD79B, B2M, CARD11, MYD88, BTG1, BTG2, TNFAIP3, MEN1, PRKAR1A, PDGFRA, PDGFRB, SPTA1, GABRA6, KEL, SMARCB1, ZBTB7B, BCL2, BCL2L1, BCL2L2, BCL2L11, RFC1, MAP3K4, CSDE1, EPAS1, RET, LATS2, EEF2, CYLD, HUWE1, MYH9, AJUBA, FLNA, ERBB4, CNBD1, DMD, MUC6, FAM46C, FAM46D, PLCG1, PLCG2, NIPBL, FUBP1, CIC, ZBTB2, ZBTB20, ZCCHC12, TGIF1, SOX2, SOX9, SOX10, PCBP1, ZFP36L2, TCF7L2, AMER1, KDM5A, KDM5C, MTOR, VHL, KIF1A, TCEB1, TXNIP, CUL1, TSC1, ELF3, RHOB, PSIP1, SF1, FOXQ1, GNA13, DIAPH2, ZFP36L1, ERCC2, SPTAN1, RXRA, ASXL2, CREBBP, CREB3L3, ALB, DHX9, XPO1, RPS6KA3, IL6ST, TSC2, EEF1A1, WHSC1, APOB, NUP133, AXIN1, PHF6, TET2, WT1, FLT3, FLT4, SMC3, CEBPA, RAD21, RAD50, RAD51, PTPDC1, ASXL1, EZH2, NPM1, SRSF2, GNAQ, PLCB4, CYSLTR2, CDKN1B, CBFB, NCOR1, PTPRD, TBX3, GPS2, GATA1, GATA2, GATA3, GATA4, GATA6, MAP2K4, PTCH1, PTMA, LATS1, POLRMT, CDK4, COL5A1, PPP6C, MECOM, DACH1, MAP2K1, MAP2K2, RQCD1, DDX3X, NUP93, PPM1 D, CHD2, CHD3, CCND1, CCND2, CCND3, ACVR1, KMT2A, KMT2B, KMT2C, KMT2D, SIN3A, SCAF4, DICER1, FOXA2, CTNND1, MYC, MYCL, MYCN, SOX17, ARIDSB, ATR, INPPL1, INPP4B, ATF7IP, ZMYM2, ZFHX3, PDSSB, SOS1, TAF1, PIK3R2, RPL22, RRAS2, MSH2, MSH6, CKD12, ZNF133, ZNF703, MED12, ZMYM3, GTF2I, RIT1, MGA, ABL1, BRAF, CHEK1, FANCC, JAK2, MITF, PDCD1 LG2, STAT4, ABL2, CHEK2, FANCD2, JAK3, MLH1, FANCE, JUN, MPL, RICTOR, SUFU, FANCF, GID4, KAT6A, MRE11A, PDK1, SYK, BRIP1, CRKL, FANCG, GLI1, CRLF2, FANCL, RPTOR, ALK, BTK, CSF1 R, FAS, TERC, C11orf30, KDR, MUTYH, SDHA, AR, FGF10, GPR124, SDHB, ARAF, CBL, FGF14, GRIN2A, SDHC, ARFRP1, FGF19, GRM3, KLHL6, PMS2, SDHD, TNFRSF14, DAXX, FGF23, GSK3B, POLD1, TOP1, DDR2, FGF3, H3F3A, POLE, TOP2A, CCNE1, FGF4, HGF, SLIT2, CD274, FGF6, HNF1A, NFKBIA, PRDM1, DOT1L, FGFR1, LMO1, NKX2-1, PREX2, HSD3B1, LRP1 B, TSHR, ATRX, CDC73, HSP9OAA1, PRKCI, AURKA, PRKDC, VEGFA, AURKB, CDK12, FH, MAGI2, PRSS8, SMO, FLCN, IGF1 R, SNCAIP, WISP3, AXL, CDK6, EPHB1, FLT1, IGF2, SOCS1, CDK8, IKBKE, NTRK1, BARD1, IKZF1, NTRK2, QKI, FOXL2, IL7R, MCL1, NTRK3, ERG, FOXP1, INHBA, MDM2, SPEN, ERRFI1, FRS2, MDM4, PAK3, BCL6, ESR1, IRF2, PALB2, RAF1, IRF4, MEF2B, PARK2, RANBP2, SRC, IRS2, PAX5, RARA, BLM, FANCA, JAK1, FCRL4, LIG4, MAR, PWWP3A, MUC16, MUC17, FCGBP, FAT17, MMSET, IRTA2, TTN, DST, or STAT3.

In some embodiments, a nucleic acid sequence encoding a CRISPR-associated endonuclease is introduced into a cell comprising a wild-type gene, which comprises the target exon(s) and intron(s). Introducing such nucleic acid sequences can comprise any of the aforementioned methods, and can use the same delivery method as described above for the two or more gRNAs or can use a different delivery method.

In some embodiments, at least one of the gRNAs hybridizes to a target sequence comprising a PAM site in the variant gene that results from a mutation to the variant gene creating the PAM site that does not exist in the wild-type gene. In some embodiments, at least one of the gRNAs hybridizes to a target sequence comprising a PAM site in the variant gene that is operably linked to a mutated portion of the wild-type gene. The term "mutation" means a variation from a known reference sequence and includes mutations such as, for example, single nucleotide variants (SNVs), copy number variants or variations (CNVs)/aberrations, insertions or deletions (indels), gene fusions, transversions, translocations, frame shifts, duplications, repeat expansions, and epigenetic variants. A mutation can be a germline or somatic mutation. Mutations can be caused by, e.g., one or more nucleotide additions, substitutions, or deletions. In some embodiments, one or more mutations in a nucleotide sequence produce a new PAM site as compared to a wild-type nucleotide sequence that does not contain such PAM site. In some embodiments, one or more mutations in a nucleotide sequence shift a PAM site to a different location in the nucleotide sequence (e.g., from an intron to an exon, from an exon to an intron, from a position upstream in a gene to a position downstream, or from a position downstream in a gene to a position upstream) as compared to the PAM site's location in a wild-type nucleotide sequence.

In some embodiments, the mutation is a fusion between two genes where the resulting fusion creates a new PAM site. In some embodiments, the PAM site is newly created as between one of the two genes that forms the fusion gene (i.e., the new fusion gene contains a PAM site that already existed in one of the two contributors to the fusion gene), and in some embodiments, the PAM site is new created as between both genes that form the fusion gene (i.e., the new fusion gene contains a new PAM site that does not exist in either contributor to the fusion gene).

In some embodiments, at least one of the gRNAs hybridizes to a target sequence comprising a PAM site in an intron of the variant gene downstream or upstream from the PAM site discussed above. In some embodiments, the PAM site in an intron of the variant gene can be present in the same location in the wild-type gene. In some embodiments, the PAM site in an intron of the variant gene is not present in the related wild-type gene.

In some embodiments, one gRNA can be a gRNA hybridizes to a target sequence in a variant NRF2, e.g., a gRNA that targets an R34G NRF2 variant, e.g., SEQ ID NO:1. In some embodiments, e.g. in embodiments in combination with the gRNA of SEQ ID NO:1, the intron gRNA can be one or more of SEQ ID NOs: 2-7 and/or 15-34.

In some embodiments, one gRNA can be a gRNA hybridizes to a target sequence in a variant EGFR, e.g., a gRNA that targets an L858R EGFR variant, e.g., SEQ ID NO:8. In some embodiments, e.g. in embodiments in combination with the gRNA of SEQ ID NO:1, the intron gRNA can be one or more of SEQ ID NOs: 9-14 and/or 35-53.

In some embodiments, expression or activity of the variant gene is reduced in the cell relative to a cell in which the one or more DNA sequences encoding the two or more gRNAs and the nucleic acid sequence encoding the CRISPR-associated endonuclease are not introduced. In some embodiments, the expression or activity of the variant gene is reduced at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% as compared to the expression or activity of the variant gene in a cell in which the one or more DNA sequences encoding the two or more gRNAs and the nucleic acid sequence encoding the CRISPR-associated endonuclease are not introduced. In some embodiment, the expression and/or activity of the related wild-type gene is unaffected. In some embodiments, the expression and/or activity of the related wild-type gene is reduced only about %, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%.

In some embodiments, introduction of the one or more DNA sequences encoding the two or more gRNAs and the nucleic acid sequence encoding the CRISPR-associated endonuclease results in no off-site mutagenesis. In some embodiments, introduction of the one or more DNA sequences encoding the two or more gRNAs and the nucleic acid sequence encoding the CRISPR-associated endonuclease results in off-site mutagenesis at a frequency of only about 0.01%, 0.02%, 0.03%, 0.04%, 0.05%, 0.06%, 0.07%, 0.08%, 0.09%, or 0.1%.

Pharmaceutical Compositions

Any of the pharmaceutical compositions disclosed herein can be formulated for use in the preparation of a medicament, and particular uses are indicated below in the context of treatment, e.g., the treatment of a subject having cancer. When employed as pharmaceuticals, any of the nucleic acids and vectors can be administered in the form of pharmaceutical compositions. Administration may be pulmonary (e.g., by inhalation or insufflation of powders or aerosols, including by nebulizer; intratracheal, intranasal, epidermal and transdermal), topical (including ophthalmic and to mucous membranes including intranasal, vaginal and rectal delivery), ocular, oral or parenteral. Parenteral administration includes intravenous, intra-arterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

In some embodiments, pharmaceutical compositions can contain, as the active ingredient, nucleic acids and vectors described herein in combination with one or more pharmaceutically acceptable carriers. The term "pharmaceutically acceptable" refers to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the pharmaceutical compositions disclosed herein, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid.

EXAMPLES

The present disclosure is further defined in the following Examples. It should be understood that these Examples, while indicating exemplary embodiments of the present disclosure, are given by way of illustration only.

Cell Lines and Culture conditions

Human lung squamous cell carcinoma NCI-H1703 clone 44-25 cells were derived from NCI-H1703 cells (#CRL-5889) which were purchased from ATCC (Manassas, VA, USA). NCI-H1703 clone 44-25 cells contains R34G mutation (C 4 G) in NFE2L2 gene. H1703 clone 44-25 cells were cultured in ATCC formulation RPMI-1640 with 10% FBS. T75 flasks were used and cells were split 1:5 upon reaching 90% confluency. Human lung adenocarcinoma cells (Dist. Lot. No. LG0703-F948-PDC) were acquired from the National Institute of Health's National Cancer Institute's Patient-Derived Models Repository (PDMR). This PDMR cell line contains the L858R mutation (T 4 G) in the EGFR gene. The PDMR cells were maintained in Advanced DMEM/F12 media containing 10% FBS, 0.4 µg/mL hydrocortisone, 0.01 µg/mL EGF Recombinant Human Protein, 24 µg/mL adenine, and 2 mM L-Glutamine. T75s were used and cells were split 1:3 upon reaching 90% confluency. All cultures were maintained in cell culture incubators at 37° C. and 5% $CO_2$.

PCR

Genomic DNA was isolated from samples using the Qiagen DNeasy Blood and Tissue Kit. All PCRs were conducted with Q5 High-Fidelity DNA Polymerase. 40 ng total of DNA was used in all genomic DNA PCR reactions. RNA was isolated using Invitrogen PureLink Mini Kit and converted to cDNA with Applied Biosystems High-Capacity RNA-to-cDNA Kit. 0.5 µL of cDNA sample were used in all cDNA PCR reactions. All PCR reactions were run for 35 cycles.

Agarose Gel Electrophoresis

Gels were cast with 100 g of agarose, 100 mL of TBE buffer, and 10 µL SYBR Safe DNA Gel Stain. Samples were loaded with 5 µL of PCR product and 1 µL of Thermo Scientific 6× DNA Loading Dye. Electrophoresis was conducted at 80 volts for 75 minutes in TBE buffer. Gels were imaged with the Azure Biosystems Azure 300 Gel Imager.

RNP Assembly

Ribonucleoproteins (RNP) are complexed by incubating 250 pmol of purified synthetic gRNA (Synthego Corporation, Redwood City, CA) with 50 pmol of purified spCas9 (Synthego Corporation, Redwood City, CA) at room temperature in nuclease-free 1× TE buffer for 15 minutes.

Nucleofection

Transfections were carried out using the Lonza Nuclefector 4d. Cultures in t75s at 90% confluence were split 1:2 24 hours prior to transfection. RNPs were complexed at 250:50 pmol for 30 minutes prior to transfection, during which time cells were harvested and counted. All reactions were 100 µL and contained 1 e6 cells. Lonza SF solution and Nucleofector program CM-130 were used in all transfections of the H1703 cell line. Lonza SE solution and Nucleofector program CA-137 were used in all transfections of the PDMR. After transfection, 500 µL of media that had been equilibrated to cell culture $CO_2$ and temperature conditions was added to each 100 µL cuvettes. Cuvettes were then placed in the incubator. After 20 minutes, the entire content of each cuvette was seeded into 3 mL of media in a 6 well plate. After 72 hours, samples were dissociated using 200 µL Trypsin 0.25% for 5 minutes. 800 µL culture media was used to quench and split into 1.5 mL tubes each containing 500 µL of the sample. Tubes were spun at 300×g for 5 minutes. One of the tubes was placed in the −20° C. freezer and the other was resuspended in 500 µL of Trizol for RNA extraction and cDNA synthesis.

Sequencing and Analysis of Indel Efficiency

All sequencing was performed on the Applied Biosystems SeqStudio. The BigDye Terminator v3.1 Cycle Sequencing Kit was used to prepare samples for sequencing. Resulting sequences were analyzed with DECODR to determine indel rates (Bloh et al., CRISPR J. 4:120-31 (2021)).

TABLE 1 gRNAs

| Target Gene | gRNA ID | Sequence | PAM | SEQ ID NO |
|---|---|---|---|---|
| NRF2 | R34G | GATATAGATCTTGGAGTAAG | TGG | 1 |
| NRF2 | 3-4_SKgRNA1 | TTAAATGGAGATTCATTGAC | GGG | 2 |
| NRF2 | 3-4_SKgRNA2 | CCTTGACAAGAGTATTTCCT | TGG | 3 |
| NRF2 | 3-4_SKgRNA3 | TCTGGCTATGCAATAGTCAA | TGG | 4 |
| NRF2 | 4-5_SKgRNA1 | TAAATAATCAGAATGACTAA | AGG | 5 |
| NRF2 | 4-5_SKgRNA2 | CCCATGCTAGTTAAATTGGT | TGG | 6 |
| NRF2 | 4-5_SKgRNA3 | GAGTTCCCAGATCAGACGTC | AGG | 7 |
| EGFR | L858R | TCAAGATCACAGATTTTGGG | CGG | 8 |
| EGFR | 21-22_SKgRNA1 | AGTGTGAGCCAGAGCTGCTT | TGG | 9 |
| EGFR | 21-22_SKgRNA2 | GTATTGTTTAACACATGCAG | GGG | 10 |
| EGFR | 21-22_SKgRNA3 | GCCAGCATTTTCCTGACACC | AGG | 11 |
| EGFR | 22-23_SKgRNA1 | AATCTCCAGTGACTTTTGGA | CGG | 12 |
| EGFR | 22-23_SKgRNA2 | GAGATTGCAATGAGCTCGTC | TGG | 13 |
| EGFR | 22-23_SKgRNA3 | ATTTGAAGTGAACCAGAGGG | AGG | 14 |

Example 1

Screening of SureKill Guide RNAs in the NFE2L2 Gene

In some cancers, human NRF2 contains a mutation, R34G, that creates a novel PAM site making it a targetable sequence by CRISPR. By combining the R34G-targeting CRISPR with another CRISPR of high efficiency in a downstream intronic region, exon skipping can be induced, resulting in a higher efficiency of functional knockout than the R34G targeting CRISPR alone. To find a suitable SureKill guide RNA (gRNA) to pair with the R34G targeting CRISPR, we selected the intron between exons 3 and 4 (FIG. 2). A series of gRNAs were created in this region and screened for their ability to induce indels, a measure of their activity (Table 2).

TABLE 2

| gRNA | Sequence | indel % | SEQ ID NO |
|---|---|---|---|
| R34G | GATATAGATCTTGGAGTAAG | 83 | 1 |
| 1 | TTAAATGGAGATTCATTGAC | 16 | 2 |
| 3 | TCTGGCTATGCAATAGTCAA | 83.6 | 4 |
| 10 | GGTTTTGTATTGTGTGAA | 32.2 | 15 |
| 11 | GCTATGCAATAGTCAATGGTTT | 32.95 | 16 |
| 12 | GACTATTGCATAGCCAGAAACA | 95.3 | 17 |
| 13 | GCAAATGGGTTATTTGTTTCCA | 32.35 | 18 |
| 14 | GGTGAGTAAAGAGCCAGCT | 57.55 | 19 |
| 15 | GTTTATATAATATCTAGCACAG | 71.3 | 20 |
| 16 | GACTCAAATTTATAATTTGC | 3.8 | 21 |
| 17 | GCAAATTATAAATTTGAGTCAG | 15.05 | 22 |
| 19 | GCGTAAGTACAATCTTT | 74 | 23 |
| 21 | GAAACATGGACAGCATAACCA | 87.15 | 24 |
| 22 | GTTTCTGGCTATGCAATAGTCAA | 30.15 | 25 |
| 24 | GGCACCACTACAAAACAAAA | 39.4 | 26 |
| 25 | GGGGATGAGTAAGCTCTA | 95.35 | 27 |
| 26 | GCTTACTCATCCCCTGTTGG | 89.65 | 28 |
| 27 | GAGCTTACTCATCCCCTGT | 28.95 | 29 |
| 29a | GATTCCATTTTGTTTTGTAG | 11.85 | 30 |
| 29b | GATTTATGAGTCTTCCACCAAC | 11.8 | 31 |
| 30 | GATTTGTTATTTACAAACG | 28.55 | 32 |
| 31 | GTTTGGTGAGTAAAGAGCCAGC | 14.55 | 33 |
| 32 | GGTTATGCTGTCCATGTTTC | 47.8 | 34 |

In Table 2, all sequences are listed from 5' to 3'. Indel %, a measure of CRISPR activity, is based on transfections of individual guide RNAs. All guide RNAs, with the exception of R34G, were designed in the intron between exons 3 and 4.

Example 2

Assessment of SureKill Guide RNA-Induced Exon Skipping in NFE2L2

To ensure that targeting the intron with CRISPR on its own does not induce exon skipping, the high-activity gRNAs from the screening process were introduced into the cells. The cells were then used for cDNA analysis to assess whether exon skipping was occurring (FIG. 3).

While some of the intron-targeting gRNAs did result in some level of exon skipping (gRNAs 21, 25, and 26), gRNAs 3, 12, 14, and 15 did not show any exon skipping when they were individually applied in the CRISPR reactions (FIG. 3). These gRNAs are candidates for SureKill approach.

Example 3

Assessment of Genomic DNA After Treatment with the R34G Guide RNA, SureKill Guide RNAs, and a Combination of Both When combined with the R34G targeting CRISPR, the intron-targeting gRNAs efficiently induce large deletions between the two CRISPRs as shown in lanes 8-11 (FIG. 4). The same intron-targeting gRNAs do not induce the same deletions when not paired with the R34G targeting CRISPR (lanes 4-7). Likewise, the R34G targeting CRISPR alone does not induce a large deletion as it does when paired with an intron-targeting CRISPR.

Example 4

Assessment of cDNA After Treatment with the R34G Guide RNA, SureKill Guide RNAs, and a Combination of Both The R34G targeting CRISPR was paired with the intron targeting CRISPRs and assessed for exon skipping by examining the cDNA from cells exposed to the CRISPR pairs (FIG. 5). While the R34G targeting CRISPR induced some level of exon skipping (lane 3) (see, e.g., Banas et al., Exon skipping induced by CRISPR-directed gene editing regulates the response to chemotherapy in non-small cell lung carcinoma cells, Gene Ther. (2022)), there is a clear enhanced reduction in the full-size transcript from the samples that were exposed to the pairs (lanes 4-6) compared to the R34G targeting CRISPR alone.

Example 5

Screening of SureKill Guide RNAs in the EGFR Gene

Human EGFR is a frequently mutated gene that is associated with cancers. One of the most common mutations is L858R which results in the creation of a novel PAM site, making it a targetable sequence by CRISPR. Like the R34G mutation, the CRISPR designed to target the L858R mutation is not highly efficient on its own. By combining the L858R-targeting CRISPR with another CRISPR of high efficiency in a downstream intronic region, exon skipping can be induced, resulting in a higher efficiency of functional knockout than the L858R targeting CRISPR alone. To find a suitable gRNA to pair with the L858R targeting CRISPR, we selected the intron between exons 21 and 22 (FIG. 6). A series of gRNAs were created in this region and screened for their ability to induce indels, a measure of their activity using DECODR (Bloh et al., CRISPR J. 4:120-31 (2021)) (Table 3).

TABLE 3

| gRNA | Sequence | indel % | SEQ ID NO |
|---|---|---|---|
| L858R | TCAAGATCACAGATTTTGGG | 73.2 | 8 |
| 1 | AGTGTGAGCCAGAGCTGCTT | 14.2 | 9 |
| 2 | GTATTGTTTAACACATGCAG | 2 | 10 |
| 3 | GCCAGCATTTTCCTGACACC | 19.2 | 11 |
| 10A | GTTTAACACATGCAGGGG | 0 | 35 |
| 10B | GTATTGTTTAACACATGCAGGGG | 0 | 36 |
| 11 | GGATGCTCTCCAGACATTCT | 92.4 | 37 |
| 12 | GAGGATGCTCTCCAGACATTC | 42.3 | 38 |
| 13 | GAGCTCGCAGCAGCTGCTGC | 57.3 | 39 |
| 14 | GCTGGCAGCTGGGTCCAGCC | 0 | 40 |

TABLE 3-continued

| gRNA | Sequence | indel % | SEQ ID NO |
|---|---|---|---|
| 15 | GCAGCTCTGGCTCACACTACC | 23.4 | 41 |
| 16 | GGGTCCAGCCAGGGTCTCC | 77.4 | 42 |
| 17 | GCTCACACTACCAGGAGACCC | 100 | 43 |
| 19 | GTGTGAGCCAGAGCTGCTTT | 78.85 | 44 |
| 21 | GTACTTGCTGGGACAGTGAATG | 18.35 | 45 |
| 22 | GTCCCTGGTGTCAGGAAAATGC | 100 | 46 |
| 23 | GCATTTTCCTGACACCAGGGACC | 96.15 | 47 |
| 24 | GTGTTAAACAATACAGCTAG | 17.35 | 48 |
| 25 | GCTGTATTGTTTAACACATGC | 25.6 | 49 |
| 27 | GTATTGTTTAACACATGCA | 95 | 50 |
| 28 | GCAGCCTGGTCCCTGGTGTC | 97.6 | 51 |
| 29 | GTTAAACAATACAGCTAGT | 100 | 52 |
| 30 | GTTAAACAATACAGCTAGTGGGA | 11.7 | 53 |

In Table 3, all sequences are listed from 5' to 3'. Indel percent, a measure of CRISPR activity, is based on transfections of individual guide RNAs. All guide RNAs, with the exception of L858R, were designed in the intron between exons 21 and 22.

Example 6

Assessment of SureKill Guide RNA-Induced Exon Skipping in EGFR

To ensure that targeting the intron with CRISPR on its own does not induce exon skipping, the high-activity gRNAs from the screening process were introduced into cells. The cells were then used for cDNA analysis to assess whether exon skipping was occurring (FIG. 7). While some of the intron-targeting gRNAs did result in low levels of exon skipping on their own, most did not. A select few (gRNAs 19, 27 and 28) were then combined with the L858R targeting CRISPR.

Example 7

Assessment of Genomic DNA After Treatment with the L858R Guide RNA, SureKill Guide RNAs, and a Combination of Both When combined with the L858R targeting CRISPR, the intron-targeting gRNAs efficiently induce large deletions between the two CRISPRs as shown in lanes 6-8 (FIG. 8). When not paired with the L858R CRISPR, the same intron-targeting gRNAs do not induce large deletions (lanes 4-5, and 9). Likewise, as shown in lane 3, the L858R targeting CRISPR does not induce a large deletion as it does when paired with an intron-targeting CRISPR.

Example 8

Impact on Expression Level as a Result of L858R Guide RNA Targeting and L858R Guide RNA in Combination with SureKill Guide RNAs The L858R targeting CRISPR was paired with the intron targeting CRISPRs (gRNAs 19, 27, and 28) and assessed for exon skipping by examining the cDNA from cells exposed to the CRISPR pairs (FIG. 9). While the L858R targeting CRISPR induced some level of exon skipping on its own, there is an enhanced reduction in the full-size transcript from the samples that were exposed to the pairs (lanes 7-9) compared to the L858R targeting CRISPR alone (lane 3).

What is claimed is:

1. A method of reducing expression or activity of a variant gene comprising at least one mutation as compared to its wild-type gene, comprising introducing into a cell comprising the variant gene
 (a) one or more nucleic acid sequences encoding two or more guide RNAs (gRNAs) that are complementary to two or more target sequences in the variant gene, wherein
  (i) one or more of the gRNAs hybridizes to a target sequence comprising a protospacer adjacent motif (PAM) site in an exon of the variant gene that results from a mutation to the variant gene creating the PAM site that does not exist in the wild-type gene, and
  (ii) one or more of the gRNAs hybridizes to a target sequence comprising a PAM site in an intron of the variant gene downstream or upstream from the PAM site of (i), and
 (b) one or more nucleic acid sequences encoding one or more Clustered Regularly Interspaced Short Palindromic Repeat (CRISPR)-associated endonucleases;
wherein
 (c) the one or more CRISPR-associated endonucleases cleave the variant gene at the target sequences of (i) and (ii) thereby inducing exon skipping in the variant gene; and
 (d) expression or activity of the variant gene is reduced in the cell relative to a cell in which the one or more nucleic acid sequences encoding the two or more gRNAs or the one or more nucleic acid sequences encoding one or more CRISPR-associated endonucleases are not introduced.

2. The method of claim 1, wherein the two or more gRNAs comprise a trans-activated small RNA (tracrRNA) and a CRISPR RNA (crRNA).

3. The method of claim 1, wherein the two or more gRNAs are each one or more single guide RNAs.

4. The method of claim 1, wherein at least one of the one or more CRISPR-associated endonucleases is a class 2 CRISPR-associated endonuclease.

5. The method of claim 4, wherein the class 2 CRISPR-associated endonuclease is Cas9 or Cas12a.

6. The method of claim 1, wherein the expression or activity of the variant gene is reduced in the cell relative to a cell in which the one or more nucleic acid sequences encoding the two or more gRNAs and the one or more nucleic acid sequences encoding one or more CRISPR-associated endonucleases are not introduced.

7. A method of reducing expression or activity of a variant gene comprising at least one mutation as compared to its wild-type gene comprising introducing into a cancer cell
 (a) two or more guide RNAs (gRNAs) that are complementary to two or more target sequences in the variant gene, wherein
  (i) at least one of the gRNAs hybridizes to a target sequence comprising a protospacer adjacent motif (PAM) site in an exon of the variant gene that results from a mutation to the variant gene creating the PAM site that does not exist in the wild-type gene, and
  (ii) at least one of the gRNAs hybridizes to a target sequence comprising a PAM site in an intron of the variant gene downstream or upstream from the PAM site of (i), and
 (b) one or more CRISPR-associated endonucleases;
 whereby one or more CRISPR-associated endonucleases cleave the variant gene at the target sequence of (i) and the target sequence of (ii) thereby inducing exon skipping in the variant gene; and
 wherein expression or activity of the variant gene is reduced in the cell relative to a cell in which the two or more gRNAs or the one or more CRISPR-associated endonucleases are not introduced.

8. The method of claim 7, wherein the two or more gRNAs comprise a tracrRNA and a crRNA.

9. The method of claim 7, wherein the two or more gRNAs are each one or more single guide RNAs.

10. The method of claim 7, wherein at least one of the one or more CRISPR-associated endonucleases is a class 2 CRISPR-associated endonuclease.

11. The method of claim 10, wherein the class 2 CRISPR-associated endonuclease is Cas9 or Cas12a.

12. The method of claim 7, wherein the expression or activity of the variant gene is reduced in the cell relative to a cell in which the two or more gRNAs and the one or more CRISPR-associated endonucleases are not introduced.

13. A method of treating cancer in a subject comprising administering to the subject a therapeutically effective amount of a pharmaceutical composition comprising two or more gRNAs, each gRNA comprising a DNA-binding domain and a CRISPR-associated endonuclease protein-binding domain, wherein
 (a) the DNA-binding domain of at least one of the gRNAs is complementary to a target sequence comprising a protospacer adjacent motif (PAM) site in an exon of a variant gene of a wild-type gene that results from a mutation to the variant gene creating the PAM site that does not exist in the wild-type gene; and
 (b) at least one of the gRNAs is complementary to a target sequence comprising a PAM site in an intron of the variant gene downstream or upstream from the PAM site of (a);
 wherein cleavage of the variant gene by one or more CRISPR-associated endonucleases at the target sequences of (a) and (b) induces exon skipping in the variant gene.

14. The method of claim 13, further comprising administering one or more chemotherapeutic agents to the subject.

15. The method of claim 14, wherein the one or more chemotherapeutic agents are selected from the group consisting of cisplatin, vinorelbine, carboplatin, paclitaxel, and a combination thereof.

16. The method of claim 13, wherein the cancer is a lymphoid neoplasm diffuse large B-cell lymphoma, cholangiocarcinoma, uterine carcinosarcoma, kidney chromophobe, uveal melanoma, mesothelioma, adrenocortical carcinoma, thymoma, acute myeloid leukemia, testicular germ cell tumor, rectum adenocarcinoma, pancreatic adenocarcinoma, phenochromocytoma and paraganglioma, esophageal carcinoma, sarcoma, kidney renal papillary cell carcinoma, cervical squamous cell carcinoma and endocervical adenocarcinoma, kidney renal clear cell carcinoma, liver hepatocellular carcinoma, glioblastoma multiforme, bladder urothelial carcinoma, colon adenocarcinoma, stomach adenocarcinoma, ovarian serous cystadenocarcinoma, skin cutaneous melanoma, prostate adenocarcinoma, thyroid carcinoma, lung squamous cell carcinoma, head and neck squamous cell carcinoma, brain lower grade glioma, uterine corpus endometrial carcinoma, lung adenocarcinoma, multiple myeloma, breast invasive carcinoma, acute lymphoblastic leukemia, acute myeloid leukemia, adrenocortical carcinoma, Kaposi sarcoma, AIDS-related lymphoma, primary CNS lymphoma, anal cancer, astrocytoma, atypical teratoid/rhabdoid tumor, bile duct cancer, bladder cancer, bone cancer, brain tumor, breast cancer, bronchial tumors, carcinoid tumor, carcinoma of unknown primary, cardiac tumor, medulloblastoma, germ cell tumor, cervical cancer, chordoma, chronic lymphocytic leukemia, chronic myelogenous leukemia, chronic myeloproliferative neoplasm, colorectal cancer, craniopharyngioma, embryonal tumor, endometrial cancer, ependymoma, esophageal cancer, esthesioneuroblastoma, Ewing sarcoma, extracranial germ cell tumor, extragonadal germ cell tumor, intraocular melanoma, retinoblastoma, fallopian tube cancer, fibrous histiocytoma of bone, osteosarcoma, gallbladder cancer, gastric cancer, gastrointestinal carcinoid tumor, gastrointestinal stromal tumor, CNS germ cell tumor, ovarian germ cell tumor, testicular cancer, gestational trophoblastic disease, hairy cell leukemia, head and neck cancer, hepatocellular cancer, Langerhans cell histiocytosis, Hodgkin lymphoma, hypopharyngeal cancer, islet cell tumor, kidney cancer, laryngeal cancer, leukemia, lip and oral cavity cancer, lung cancer, lymphoma, male breast cancer, malignant fibrous histiocytoma of bone, melanoma, Merkel cell carcinoma, malignant mesothelioma, metastatic cancer, metastatic squamous cell neck cancer with occult primary, midline tract carcinoma, mouth cancer, multiple endocrine neoplasia, plasma cell neoplasm, mycosis fungoides, myelodysplastic syndrome, myelodysplastic neoplasm, nasal cavity and paranasal sinus cancer, nasopharyngeal cancer, neuroblastoma, non-Hodgkin lymphoma, oropharyngeal cancer, ovarian cancer, pancreatic cancer, papillomatosis, paraganglioma, parathyroid cancer, pharyngeal cancer, pheochromocytoma, pituitary tumor, pleuropulmonary blastoma, primary peritoneal cancer, prostate cancer, rectal cancer, rhabdomyosarcoma, salivary gland cancer, Sezary syndrome, skin cancer, small intestine cancer, soft tissue sarcoma, testicular cancer, thymoma, thymic carcinoma, thyroid cancer, transitional cell cancer of the renal pelvis and ureter, urethral cancer, endometrial uterine cancer, uterine sarcoma, vaginal cancer, vascular tumor, vulvar cancer, or Wilms tumor.

17. The method of claim 16, wherein the lung cancer is a non-small cell lung cancer, small cell lung cancer, pleuropulmonary blastoma, or tracheobronchial tumor.

18. A method of treating cancer in a subject comprising administering to the subject a therapeutically effective amount of a pharmaceutical composition comprising an RNP complex comprising
(a) two or more gRNAs, each gRNA comprising a DNA-binding domain and a CRISPR-associated endonuclease protein-binding domain, wherein
(i) the DNA-binding domain of at least one of the gRNAs is complementary to a target sequence comprising a protospacer adjacent motif (PAM) site in an exon of a variant gene of a wild-type gene that results from a mutation to the variant gene creating the PAM site that does not exist in the wild-type gene; and
(ii) at least one of the gRNAs is complementary to a target sequence comprising a PAM site in an intron of the variant gene downstream or upstream from the PAM site of (i); and
(b) one or more CRISPR-associated endonucleases;
wherein the one or more CRISPR-associated endonucleases cleave the variant gene at the target sequences of (i) and (ii) thereby inducing exon skipping in the variant gene.

* * * * *

```
                        SEQUENCE LISTING

<160> NUMBER OF SEQ ID NOS: 53

<210> SEQ ID NO 1
<211> LENGTH: 20
<212> TYPE: DNA
<213> ORGANISM: Artificial Sequence
<220> FEATURE:
<223> OTHER INFORMATION: gRNA

<400> SEQUENCE: 1
gatatagatc ttggagtaag                                                    20

<210> SEQ ID NO 2
<211> LENGTH: 20
<212> TYPE: DNA
<213> ORGANISM: Artificial Sequence
<220> FEATURE:
<223> OTHER INFORMATION: gRNA

<400> SEQUENCE: 2
ttaaatggag attcattgac                                                    20

<210> SEQ ID NO 3
<211> LENGTH: 20
<212> TYPE: DNA
<213> ORGANISM: Artificial Sequence
<220> FEATURE:
<223> OTHER INFORMATION: gRNA

<400> SEQUENCE: 3
ccttgacaag agtatttcct                                                    20

<210> SEQ ID NO 4
<211> LENGTH: 20
<212> TYPE: DNA
<213> ORGANISM: Artificial Sequence
<220> FEATURE:
<223> OTHER INFORMATION: gRNA

<400> SEQUENCE: 4
tctggctatg caatagtcaa                                                    20

<210> SEQ ID NO 5
<211> LENGTH: 20
<212> TYPE: DNA
<213> ORGANISM: Artificial Sequence
<220> FEATURE:
<223> OTHER INFORMATION: gRNA

<400> SEQUENCE: 5
taaataatca gaatgactaa                                                    20

<210> SEQ ID NO 6
<211> LENGTH: 20
<212> TYPE: DNA
<213> ORGANISM: Artificial Sequence
<220> FEATURE:
<223> OTHER INFORMATION: gRNA

<400> SEQUENCE: 6
cccatgctag ttaaattggt                                                    20
```

<210> SEQ ID NO 7
<211> LENGTH: 20
<212> TYPE: DNA
<213> ORGANISM: Artificial Sequence
<220> FEATURE:
<223> OTHER INFORMATION: gRNA

<400> SEQUENCE: 7
gagttcccag atcagacgtc                                              20

<210> SEQ ID NO 8
<211> LENGTH: 20
<212> TYPE: DNA
<213> ORGANISM: Artificial Sequence
<220> FEATURE:
<223> OTHER INFORMATION: gRNA

<400> SEQUENCE: 8
tcaagatcac agattttggg                                              20

<210> SEQ ID NO 9
<211> LENGTH: 20
<212> TYPE: DNA
<213> ORGANISM: Artificial Sequence
<220> FEATURE:
<223> OTHER INFORMATION: gRNA

<400> SEQUENCE: 9
agtgtgagcc agagctgctt                                              20

<210> SEQ ID NO 10
<211> LENGTH: 20
<212> TYPE: DNA
<213> ORGANISM: Artificial Sequence
<220> FEATURE:
<223> OTHER INFORMATION: gRNA

<400> SEQUENCE: 10
gtattgttta acacatgcag                                              20

<210> SEQ ID NO 11
<211> LENGTH: 20
<212> TYPE: DNA
<213> ORGANISM: Artificial Sequence
<220> FEATURE:
<223> OTHER INFORMATION: gRNA

<400> SEQUENCE: 11
gccagcattt tcctgacacc                                              20

<210> SEQ ID NO 12
<211> LENGTH: 20
<212> TYPE: DNA
<213> ORGANISM: Artificial Sequence
<220> FEATURE:
<223> OTHER INFORMATION: gRNA

<400> SEQUENCE: 12
aatctccagt gacttttgga                                              20

<210> SEQ ID NO 13
<211> LENGTH: 20
<212> TYPE: DNA
<213> ORGANISM: Artificial Sequence
<220> FEATURE:
<223> OTHER INFORMATION: gRNA

```
<400> SEQUENCE: 13
gagattgcaa tgagctcgtc                                              20

<210> SEQ ID NO 14
<211> LENGTH: 20
<212> TYPE: DNA
<213> ORGANISM: Artificial Sequence
<220> FEATURE:
<223> OTHER INFORMATION: gRNA

<400> SEQUENCE: 14
atttgaagtg aaccagaggg                                              20

<210> SEQ ID NO 15
<211> LENGTH: 18
<212> TYPE: DNA
<213> ORGANISM: Artificial Sequence
<220> FEATURE:
<223> OTHER INFORMATION: gRNA

<400> SEQUENCE: 15
ggttttgtat tgtgtgaa                                                18

<210> SEQ ID NO 16
<211> LENGTH: 22
<212> TYPE: DNA
<213> ORGANISM: Artificial Sequence
<220> FEATURE:
<223> OTHER INFORMATION: gRNA

<400> SEQUENCE: 16
gctatgcaat agtcaatggt tt                                           22

<210> SEQ ID NO 17
<211> LENGTH: 22
<212> TYPE: DNA
<213> ORGANISM: Artificial Sequence
<220> FEATURE:
<223> OTHER INFORMATION: gRNA

<400> SEQUENCE: 17
gactattgca tagccagaaa ca                                           22

<210> SEQ ID NO 18
<211> LENGTH: 22
<212> TYPE: DNA
<213> ORGANISM: Artificial Sequence
<220> FEATURE:
<223> OTHER INFORMATION: gRNA

<400> SEQUENCE: 18
gcaaatgggt tatttgtttc ca                                           22

<210> SEQ ID NO 19
<211> LENGTH: 19
<212> TYPE: DNA
<213> ORGANISM: Artificial Sequence
<220> FEATURE:
<223> OTHER INFORMATION: gRNA

<400> SEQUENCE: 19
ggtgagtaaa gagccagct                                               19

<210> SEQ ID NO 20
```

```
<211> LENGTH: 22
<212> TYPE: DNA
<213> ORGANISM: Artificial Sequence
<220> FEATURE:
<223> OTHER INFORMATION: gRNA

<400> SEQUENCE: 20
gtttatataa tatctagcac ag                                              22

<210> SEQ ID NO 21
<211> LENGTH: 20
<212> TYPE: DNA
<213> ORGANISM: Artificial Sequence
<220> FEATURE:
<223> OTHER INFORMATION: gRNA

<400> SEQUENCE: 21
gactcaaatt tataatttgc                                                 20

<210> SEQ ID NO 22
<211> LENGTH: 22
<212> TYPE: DNA
<213> ORGANISM: Artificial Sequence
<220> FEATURE:
<223> OTHER INFORMATION: gRNA

<400> SEQUENCE: 22
gcaaattata aatttgagtc ag                                              22

<210> SEQ ID NO 23
<211> LENGTH: 17
<212> TYPE: DNA
<213> ORGANISM: Artificial Sequence
<220> FEATURE:
<223> OTHER INFORMATION: gRNA

<400> SEQUENCE: 23
gcgtaagtac aatcttt                                                    17

<210> SEQ ID NO 24
<211> LENGTH: 21
<212> TYPE: DNA
<213> ORGANISM: Artificial Sequence
<220> FEATURE:
<223> OTHER INFORMATION: gRNA

<400> SEQUENCE: 24
gaaacatgga cagcataacc a                                               21

<210> SEQ ID NO 25
<211> LENGTH: 23
<212> TYPE: DNA
<213> ORGANISM: Artificial Sequence
<220> FEATURE:
<223> OTHER INFORMATION: gRNA

<400> SEQUENCE: 25
gtttctggct atgcaatagt caa                                             23

<210> SEQ ID NO 26
<211> LENGTH: 20
<212> TYPE: DNA
<213> ORGANISM: Artificial Sequence
<220> FEATURE:
<223> OTHER INFORMATION: gRNA

<400> SEQUENCE: 26
```
ggcaccacta caaaacaaaa                                              20

<210> SEQ ID NO 27
<211> LENGTH: 18
<212> TYPE: DNA
<213> ORGANISM: Artificial Sequence
<220> FEATURE:
<223> OTHER INFORMATION: gRNA

<400> SEQUENCE: 27
ggggatgagt aagctcta                                                18

<210> SEQ ID NO 28
<211> LENGTH: 20
<212> TYPE: DNA
<213> ORGANISM: Artificial Sequence
<220> FEATURE:
<223> OTHER INFORMATION: gRNA

<400> SEQUENCE: 28
gcttactcat cccctgttgg                                              20

<210> SEQ ID NO 29
<211> LENGTH: 19
<212> TYPE: DNA
<213> ORGANISM: Artificial Sequence
<220> FEATURE:
<223> OTHER INFORMATION: gRNA

<400> SEQUENCE: 29
gagcttactc atcccctgt                                               19

<210> SEQ ID NO 30
<211> LENGTH: 20
<212> TYPE: DNA
<213> ORGANISM: Artificial Sequence
<220> FEATURE:
<223> OTHER INFORMATION: gRNA

<400> SEQUENCE: 30
gattccattt tgttttgtag                                              20

<210> SEQ ID NO 31
<211> LENGTH: 22
<212> TYPE: DNA
<213> ORGANISM: Artificial Sequence
<220> FEATURE:
<223> OTHER INFORMATION: gRNA

<400> SEQUENCE: 31
gatttatgag tcttccacca ac                                           22

<210> SEQ ID NO 32
<211> LENGTH: 19
<212> TYPE: DNA
<213> ORGANISM: Artificial Sequence
<220> FEATURE:
<223> OTHER INFORMATION: gRNA

<400> SEQUENCE: 32
gatttgttat ttacaaacg                                               19

<210> SEQ ID NO 33
<211> LENGTH: 22
<212> TYPE: DNA

```
<213> ORGANISM: Artificial Sequence
<220> FEATURE:
<223> OTHER INFORMATION: gRNA

<400> SEQUENCE: 33
gtttggtgag taaagagcca gc                                          22

<210> SEQ ID NO 34
<211> LENGTH: 20
<212> TYPE: DNA
<213> ORGANISM: Artificial Sequence
<220> FEATURE:
<223> OTHER INFORMATION: gRNA

<400> SEQUENCE: 34
ggttatgctg tccatgtttc                                             20

<210> SEQ ID NO 35
<211> LENGTH: 18
<212> TYPE: DNA
<213> ORGANISM: Artificial Sequence
<220> FEATURE:
<223> OTHER INFORMATION: gRNA

<400> SEQUENCE: 35
gtttaacaca tgcagggg                                               18

<210> SEQ ID NO 36
<211> LENGTH: 23
<212> TYPE: DNA
<213> ORGANISM: Artificial Sequence
<220> FEATURE:
<223> OTHER INFORMATION: gRNA

<400> SEQUENCE: 36
gtattgttta acacatgcag ggg                                         23

<210> SEQ ID NO 37
<211> LENGTH: 20
<212> TYPE: DNA
<213> ORGANISM: Artificial Sequence
<220> FEATURE:
<223> OTHER INFORMATION: gRNA

<400> SEQUENCE: 37
ggatgctctc cagacattct                                             20

<210> SEQ ID NO 38
<211> LENGTH: 21
<212> TYPE: DNA
<213> ORGANISM: Artificial Sequence
<220> FEATURE:
<223> OTHER INFORMATION: gRNA

<400> SEQUENCE: 38
gaggatgctc tccagacatt c                                           21

<210> SEQ ID NO 39
<211> LENGTH: 20
<212> TYPE: DNA
<213> ORGANISM: Artificial Sequence
<220> FEATURE:
<223> OTHER INFORMATION: gRNA

<400> SEQUENCE: 39
gagctcgcag cagctgctgc                                             20
```

<210> SEQ ID NO 40
<211> LENGTH: 20
<212> TYPE: DNA
<213> ORGANISM: Artificial Sequence
<220> FEATURE:
<223> OTHER INFORMATION: gRNA

<400> SEQUENCE: 40
gctggcagct gggtccagcc                                              20

<210> SEQ ID NO 41
<211> LENGTH: 21
<212> TYPE: DNA
<213> ORGANISM: Artificial Sequence
<220> FEATURE:
<223> OTHER INFORMATION: gRNA

<400> SEQUENCE: 41
gcagctctgg ctcacactac c                                            21

<210> SEQ ID NO 42
<211> LENGTH: 19
<212> TYPE: DNA
<213> ORGANISM: Artificial Sequence
<220> FEATURE:
<223> OTHER INFORMATION: gRNA

<400> SEQUENCE: 42
gggtccagcc agggtctcc                                               19

<210> SEQ ID NO 43
<211> LENGTH: 21
<212> TYPE: DNA
<213> ORGANISM: Artificial Sequence
<220> FEATURE:
<223> OTHER INFORMATION: gRNA

<400> SEQUENCE: 43
gctcacacta ccaggagacc c                                            21

<210> SEQ ID NO 44
<211> LENGTH: 20
<212> TYPE: DNA
<213> ORGANISM: Artificial Sequence
<220> FEATURE:
<223> OTHER INFORMATION: gRNA

<400> SEQUENCE: 44
gtgtgagcca gagctgcttt                                              20

<210> SEQ ID NO 45
<211> LENGTH: 22
<212> TYPE: DNA
<213> ORGANISM: Artificial Sequence
<220> FEATURE:
<223> OTHER INFORMATION: gRNA

<400> SEQUENCE: 45
gtacttgctg ggacagtgaa tg                                           22

<210> SEQ ID NO 46
<211> LENGTH: 22
<212> TYPE: DNA
<213> ORGANISM: Artificial Sequence
<220> FEATURE:

```
<223> OTHER INFORMATION: gRNA

<400> SEQUENCE: 46
gtccctggtg tcaggaaaat gc                                              22

<210> SEQ ID NO 47
<211> LENGTH: 23
<212> TYPE: DNA
<213> ORGANISM: Artificial Sequence
<220> FEATURE:
<223> OTHER INFORMATION: gRNA

<400> SEQUENCE: 47
gcattttcct gacaccaggg acc                                             23

<210> SEQ ID NO 48
<211> LENGTH: 20
<212> TYPE: DNA
<213> ORGANISM: Artificial Sequence
<220> FEATURE:
<223> OTHER INFORMATION: gRNA

<400> SEQUENCE: 48
gtgttaaaca atacagctag                                                 20

<210> SEQ ID NO 49
<211> LENGTH: 21
<212> TYPE: DNA
<213> ORGANISM: Artificial Sequence
<220> FEATURE:
<223> OTHER INFORMATION: gRNA

<400> SEQUENCE: 49
gctgtattgt ttaacacatg c                                               21

<210> SEQ ID NO 50
<211> LENGTH: 19
<212> TYPE: DNA
<213> ORGANISM: Artificial Sequence
<220> FEATURE:
<223> OTHER INFORMATION: gRNA

<400> SEQUENCE: 50
gtattgttta acacatgca                                                  19

<210> SEQ ID NO 51
<211> LENGTH: 20
<212> TYPE: DNA
<213> ORGANISM: Artificial Sequence
<220> FEATURE:
<223> OTHER INFORMATION: gRNA

<400> SEQUENCE: 51
gcagcctggt ccctggtgtc                                                 20

<210> SEQ ID NO 52
<211> LENGTH: 19
<212> TYPE: DNA
<213> ORGANISM: Artificial Sequence
<220> FEATURE:
<223> OTHER INFORMATION: gRNA

<400> SEQUENCE: 52
gttaaacaat acagctagt                                                  19
```

```
<210> SEQ ID NO 53
<211> LENGTH: 23
<212> TYPE: DNA
<213> ORGANISM: Artificial Sequence
<220> FEATURE:
<223> OTHER INFORMATION: gRNA

<400> SEQUENCE: 53
gttaaacaat acagctagtg gga                                              23
```